United States Patent [19]

Piatak, Jr. et al.

[11] Patent Number: 5,128,460

[45] Date of Patent: Jul. 7, 1992

[54] RECOMBINANT TRICHOSANTHIN AND CODING SEQUENCE

[75] Inventors: Michael Piatak, Jr., Pleasanton; Theresa P. Chow, Portola Valley; Kirk Fry, Palo Alto, all of Calif.

[73] Assignee: Genelabs Incorporated, Redwood City, Calif.

[21] Appl. No.: 504,775

[22] Filed: Apr. 4, 1990

Related U.S. Application Data

[60] Continuation-in-part of Ser. No. 333,184, Apr. 4, 1989, abandoned, and a continuation-in-part of Ser. No. 404,326, Sep. 7, 1989, Pat. No. 5,101,025, which is a division of Ser. No. 333,184, Apr. 4, 1989, abandoned.

[51] Int. Cl.$^5$ ............................................. C12N 15/29
[52] U.S. Cl. .................................. 536/27; 530/370
[58] Field of Search .................. 536/27; 530/370; 435/69.1

[56] References Cited

U.S. PATENT DOCUMENTS

| 4,459,355 | 7/1984 | Cello et al. | 435/172.3 |
|---|---|---|---|
| 4,684,611 | 8/1987 | Schilperoort et al. | 435/172.3 |
| 4,693,976 | 9/1987 | Schilperoot et al. | 435/172.3 |
| 4,743,548 | 5/1988 | Crossway et al. | 435/172.3 |
| 4,795,739 | 1/1989 | Lifson et al. | 514/8 |
| 4,801,540 | 1/1989 | Hiatt et al. | 435/240.4 |
| 4,869,903 | 9/1989 | Lifson et al. | 424/195.1 |

FOREIGN PATENT DOCUMENTS 0286441 10/1988 European Pat. Off.
WO88/09123 12/1988 PCT Int'l Appl.

OTHER PUBLICATIONS

Collins et al., May 1990, J. Biol. Chem. 265(15):8665-8669.
Xuejun et al., 1986, Nature 321:477-478.
Tsao, S. W., et al., Toxicon 24(8):831 (1986).
Bonnerjea, J., et al., Bio/Technology 4:955 (1986).
Lee, C. C., et al., Science 239:1288 (1988).
Till, M. A., et al., Science 242:1166 (1988).
Gyllensten, U. B., et al., Proc. Natl. Acad. Sci. U.S.A. 85:7652 (1988).
Chow, T. P., et al., J. Biol. Chem. 265(15):8670 (1990).
Ready, M. P., et al., Proteins: Struct. Funct. Genet. 3(1):53 (1988).
Chaudhary, V. K., et al., Nature 335:369 (1988).
Wang, Q., et al., Shiyan Shengwu Xuebao 20(4):515 (1987)-Abstract from Chemical Abstracts.
Zi-Wei, G., et al., ACTA Chimica Sinica 42(9):943 (1984).
Yu, W., et al., Pure and Appl. Chem. 58(5):789 (1986).
Yeung, H. W., et al., Immunopharm. and Immunotox. 9(1):25 (1987).
Yeung, H. W., et al., Int. J. Pep. Prot. Res. 27:325 (1986).
Casellas, P., et al., Eur. J. Biochem. 176, 581-588 (1988).
Maraganore, J. M., et al., J. Biol. Chem. 262(24) 11628-11633 (1987).
McGrath, M. S., et al., Proc. Natl. Acad. Sci. U.S.A. 86 2844-2848.

(List continued on next page.)

Primary Examiner—Robert A. Wax
Assistant Examiner—Keith C. Furman
Attorney, Agent, or Firm—Peter J. Dehlinger; Gary R. Fabian

[57] ABSTRACT

Disclosed are the entire protein and nucleic acid coding sequences for unprocessed and mature trichosanthin protein from *Trichosanthes kirilowii*. A recombinant trichosanthin protein produced from the coding sequence, and the trichosanthin protein with amino-terminal and/or carboxy-terminal extensions are also described. Primers derived from the coding sequence are disclosed for use in obtaining the coding sequences of ribosome-inactivating-proteins which have regions of amino acid sequence identical to those of trichosanthin. Further, a multigene family of ribosome-inactivating-protein encoding genes of *Trichosanthes kirilowii* is also described.

2 Claims, 36 Drawing Sheets

OTHER PUBLICATIONS

Rogers, S. G., et al., Methods in Enzymology 153 253–276 (1987).

Sela, I., Methods in Enzymology 119 734–745 (1986).

Deblaere, R., et al., Methods in Enzymology 153 277–292 (1987).

Weising, K., et al., Annu. Rev. Genet. 22 421–477 (1988).

Benfey, P. N., et al., Science 244 174–181 (1989).

Abel, P. P. et al., Science 232 738–743 (1986).

Vaeck, M., et al., Nature 328, 33–37 (1987).

Fassuliotis, G., Chapter 48 in *Vistas on Nematology*, edited by J. A. Veech et al., (1987).

Yeung, H. W., et al., Immunopharmacology and Immunotocixology, 9(1) 24–46 (1987).

```
Asp Val Ser Phe Arg Leu Ser Gly Ala Thr Ser Ser Ser Tyr Gly Val Phe Ile Ser Asn20
Asp Val Ser Phe Arg Leu Ser Gly Ala Thr Ser Ser Ser Tyr Gly Val Phe Ile Ser Asn

Leu Arg Lys Ala Leu Pro Asn Glu Arg Lys Leu Tyr Asp Ile Pro Leu Leu Arg Ser Ser40
Leu Arg Lys Ala Leu Pro Asn Glu Arg Lys Leu Tyr Asp Leu Pro Leu Leu Arg Ser Ser

Leu Pro Gly Ser Gln Arg Tyr Ala Leu Ile His Leu Thr Asn Tyr Ala Asp Glu Thr Ile60
Leu Pro Gly Ser Gln Arg Tyr Ala Ile Ile His Leu Thr Asn Tyr Ala Asp Glu  <---

Ser Val Ala Ile Asp Val Thr Asn Val  Tyr Ile Met Gly Tyr Arg Ala Gly Asp Thr Ser80
--> Val Ala Ile Asp Val Thr Asn Val<>Tyr Ile Met Gly Tyr Arg Ala Gly Asp Thr Ser
                                  <Asp Ala Gly Leu Pro Arg Asn Ala Val Leu>
                                    |—————————— A ——————————|
Tyr Phe Phe Asn Glu Ala Ser Ala Thr Glu Ala Ala Lys Tyr Val Phe Lys Asp Ala Met100
Tyr Phe Phe Asn Glu Ala Ser Ala Thr Glu Ala Ala Lys Tyr Val Phe Lys Asp Ala Met

->|
Arg Lys Val Thr Leu Pro Tyr Ser Gly Asn Tyr Glu Arg Leu Gln Thr Ala Ala Gly Lys120
Arg Lys Val Thr Leu Pro Tyr Ser Gly Asn Tyr Glu Arg Leu Gln Thr Ala Ala Gly Gly

Ile Arg Glu Asn Ile Pro Leu Gly Leu Pro Ala Leu Asp Ser Ala Ile Thr Thr Leu Phe140
Leu Arg Glu Asn Ile Pro Leu Gly Leu Pro Ala Leu Asp Ser Ala Ile Thr Thr Leu Phe

Tyr Tyr Asn Ala Asn Ser Ala Ala Ser Ala Leu Met Val Leu Ile Gln Ser Thr Ser Glu160
Tyr Tyr Asn Ala Asn Ser Ala Ala Ser Ala Leu Met Val Leu Ile Gln Ser Thr Ser Glu
```

Fig. 1

```
                |<----------------- B -----------------|
Ala Ala Arg Tyr Lys Phe Ile Glu Gln Gln Ile Gly Lys Arg Val Asp Lys Thr Phe Leu¹⁸⁰
Ala Ala Arg Tyr Lys Phe Ile Glu Gln Gln Ile Gly Ser Arg Val Asp Lys Thr Phe Leu

Pro Ser Leu Ala Ile Ile Ser Leu Glu Asn Ser  Trp Ser Ala Leu Ser Lys Gln Ile Gln²⁰⁰
Pro Ser Leu Ala Ile Ile Ser Leu Glu Asn Ser<>Trp Leu Ala Leu Ser Lys Gln Ile Gln
                                              Leu

Ile Ala Ser Thr Asn Asn Gly Gln Phe Glu Ser Pro Val Val Leu Ile Asn Ala Gln Asn²²⁰
Ile Ala Ser Thr Asn Asn Gly Thr Phe Glu Ser Pro Val Val Leu Ile Asn Ala Gln Asn

Gln Arg Val Thr Ile Thr Asn Val Asp Ala Gly Val Val Thr Ser Asn Ile Ala Leu Leu²⁴⁰
Gln Arg <-- --- --- --- --- --- --- --- --- --- --- --- --- --- --- --- --- ---

Leu Asn Arg Asn Asn Met Ala²⁴⁷
--- ---  --> Asn Asn Met Ala
```

Fig. 1 (con't)

```
1   GTT GGA CTC CCN GCT TTG GAC AGT GCC ATT ACC ACT TTG TTT   42
    Val Gly Leu Pro Ala Leu Asp Ser Ala Ile Thr Thr Leu Phe
    Leu Asp Ser ??? Leu Trp Thr Val Pro Leu Pro Leu Cys Phe
    Trp Thr Pro ??? Phe Gly Gln Cys His Tyr His Phe Val Leu

43  TAC TAC AAC GCC AAT TCT GCT GCT TCG GCA CTT ATG GTA CTC   84
    Tyr Tyr Asn Ala Asn Ser Ala Ala Ser Ala Leu MET Val Leu
    Thr Thr Pro Ile Leu Leu Leu Arg His Leu Trp Tyr Ser
    Leu Gln Arg Gln Phe Cys Cys Phe Gly Thr Tyr Gly Thr His

85  ATT CAG TCG ACG TCT GAG GCT GCA AGG TCA AT               116
    Ile Gln Ser Thr Ser Glu Ala Ala Arg Ser
    Phe Ser Arg Arg Leu Arg Leu Gln Gly Gln
    Ser Val Asp Val TER Gly Cys Lys Val Asn
```

Fig. 3A

```
116 ATT GAC CTT GCA GCC TCA GAC GTC GAC TGA ATG AGT ACC ATA  75
    Ile Asp Leu Ala Ala Ser Asp Val Asp TER MET Ser Thr Ile
    Leu Thr Leu Gln Pro Gln Thr Ser Thr Glu TER Val Pro TER
    TER Pro Cys Ser Leu Arg Arg Arg Leu Asn Glu Tyr His Lys

74 AGT GCC GAA GCA GCA GAA TTG GCG TTG TAG TAA AAC AAA GTG  33
    Ser Ala Glu Ala Ala Glu Leu Ala Leu TER TER Asn Lys Val
    Val Pro Lys Gln Gln Asn Trp Arg Cys Ser Lys Thr Lys Trp
    Cys Arg Ser Ser Arg Ile Gly Val Val Val Lys Gln Ser Gly

32 GTA ATG GCA CTG TCC AAA GCN GGG AGT CCA AC                1
    Val MET Ala Leu Ser Lys Ala Gly Ser Pro
    TER Trp His Cys Pro Lys ??? Gly Val Gln
    Asn Gly Thr Val Gln Ser ??? Glu Ser Asn
```

```
EcoR I
GAATTCAAATATTTCTGAATAAATTCATTGTAGAGAAATGATGAGAAAACAAGAACAATTTCAAAAACAAA   80

AAATAAAAAACAAATGGTTTATCAAAGAAGCCCGAATTTATTATCAAAAGCGAAAGTTAATAATATCTAAAAAAAACT  160

ATTACCCTTATAAGAAGCTATTACCTAGATGGCATAAGATCATACTTTTATTTTTGATTTAGACTAGAAATACACTAATAT  240

ATTGTGGACATAGCCAGACAACGATTAGATGGCATACCCTCTCTATAAAAACCACAGCTTGAGATGCTCCAATGGCATCCA  320

340
AATTCCTCAAGTCAAAAG ATG ATC AGA TTC TTA GTC CTC TCT TTG CTA ATT CTC ACC CTC TTC
                   MET Ile Arg Phe Leu Val Leu Ser Leu Leu Ile Leu Thr Leu Phe
                                   -20

400
CTA ACA ACT CCT GCT GTG GAG GGC GAT GTT AGC TTC CGT TTA TCA GGT GCA ACA AGC AGT
Leu Thr Thr Pro Ala Val Glu Gly Asp Val Ser Phe Arg Leu Ser Gly Ala Thr Ser Ser
                                   |Asp
                                   -1   1

500
TCC TAT GGA GTT TTC ATT TCA AAT CTG AGA AAA GCT CTT CCA AAT GAA AGG AAA CTG TAC
Ser Tyr Gly Val Phe Ile Ser Asn Leu Arg Lys Ala Leu Pro Asn Glu Arg Lys Leu Tyr
450                              10                                20

550
GAT ATC CCT CTG TTA CGT TCC TCT CTT CCA GGT TCT CAA CGC TAC GCA TTG ATC CAT CTC
Asp Ile Pro Leu Leu Arg Ser Ser Leu Pro Gly Ser Gln Arg Tyr Ala Leu Ile His Leu
                                  40
```

| ACA | AAT | TAC | GCC | GAT | GAA | ACC | ATT | TCA | GTG | GCC | ATA | GAC | GTA | ACG | AAC | GTC | TAT | ATT | ATG |
|-----|-----|-----|-----|-----|-----|-----|-----|-----|-----|-----|-----|-----|-----|-----|-----|-----|-----|-----|-----|
| Thr | Asn | Tyr | Ala | Asp | Glu | Thr | Ile | Ser | Val | Ala | Ile | Asp | Val | Thr | Asn | Val | Tyr | Ile | MET |
| Thr | Asn | Tyr | Ala | Asp | Glu | Thr | Ile | Ser | Val | Ala | Ile | Asp | Val | Thr | Asn | Val | Tyr | Ile | Met |

EcoR V                                              600

| GGA | TAT | CGC | GCT | GGC | GAT | ACA | TCC | TAT | TTT | TTC | AAC | GAG | GCT | TCT | GCA | ACA | GAA | GCT | GCA |
|-----|-----|-----|-----|-----|-----|-----|-----|-----|-----|-----|-----|-----|-----|-----|-----|-----|-----|-----|-----|
| Gly | Tyr | Arg | Ala | Gly | Asp | Thr | Ser | Tyr | Phe | Phe | Asn | Glu | Ala | Ser | Ala | Thr | Glu | Ala | Ala |
| Gly | Tyr | Arg | Ala | Gly | Asp | Thr | Ser | Tyr | Phe | Phe | Asn | Glu | Ala | Ser | Ala | Thr | Glu | Ala | Ala |

650                                                           700

| AAA | TAT | GTA | TTC | AAA | GAC | GCT | ATG | CGA | AAA | GTT | ACG | CTT | CCA | TAT | TCT | GGC | AAT | TAC | GAA |
|-----|-----|-----|-----|-----|-----|-----|-----|-----|-----|-----|-----|-----|-----|-----|-----|-----|-----|-----|-----|
| Lys | Tyr | Val | Phe | Lys | Asp | Ala | MET | Arg | Lys | Val | Thr | Leu | Pro | Tyr | Ser | Gly | Asn | Tyr | Glu |
| Lys | Tyr | Val | Phe | Lys | Asp | Ala | Met | Arg | Lys | Val | Thr | Leu | Pro | Tyr | Ser | Gly | Asn | Tyr | Glu |

750                                                                                         800

| AGG | CTT | CAA | ACT | GCT | GCG | GGC | AAA | ATA | AGG | GAA | AAT | ATT | CCG | CTT | GGA | CTC | CCA | GCT | TTG |
|-----|-----|-----|-----|-----|-----|-----|-----|-----|-----|-----|-----|-----|-----|-----|-----|-----|-----|-----|-----|
| Arg | Leu | Gln | Thr | Ala | Ala | Gly | Lys | Ile | Arg | Glu | Asn | Ile | Pro | Leu | Gly | Leu | Pro | Ala | Leu |
| Arg | Leu | Gln | Thr | Ala | Ala | Gly | Lys | Ile | Arg | Glu | Asn | Ile | Pro | Leu | Gly | Leu | Pro | Ala | Leu |

850

| GAC | AGT | GCC | ATT | ACC | ACT | TTG | TTT | TAC | TAC | AAC | GCC | AAT | TCT | GCT | GCG | TCG | GCA | CTT | ATG |
|-----|-----|-----|-----|-----|-----|-----|-----|-----|-----|-----|-----|-----|-----|-----|-----|-----|-----|-----|-----|
| Asp | Ser | Ala | Ile | Thr | Thr | Leu | Phe | Tyr | Tyr | Asn | Ala | Asn | Ser | Ala | Ala | Ser | Ala | Leu | MET |
| Asp | Ser | Ala | Ile | Thr | Thr | Leu | Phe | Tyr | Tyr | Asn | Ala | Asn | Ser | Ala | Ala | Ser | Ala | Leu | Met |

Sal I                                  900

| GTA | CTC | ATT | CAG | TCG | ACG | TCT | GAG | GCT | GCG | AGG | TAT | AAA | TTT | ATT | GAG | CAA | CAA | ATT | GGG |
|-----|-----|-----|-----|-----|-----|-----|-----|-----|-----|-----|-----|-----|-----|-----|-----|-----|-----|-----|-----|
| Val | Leu | Ile | Gln | Ser | Thr | Ser | Glu | Ala | Ala | Arg | Tyr | Lys | Phe | Ile | Glu | Gln | Gln | Ile | Gly |
| Val | Leu | Ile | Gln | Ser | Thr | Ser | Glu | Ala | Ala | Arg | Tyr | Lys | Phe | Ile | Glu | Gln | Gln | Ile | Gly |

Fig. 4 (con't)

```
                                        950
AAG CGC GTT GAC AAA ACC TTC CTA CCA AGT TTA GCA ATT ATA AGT TTG GAA AAT AGT TGG
Lys Arg Val Asp Lys Thr Phe Leu Pro Ser Leu Ala Ile Ile Ser Leu Glu Asn Ser Trp
Lys Arg Val Asp Lys Thr Phe Leu Pro Ser Leu Ala Ile Ile Ser Leu Glu Asn Ser Trp
                            1000                                            Pro
TCT GCT CTC TCC AAG CAA ATT CAG ATA GCG AGT ACT AAT GGA CAG TTT GAA ACT CCT
Ser Ala Leu Ser Lys Gln Ile Gln Ile Ala Ser Thr Asn Gly Gln Phe Glu Thr Pro
Ser Ala Leu Ser Lys Gln Ile Gln Ile Ala Ser Thr Asn Gly Gln Phe Glu Ser Pro
     1050                                200                                    1100
GTT GTG CTT ATA AAT GCT CAA AAC CAA CGA GTC ATG ATA ACC AAT GTT GAT GCT GGA GTT
Val Val Leu Ile Asn Ala Gln Asn Gln Arg Val MET Ile Thr Asn Val Asp Ala Gly Val
Val Val Leu Ile Asn Ala Gln Asn Gln Arg Val MET Ile Thr Asn Val Asp Ala Gly Val
                                                               1150  Nco I
GTA ACC TCC AAC ATC GCG TTG CTG AAT CGA AAC AAT ATG GCA GCC ATG GAT GAC GAT
Val Thr Ser Asn Ile Ala Leu Leu Asn Arg Asn Asn Met Ala Ala MET Asp Asp Asp
Val Thr Ser Asn Ile Ala Leu Leu Asn Arg Asn Asn Met Ala Ala MET Asp Asp Asp
                            240                            247
                                                     1200
GTT CCT ATG ACA CAG AGC TTT GGA TGT GGA AGT TAT GCT ATT TAG TGTAACTTCAAGCTACGT
Val Pro MET Thr Gln Ser Phe Gly Cys Gly Ser Tyr Ala Ile TER
```

Fig. 4 (con't)

Fig. 9

```
                            140
TCS-  P A I D S T I T A E V A T        A S P E A
ricA- G P L E I S A Y V V T G T L P E T
abrA- Q A L T H G I S   F R   C G N D E E R
BPSI- T A I L G R K A D K A S G P K Q G O A R K
MIRA- F R L E N S V N I S G K A S D V K K Q A K 160
TCS-  A S A L M V L Q S T S H A A R Y F E
ricA- L R S L I C L Q M I S P A R F Q V T
abrA- K A R L L W I Q M V A A A R R K S
BPSI- E A V F T B H     N V N A T R Q T V S
MIRA-   F K L L A Q M V S H A A R P K Y L S 180
TCS-  Q Q T G K R V D K T F       L S L I I
ricA- G E M R T R I R Y N   R R E A L P S V
abrA- N R F V R V S I Q T G T A F Q     G K A G N E
BPSI- G F V A G L L H P K A V E K K G K I A G E N E
MIRA- D K I P S E K Y E E       V T V D E Y S 200
TCS-  I S L E N S   S A R S K Q G I A T T N
ricA- I T I E N S   G D R N L S T A I Q E S S N Q
abrA- I S L E N N   D N D N R G A V Q E S V Q
BPSI- M K A Q V N G N Q D K L S A T L L K T D V K P
MIRA- T A I E N N   A K I S T A V Y N S K P S T 220
TCS-  G Q T E T V V L I A Q I Q R K V M I T N D V
ricA- G A F A S P I Q L Q R R N G S K F S I Y D S V
abrA- D I F P N Q T K L T N I R E I P S I R D S E L
BPSI- P P G K S P A K F T P E K M G S R T A E Q
MIRA- T I A T K C Q L A S P V T I S P W I F K T 240      247
TCS-  D A G V V T S N L A U E N N N M A
ricA- S H   I L I P I L A D N V Y R A E     P S S
abrA- E H   P T V A V L A H M E V G N P F N G
BPSI- A N A       T D G I S D F E V G G L T
MIRA- V E E I   K L V M G L E K S S TCS-
ricA- Q F
abrA-
BPSI- V A K A L E L F H A S G G K
MIRA-
```

Fig. 9 (con't)

```
                                           M  D
1        *            *            *       *
GGTACCCGCGGATAACAAGGATCCGGAGGAAAAAACCATGGA
GGTAC^C(KpnI)      G^GATCC(BamHI)    C^CATGG
     CCGC^GG(SacII)    T^CCGGA(BspMII)

V  S  F  R  L  S  G  A  T  S  S  S  Y
       *            *            *       80
TGTTTCTTTTCGTCTTTCCGGTGCAACCTCTTCATCTTAT
(NcoI)

G  V  F  I  S  N  L  R  K  A  L  P  N  E
       *            *            *            *
GGTGTATTTATTTCTAACCTGCGTAAAGCTTTGCCGAACGAA
                ACCTGCNNNN^(BpsMI)
                       A^AGCTT(HinDIII)

R  K  L  Y  D  I  P  L  L  R  S  S  L
       *            *            *       160
CGCAAACTGTATGACATCCCGCTGTTGCGTAGCTCCCTG

P  G  S  Q  R  Y  A  L  I  H  L  T  N  Y
       *            *            *            *
CCGGGCAGCCAGCGTTATGCATTAATTCATCTGACGAATTAC
                  ATGCA^T(NsiI)

A  D  E  T  I  S  V  A  I  D  V  T  N
       *            *            *       240
GCCGATGAAACTATCTCCGTGGCAATCGATGTTACCAAT
                             AT^CGAT(ClaI)

V  Y  I  M  G  Y  R  A  G  D  T  S  Y  F
       *            *            *            *
GTCTACATTATGGGCTATCGCGCCGGTGACACTAGTTATTTCT
                             A^CTAGT(SpeI)
```

Fig. 11

```
  F   N   E   A   S   A   T   E   A   A   K   Y   V
      *           *           *          320
TTAATGAGGCTAGCGCGACTGAAGCCGCTAAATACGTA
        G^CTAGC(NheI)                 TAC^GTA
                                      (SnaBI)

F   K   D   A   M   R   K   V   T   L   P   Y   S
      *           *           *           *
TTCAAGGATGCGATGCGTAAAGTGACCCTGCCATACAGC

G   N   Y   E   R   L   Q   T   A   A   G   K   I   R
      *           *           *          400
GGCAACTATGAACGTCTGCAGACGGCAGCCGGTAAGATCCGT
                   CTGCA^G(PstI)

E   N   I   P   L   G   L   P   A   L   D   S   A
      *           *           *           *
GAGAACATTCCGCTTGGCTTACCAGCTCTAGACTCCGCGA
                                T^CTAGA(XbaI)

I   T   T   L   F   Y   Y   N   A   N   S   A   A   S
      *           *           *          480
TCACGACTCTCTTCTATTACAACGCAAATTCCGCCGCAAGC

A   L   M   V   L   I   Q   S   T   S   E   A   A
      *           *           *           *
GCGCTCATGGTTTTGATTCAAAGTACTAGCGAAGCTGCA
G^CGCGC(BssHII)         AGT^ACT(ScaI)

R   Y   K   F   I   E   Q   Q   I   G   K   R   V   D
      *           *           *          560
CGCTACAAATTCATCGAACAGCAAATTGGCAAACGCGTGGAC
                                    A^CGCGT(MluI)
```

Fig. 11 (con't)

```
      K   T   F   L   P   S   L   A   I   I   S   L   E   N
      *           *           *           *           *
AAAACCTTTCTGCCTTCGCTGGCCATTATCTCTCTTGAGAAT
                        TGG^CCA(BalI)         G^AA

S   W   S   A   L   S   K   Q   I   Q   I   A   S
                      *           *          640
TCGTGGTCTGCCCTGAGCAAGCAGATCCAGATCGCGTCG
TTC(EcoR1)                        G^TCGAC
                                   (SalI)

T   N   N   G   Q   F   E   S   P   V   V   L
      *           *           *           *
ACCAACAATGGTCAGTTCGAAAGCCCGGTCGTTTTAA

I   N   A   Q   N   Q   R   V   T   I   T   N   V   D   A
      *           *           *           *                   730
TTAATGCGCAGAATCAACGTGTGACCATCACGAACGTGGATGCG
        TGC^GCA(FspI)

G   V   V   T   S   N   I   A   L   L   N   R   N
              *           *           *           *
GGAGTTGTGACGTCCAATATCGCCCTGCTTTTAAACCGTAAC
        GACGT^C(AatII)              TTT^AAA(DraI)

N   M   A   Z   Z
      *           *          800
AATATGGCATAATAAGGATCCCGAGCTC
              G^GATCC(BamHI)
                    GAGCT^C(SacI)
```

Fig. 11 (con't)

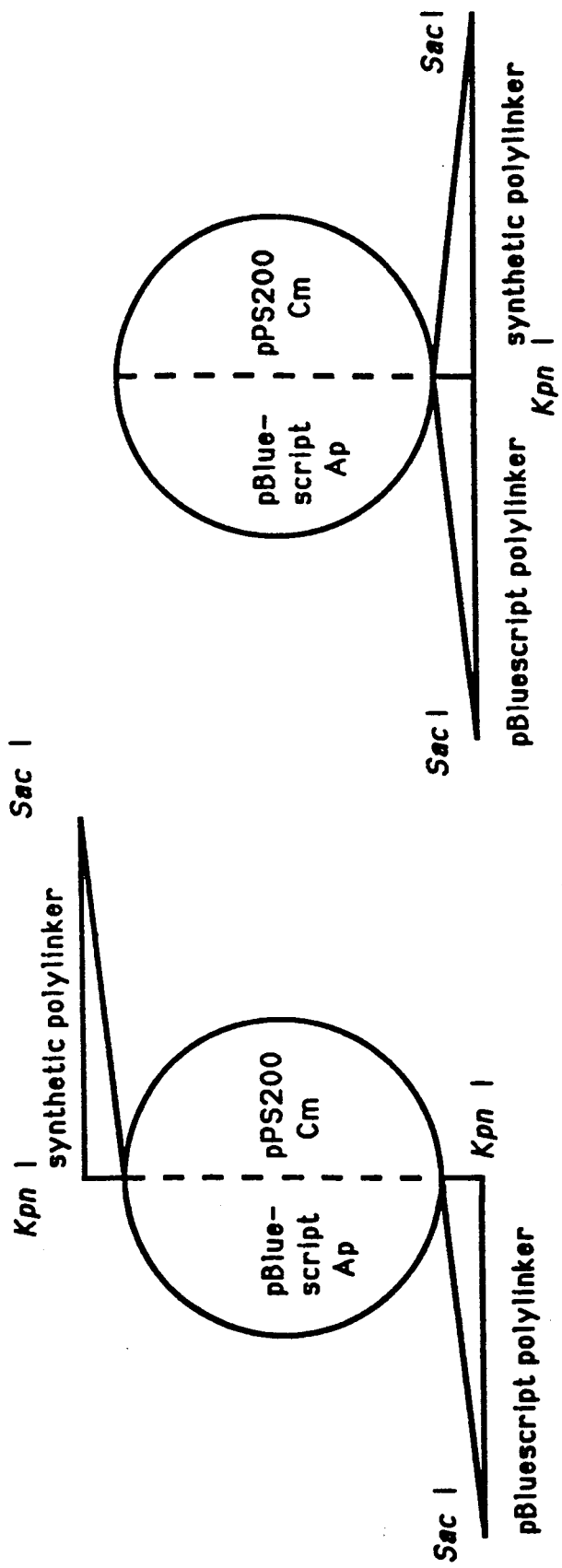

```
  1 GAAT TCA CAA AAT TGC TCT GAG GCC ATA ACT CAC TAT AAA AAC                43
 44 CAT ACG TTG AGA TGG TAT AAT GGC ATC CAA AGC AAT CGA GTG                 85
 86 GGA AAG ATG AAT AGA TTC TCA GTG CTT TAT TTG TTA ATT CTC                127
         Met Asn Arg Phe Ser Val Leu Tyr Leu Leu Ile Leu
128 GCC ATC TTC TTT GGA GGT CCT CCT GTT GAA GGC GAT AAT ATC                169
    Ala Ile Phe Phe Gly Gly Pro Pro Val Glu Gly Asp Asn Ile
170 ATC TTC CGT TTG TCG GGA GCT GAT TCC AAA TCT TAT AGC AAG                211
    Ile Phe Arg Leu Ser Gly Ala Asp Ser Lys Ser Tyr Ser Lys
212 TTC ATA ACA TCT CTG AGG AAC AAT CTC TTG CTT CCA AAT GCT GGA AAA        253
    Phe Ile Thr Ser Leu Arg Asn Asn Leu Leu Pro Asn Ala Gly Lys
254 GTG TTC AAT ATA CCT CTA ATG CAA CTC TCC AGT GCT TCG AGC TCA            295
    Val Phe Asn Ile Pro Leu Met Gln Leu Ser Ser Ala Ser Ser
296 GGA CGC TAC AAA CTA ATG CTC TCC GAT TAT GAG GAG AAA                    337
    Gly Arg Tyr Lys Leu Met Leu Ser Asp Tyr Glu Glu Lys
338 ACC ATC ACG GTG GCT ATA GAC GTA ACA AAC GTT TAT CTT ATG                379
    Thr Ile Thr Val Ala Ile Asp Val Thr Asn Val Tyr Leu Met
```

Fig. 16

```
380 GGG TAT CTT GTC AAT ACA ACA TCC TAC TTT TTC AAC GAG TCT  421
    Gly Tyr Leu Val Asn Thr Thr Ser Tyr Phe Phe Asn Glu Ser

422 GAT GCT CAA TTA GCT TCT AAA TTT GTA TTC AAA GGT AGT ACG  463
    Asp Ala Gln Leu Ala Ser Lys Phe Val Phe Lys Gly Ser Thr

464 ATT ATT ACA CTT CCA TAT TCT GGC AAT TAC CAA AGG CTT CAA  505
    Ile Ile Thr Leu Pro Tyr Ser Gly Asn Tyr Gln Arg Leu Gln

506 ATT GCT GGC AAA GAA AGA GAC AGT GCC ATT CCC CTT GGA TTC  547
    Ile Ala Gly Lys Glu Arg Asp Ser Ala Ile Pro Leu Gly Phe

548 CTA GCC TTG GAC AGT GCC ATT TCC ACC TTA TAT CAT TAT GAC  589
    Leu Ala Leu Asp Ser Ala Ile Ser Thr Leu Tyr His Tyr Asp

590 TCC AAA GCT GCT GCA TTT CTC GTA ATC ATT CAG ACC  631
    Ser Lys Ala Ala Ala Phe Leu Val Ile Ile Gln Thr

632 ACT GCC GAG GCT TCA AGA TTT AAA TAT ATT GAG AAA CAA ATT  673
    Thr Ala Glu Ala Ser Arg Phe Lys Tyr Ile Glu Lys Gln Ile

674 ATC GAT AGA ATT C  686
    Ile Asp Arg Ile
```

Fig. 16 (con't)

Fig. 17 clone 24

(a) CAACCTCAACAACTTAACAGTCTACAACAGTGTGTAACAAAATAACAATCCCTCTGAAAAATCACAATTGAAACA 80

EcoR V                                            150

(b) GAATTTAAAATATACAAATAATTGACTGAGATATCCTAATAGCATCCAAGCAATCGAGTGGAAAG ATG AAT AGA
                                                                           Met Asn Arg
                                                                                   -23   -1

200
TTC CCA ATG CTT TCT TTG TTA ATT CTC GCC ATT TTC CTT CGA GGT CCT CCT GTT GAA GGC
Phe Pro Met Leu Ser Leu Leu Ile Leu Ala Ile Phe Leu Arg Gly Pro Pro Val Glu Gly
-20                                                                           -1

250
GAA AAT ATC ATC TTC CGT TTG TCG GGA GCT TCC GAT TCC AAA TCT TAT AGC AAG TTC ATA ACA
Glu Asn Ile Ile Phe Arg Leu Ser Gly Ala Asp Ser Lys Ser Tyr Ser Lys Phe Ile Thr
1                                                                              20

300
TCT CTG AGG AAC AAT CTC CCA AAT GCT GGA TTC AAT ATA ACT CTA TTG CTT CCC
Ser Leu Arg Asn Asn Leu Pro Asn Ala Gly Phe Asn Ile Thr Leu Leu Pro
                                                        40

350
AGT GCT TCT GGC TCA GGG CGC TAC AAA CTA ATG CAA CTC TCC AAT TAT GAG GAC AAA ACC
Ser Ala Ser Gly Ser Gly Arg Tyr Lys Leu MET Gln Leu Ser Asn Tyr Glu Asp Lys Thr
                                                                    60

450
ATC ACG GTG GCT ATA GAC GTA ACA AAC GTT TAT CTT ATG GGG TTT CAT GTC AAT ACA ACA
Ile Thr Val Ala Ile Asp Val Thr Asn Val Tyr Leu MET Gly Phe His Val Asn Thr Thr
                                                                        80

500
TCC TAC TTT TTC AAC GAG TCT GAT GCT CAA TTA GCT TCT AAA GTA TTT AAA GGT AGT
Ser Tyr Phe Phe Asn Glu Ser Asp Ala Gln Leu Ala Ser Lys Phe Val Phe Lys Gly Ser
                                                                         100

550
ACG ATT ATT ACA CTT CCA TAT TCT GGC AAT TAC CAA AGG CTT CAA ATT GCT GCT AAA
Thr Ile Ile Thr Leu Pro Tyr Ser Gly Asn Tyr Gln Arg Leu Gln Ile Ala Ala Gly Lys
                                                                         120

```
                                    600
GAA AGA GAC TCC ATT CCC CTT GGA TTC CTA GCC TTG GAC AGT GCC ATT TCC ACC TTA TAT
Glu Arg Asp Ser Ile Pro Leu Gly Phe Leu Ala Leu Asp Ser Ala Ile Ser Thr Leu Tyr
                                                                            140
                   650
CAT TAT GAC TCC AAA GCT GCT GCG GCA TTT CTC GTA ATC ATT CAG ACC ACT GCC GAG
His Tyr Asp Ser Lys Ala Ala Ala Ala Phe Leu Val Ile Ile Gln Thr Thr Ala Glu
                                                                         160
700                                        Cla I    EcoR I            750
GCT TCA AGA TTT AAA TAT ATT GAG AAA CAA ATT ATC GAT AGA ATT CAT AAA AAC GAG GTG
Ala Ser Arg Phe Lys Tyr Ile Glu Lys Gln Ile Ile Asp Arg Ile His Lys Asn Glu Val
                                                                             180
                                                     800
CCG AGT CTA GCA GCT ATA AGT TTG GAA AAT GAA TGG TCT CTC TCC AAA CAA ATT CAG
Pro Ser Leu Ala Ala Ile Ser Leu Glu Asn Glu Trp Ser Leu Leu Ser Lys Gln Ile Gln
                                                                             200
                                    850
ATA GCA AGC TCT AAT AAC GGA AAA TTT CAA ACT CCT GTC AAG ATT ATT AAC GAT AAA GGC
Ile Ala Ser Ser Asn Asn Gly Lys Phe Gln Thr Pro Val Lys Ile Ile Asn Asp Lys Gly
                                                                             220
                       900
GTT TCA GTC GAA ATT ACC AAC GTT AGT TCT CTG GTT GTA GTA ACC TCC AAC ATC AAG CTG CTG
Val Ser Val Glu Ile Thr Asn Val Ser Ser Leu Val Val Val Thr Ser Asn Ile Lys Leu Leu
                                                                                  240
                           950
CTA AAC AAG CAA AAT ATT GCA GCT TTT GAC AAC GAT ATT TCT ACA ACG CAC TGAGGCTTGGA
Leu Asn Lys Gln Asn Ile Ala Ala Phe Asp Asn Asp Ile Ser Thr Thr His
                                                                 257
1000
GCTACGAGATGCCTTGACTATGGGTATGGAAATTAGGTTAAGACTCCACTTGAAGAGTATATGTTGTTGTTGGAGTT
         1100                                          1150
```

Fig. 17 (con't)

Fig. 18 clone 2

(a) 
```
                                                    EcoR V                        80
TCTGAAAAATCACAATTGAAACAGAATTTAAAATATACAAATAATTGACTGAGATATCCTAATAGCATCCAAAGCAATC
```

(b)
```
                      100
GAGTGGAAAG ATG AAT AGA TTC CCA ATG CTT TCT TTG TTA ATT CTC GCC ATT TTC CTT CGA
           Met Asn Arg Phe Pro Met Leu Ser Leu Leu Ile Leu Ala Ile Phe Leu Arg
           -23                 -20                                              
                                                                            200
      150
GGT CCT CCT GTT GAA GGC GAA AAT ATC ATC CGT TTG TCG GGA GCT GAT TCC AAA TCT
Gly Pro Pro Val Glu Gly Glu Asn Ile Ile Arg Leu Ser Gly Ala Asp Ser Lys Ser
                         -1  1                                              
                                                    250
TAT AGC AAG TTC ATA ACA TCT CTG AGG AAC AAT CTC CCA AAT GCT GGA AAA GTG TTC AAT
Tyr Ser Lys Phe Ile Thr Ser Leu Arg Asn Asn Leu Pro Asn Ala Gly Lys Val Phe Asn
                 20

300
ATA ACT CTA TTG CTT CCC AGT GCT TCT GGC TCA GGG CGC TAC AAA CTA ATG CAA CTC TCC
Ile Thr Leu Leu Leu Pro Ser Ala Ser Gly Ser Gly Arg Tyr Lys Leu Met Gln Leu Ser
             40

350
AAT TAT GAG GAC AAA ACC ATC ACG GTG GCT ATA GAC GTA ACA AAC GTT TAT CTT ATG GGG
Asn Tyr Glu Asp Lys Thr Ile Thr Val Ala Ile Asp Val Thr Asn Val Tyr Leu Met Gly
                 60
                                400
TTT CAT GTC AAT ACA TCC TAC TTT TTC AAC GAG TCT GAT GCT CAA TTA GCT TCT AAA
Phe His Val Asn Thr Ser Tyr Phe Phe Asn Glu Ser Asp Ala Gln Leu Ala Ser Lys
                 80

450                                                               500
TTT GTA TTC AAA GGT AGT ACG ATT ATT ACA CTT CCA TAT TCT GGC AAT TAC CAA AGG CTT
Phe Val Phe Lys Gly Ser Thr Ile Ile Thr Leu Pro Tyr Ser Gly Asn Tyr Gln Arg Leu
                 100

550
CAA ATT GCT GCT GGC AAA GAA AGA GAC TCC ATT CCC CTT GGA TTC CTA GCC TTG GAC AGT
Gln Ile Ala Ala Gly Lys Glu Arg Asp Ser Ile Pro Leu Gly Phe Leu Ala Leu Asp Ser
                 120
```

```
                                                600
GCC ATT TCC ACC TTA TAT CAT TAT GAC TCC AAA GCT GCT GCG GCA TTT CTC GTA ATC
Ala Ile Ser Thr Leu Tyr His Tyr Asp Ser Lys Ala Ala Ala Ala Phe Leu Val Ile
                140
                                                        ClaI
ATT CAG ACC ACT GCC GAG GCT TCA AGA TTT AAA TAT ATT GAG AAA CAA ATT ATC GAT AGA
Ile Gln Thr Thr Ala Glu Ala Ser Arg Phe Lys Tyr Ile Glu Lys Gln Ile Ile Asp Arg
                160
EcoRI                   700
ATT CAT AAA AAC GAG GTG CCG AGT CTA GCA GCT ATA AGT TTG GAA AAT GAA TGG TCT CTT
Ile His Lys Asn Glu Val Pro Ser Leu Ala Ala Ile Ser Leu Glu Asn Glu Trp Ser Leu
                180                                                     800
CTC TCC AAA CAA ATT CAG ATA GCA AGC TCT AAT AAC GGA AAA TTT CAA ACT CCT GTC AAG
Leu Ser Lys Gln Ile Gln Ile Ala Ser Ser Asn Asn Gly Lys Phe Gln Thr Pro Val Lys
                200                                             850
ATT ATT AAC GAT AAA GGC GTT TCA GTC GAA ATT ACC AAC GTT AGT TCT CTG GTT GTA ACC
Ile Ile Asn Asp Lys Gly Val Ser Val Glu Ile Thr Asn Val Ser Ser Leu Val Val Thr
                220                             900
TCC AAC ATC AAG CTG CTA AAC AAG CAA AAT ATT GCA GCT TTT GAC AAC GAT ATT TCT
Ser Asn Ile Lys Leu Leu Asn Lys Gln Asn Ile Ala Ala Phe Asp Asn Asp Ile Ser
                240
ACA ACG CAC TGAGGCTTGGAGCTACGAGATGCCTTGACTATGGGTATGAAATTAGGTTACGACTCCACTTGAAGA
Thr Thr His
        257
1000                                                    1050
        GTATATGTTGTGTGTTGGGAGTTAATCCACTTGTGGAAATAAGCATGTTCATGTGATCTAACTACGTGAATGCTATG
                        1100                                                    1150
TATGTGTGTTTATTCTTAAATAATAAGTGTGGAGTCTTTTAATCCTTTCAACTTATGCAGATGTGTTGTTCATTG

ATTTTACTAATTAATAAATTAA        1180
```

Fig. 18 (con't)

Fig. 19 clone 3

(a)
```
                                    EcoR I
TTTAAAATATATTGAATAAATATTGTGAGAAAAATGCTTGATATCATAGCTCTCTATAAA
                                                          80
                                          150
ACCATATATTAGATGCTCCATTGGCATCCAAACTACCGAGTGGGAAAG ATG AAT AGA TTC TCA GTG GTT
                                                 Met Asn Arg Phe Ser Val Val
                                                 -23                    -20
```

(b)
```
                                  Sac I                              200
AAT GAT ATC ATC TCT TTG CTA ATT CTC GCC ATA TTC TTT GGA GCT CCA ACT GTC GAA GGC
Asn Asp Ile Ile Ser Leu Leu Ile Leu Ala Ile Phe Phe Gly Ala Pro Thr Val Glu Gly
                  -1                                                          1
                                                  250
TTC AGT ATG GCG AGT GCT GAT TCC AGA TCC TAT AGG AAG ATA CCT AAG TTC ATA ACA TCG CTG AGG AGC
Phe Ser Met Ala Ser Ala Asp Ser Arg Ser Tyr Arg Lys Ile Pro Lys Phe Ile Thr Ser Leu Arg Ser
                                                                              20
                             300
GTT CTC CCA AAA GAT GGA GAA GTG TTC AAG ATA CCT CTA TTG CTT GCC AGT TCT TCA GGC
Val Leu Pro Lys Asp Gly Glu Val Phe Lys Ile Pro Leu Leu Leu Ala Ser Ser Ser Gly
                                                                40
                                                                     Bal I
TCC AGA CGC TAC AAA CTA ATG CAA CTC TCA AAT TAT GAG GAG AAA ACC ATC ACG GTG GCC
Ser Arg Arg Tyr Lys Leu Met Gln Leu Ser Asn Tyr Glu Glu Lys Thr Ile Thr Val Ala
          350                                                60
                                                                             450
ATA GAC GTA ACA AAC GTT ATT ATG GGA TAT ATT GTC CTT GTC AAT ACA TCC TAC TTT TTC
Ile Asp Val Thr Asn Val Ile Met Gly Tyr Ile Val Leu Val Asn Thr Ser Tyr Phe Phe
    400                                                 80
                                                      500
AAT GAG CCT GAT GCT GCT TCT ACA GCT TCT AAA TTT GTA TTC ACA AAT GCT CAG AAG AGT GTT
Asn Glu Pro Asp Ala Ala Ser Thr Ala Ser Lys Phe Val Phe Thr Asn Ala Gln Lys Ser Val
                                                    Phe Val Phe Thr Asn
                                                100
                               Hind III   550                Pst I
ACA CTT CCA TAT TCT GGC AAC TAC GAA AAG CTT CAA ACT GCA GAC AAA AAG AGA GAG
Thr Leu Pro Tyr Ser Gly Asn Tyr Glu Lys Leu Gln Thr Ala Asp Lys Lys Arg Glu
                                                             120
```

```
                                              600
AAA ATT CCA CTT GGA CTC CCA GCA TTG AGC AGT GCC ATT TCC ACC TTG TAT CAT TAT GAC
Lys Ile Pro Leu Gly Leu Pro Ala Leu Ser Ser Ala Ile Ser Thr Leu Tyr His Tyr Asp
                                                                        140
                          650
TCC AAA GCT GCT GCT GCG GCA CTT CTC GTA ATC ATT CAA ACT ACT GCT GAG GCT TCG AGG
Ser Lys Ala Ala Ala Ala Ala Leu Leu Val Ile Ile Gln Thr Thr Ala Glu Ala Ser Arg
                                                                        160
          700                    Xho I                              Apn I    750
TTT AAA TAT ATC GAG CAA CAA ATT CTC GAG AGG CTT AGC GTA GAT GAG GTA CCA AGT CTA
Phe Lys Tyr Ile Glu Gln Gln Ile Leu Glu Arg Leu Ser Val Asp Glu Val Pro Ser Leu
                                                                    180
                                                                        800
GCT ACT ATA AGT TTA GAA AAC AAC TGG TCT CTT TCC AAA CAA ATT CAG TTA GCA CAA
Ala Thr Ile Ser Leu Glu Asn Asn Trp Ser Leu Ser Lys Gln Ile Gln Leu Ala Gln
                                                                    200
         SspI                                       850
ACC AAT AAT GGA ACA TTT ATA TCT CCC ATT ACG ATT ATA GAC AAT ACA GGC CAA CGA GTC
Thr Asn Asn Gly Thr Phe Ile Ser Pro Ile Thr Ile Ile Asp Asn Thr Gly Gln Arg Val
                                                                        220
                                      900
CAA ATA AAC AAC GTT ACT TCA AAC GTA GCC AAA ATC ATG TTG CTA AAC AAA
Gln Ile Asn Asn Val Thr Ser Asn Val Ala Lys Asn Ile Met Leu Leu Asn Lys
                                                                    240
                          950                                                 1000
CAA AAT ATG GCG TAC TAAGACTGAAGGACAACTCCGCTGAAGAACTGTGTGTGTGGAGTTAATCCT
Gln Asn Met Ala Tyr
                249
                                                1050
CCTGTGAAAATAAGCATGTCATGTGACCTAATAACTGTGGAGTCTTTTAATTAATCCTTCAACTTGTACGTATG
                                                            SnaB I
                  1100                              Nde I 1150
TGTTGTTGAGTGATTTACATTTTATTAATTAAGAAAAGAAATGTGAGTTCAACATATGGAACACCTCTAACTT

GTAAA  1169
```

Fig. 19 (con't)

Fig. 20

CLONE 12

(a)
```
                                                                        80
CCAAAAACCATAAACCATGGGTTATCAAAGAAGACCCAAATTATTATCAAAGCCAAAGTTAATATATCTAAAAA
                                                                       160
AACTATTACCTTATAAGAAGCTATTACCTAGAGGCATAAGCTCGTAATTTATTTTGATTAGACTAGAAATACACTA
                                                                       240
ATAGTATGTGGACATAGTCCAGACAACGCTGAATTAGATGGCATACCTCTCTATAAAACCACAGCTTGAGATGCTCCAA
```

(b)
```
     250                    Bcl I
TGGCATCCAAATTCCTCAAGTCGAAAAG ATG ATC AGA TTC TTA GTC TTC TCT TTG CTA ATT CTC ACC
                             Met Ile Arg Phe Leu Val Phe Ser Leu Leu Ile Leu Thr
                             -23                                              300

CTC TTC CTA ACA GCT CCT GCT GTC GAG GGC GAT GTT AGC TTC CGT TTA TCA GGT GCA ACA
Leu Phe Leu Thr Ala Pro Ala Val Glu Gly Asp Val Ser Phe Arg Leu Ser Gly Ala Thr
                                         -1  1                              350

AGC AGT TCC TAT GGA GTT TTC ATT TCA AAT ATG AGA AAA GCT CTT CCA TAT GAA AGG AGA
Ser Ser Ser Tyr Gly Val Phe Ile Ser Asn Met Arg Lys Ala Leu Pro Tyr Glu Arg Arg
                                          20             Nde I

450
CTA TAC GAT ATC TCT CTG TTA CGT TCC ACT CTT CAA GGT TCT CAA CGC TAC GCA TTG ATC
Leu Tyr Asp Ile Ser Leu Leu Arg Ser Thr Leu Gln Gly Ser Gln Arg Tyr Ala Leu Ile
                                          40
                                                          Bcl I
CAT CTC ACA AAT TAC GCC GAT GAA ACC ATT TCA GTG GCC ATA GAC GTA ACG AAC GTC TAT
His Leu Thr Asn Tyr Ala Asp Glu Thr Ile Ser Val Ala Ile Asp Val Thr Asn Val Tyr
                                          60                                600

550
GTT ATG GGA TAT CGC GCT GGT GAT ACA TCC TAT TTT AAC GAG GCT TCT GCA ACT GAA
Val Met Gly Tyr Arg Ala Gly Asp Thr Ser Tyr Phe Asn Glu Ala Ser Ala Thr Glu
                                    80                                 650

GCT GCA AAA TAT GTA TTC AAA GAC GCT CAG CGA AAA GTT ACG CTT CCA TAT TCT GGC AAT
Ala Ala Lys Tyr Val Phe Lys Asp Ala Gln Arg Lys Val Thr Leu Pro Tyr Ser Gly Asn
                             100
```

```
                                                            700
TAC GAA AGG CTT CAA ATT GCA GCA GGC AAA ATA AGG GAA AAT ATT CCG CTT GGA CTA CCT
Tyr Glu Arg Leu Gln Ile Ala Ala Gly Lys Ile Arg Glu Asn Ile Pro Leu Gly Leu Pro
                                    120
                        750
GCT TTG GAC AGT GCC ATT ACC TTC TAC AAT TTG TTT TAC AAC GCC AAT TCT GCT GCG TCG GCA
Ala Leu Asp Ser Ala Ile Thr Phe Tyr Asn Leu Phe Tyr Asn Ala Asn Ser Ala Ala Ser Ala
                                        140
            800
CTT ATG GTA CTC ATT CAG TCG ATG TCT GAG GCG AGG TAT AAA TTT ATT GAG CAA CAA
Leu Met Val Leu Ile Gln Ser Met Ser Glu Ala Arg Tyr Lys Phe Ile Glu Gln Gln
                160
850                                             Sca I 950
ATT GGG AGG CGT GTT GAC AAA ACC TTC CTA CCA AGT CTT GCA ATT ATA ATC AGT AGT TTG GAA AAT
Ile Gly Arg Arg Val Asp Lys Thr Phe Leu Pro Ser Leu Ala Ile Ile Ser Leu Glu Asn
                    180                                 200
                                        1000
AGT TGG TCT GCT CTC TCA AAG CAA ATT ATA AAT GCT CAA GGT CAA CGA GTC ACG ATA ACC AAT GTT GAT GCT
Ser Trp Ser Ala Leu Ser Lys Gln Ile Ile Asn Ala Gln Gly Gln Arg Val Thr Ile Thr Asn Val Asp Ala
                                        220
ACT CCT GTT GTG CTT GTT ATA AAT GCT CAA GGT CAA CGA GTC ACG ATA ACC AAT GTT GAT GCT
Thr Pro Val Val Leu Val Ile Asn Ala Gln Gly Gln Arg Val Thr Ile Thr Asn Val Asp Ala
                                                                                240
                        1050
GGA GTT GTA ACC TCC AAC ATC GCG TTG CTA AAT AGA AAC AAT ATG GCA GTC ATT GAT
Gly Val Val Thr Ser Asn Ile Ala Leu Leu Asn Arg Asn Asn Met Ala Val Ile Asp
                                        240
    1100
GAC CAT GTT CCT GTT CCT ATG GCA CAG AGC TTT GGA AGT TAT GCT ATT TAGTGTAACTTCAAC
Asp His Val Pro Val Pro Met Ala Gln Ser Phe Gly Ser Tyr Ala Ile
SnaB I                              260                 267
CTACGTACGAGTACAAAACTCCCACTGAAGAAT     1185
                            1150
```

Fig. 20 (con't)

```
TAATCCACTGTGTGGAAATAAAGCATGTTCATGTGATATAACTACGTGAATGCTATGTATGTGTTTATTCTTAAA
                                    1200
TAATAAAGTGTGGAGTCTTTAATCCTTCAACTTATGCAGATGTTGTTCATTGATTGTACTAATTAATTAAATTA
AGAA    1239
```

Fig. 20 (con't)

Fig. 21 (con't)

Fig. 22

Fig. 22 (con't)

RECOMBINANT TRICHOSANTHIN AND CODING SEQUENCE

The present application is a continuation-in-part of co-owned U.S. application Ser. No. 07/333,184, filed Apr. 4, 1989 now abandoned, and a continuation-in-part of co-owned U.S. application No. 07/404,326, filed Sept. 7, 1989, U.S. Pat. No. 5,101,025, which is a divisional of 07/333,184, filed Apr. 14, 1989, now abandoned.

FIELD OF THE INVENTION

The present invention relates to recombinantly produced trichosanthin and DNA coding sequences therefore.

REFERENCES

Asano, K., et al., Carlsberg Res Commun, 51:129 (1986).

Barbieri, L., et al., Biochem J, 203:55 (1982).

Bullock, W. O., et al., Biotechniques, 5(4):376 (1987).

Calderwood, S. B., et al., Proc Nat Acad Sci USA, 4364 (1987).

Casellas, P., et al., Eur. J. Biochem. 176:581 (1988).

Chaudhary, V. K., et al., Nature, 335:369 (1988).

Coleman, W. H., et al., Biochem Biophys Acta, 239 (1982).

Crowe, S., et al., Aids Research and Human Retroviruses, 3(2):135 (1987).

Cumber, J. A., et al., Methods in Enzymology, 207 (1985).

Duncan, R. J. S., et al., Anal BioChem, 182:68 (1983).

Falasca, A., et al., Biochem J, 207:505 (1982).

Funatsu, G., et al., Agric Biol Chem, 52(4):1095 (1988).

Gasperi-Campani, et al., FEBS Lett, 76(2):173 (1977).

Grasso, S., et al., Phytopathology, 68:199 (1978).

Gu, Zi-wei, et al., Acta Chemica Sinica, 43:943 (1984).

Habuka, N., et al., J. Biol. Chem. 264:6629 (1989).

Halling, K. C., et al., Nuc Acids Res, 13:8019 (1985).

Hsu, K. J., et al., Acta Zool Sin, 22:149 (1976).

Hwang, Y. N., Chinese J Integrated Trad and Western Medicine, 7:154 (1987).

Irvin, J. D., Arch Biochem Biophys, 169:522 (1975).

Kao, H., et al., Acta Biol Exp Sin, 11:253 (1978).

Kuo-Fen, C., et al., Obs and Gyn, 59(4):494 (1982).

Lamb, F. I., et al., Eur J Biochem, 148:265 (1985).

Law, L. K., et al., J Reprod Fert, 69:597 (1983).

Lifson, J. D., et al., Science, 232:1123 (1986).

Lin, J. Y., et al., Toxicon, 16:653 (1978).

Maddon, P. J., et al., Cell, 42:93 (1985).

Maraganore, J. M., et al., J Biol Chem, 2(24):11628 (1987).

McGrath, M. et al. (1989) Proc. Natl. Acad. Sci. USA 86:2844.

Murray, H. G. et al., Nuc Acids Res, 8:4321 (1980).

Ohtsuka, E., et al., J Biol Chem, 260(5):2605 (1985).

Olsnes, S., Nature, 328:474 (1987).

Olsnes, S., et al., in Molecular Action of Toxins and Viruses, (Elsevier, 1982), Chapter 3.

Pan, K., et al., Scientia Sinica (Series B) (4):386 (1987).

Spreafico, F., et al., Int J Immunopharmoc, (4):335 (1983).

Takahashi, Y., et al., Proc Nat Acad Sci, USA, 1931 (1985).

Taylor, B. et al, BRL Focus, 4(3):4 (1982).

Till, M. A., et al., Science, 242:1166 (1987).

Wang, Yu, et al., Pure & Appl Chem, 58(5):789 (1986).

Xiong, Y. Z., et al., Acta Zool Sin, 11:236 (1976).

Xuejan, Z., et al., Nature, 321:477 (1986).

Yeung, H. W. et al., Int J Peptide Protein Res, 27:325 (1986).

BACKGROUND OF THE INVENTION

Trichosanthin (TCS) is a plant protein which is obtained from the *Trichosanthes kirilowii* root tuber. The protein, which is also known as alpha-trichosanthin (Law) and Radix trichosanthis (Kuo Fen), is a basic, single-chain protein having a molecular weight of about 25,000 daltons. An incorrect protein sequence of TCS has been reported (Gu; Wang), and a molecular model has been derived from X-ray analysis (Pan).

It has been shown that TCS is a potent inhibitor of protein synthesis in a Cell-free lysate system (Maraganore). This activity is consistent with the observed homology in amino acid sequence between TCS and the A chain of ricin, a ribosome-inactivating protein (RIP) which shows amino acid homology with a number of other RIPs, including abrin A chain (Olnes, 1982, 1987) and modeccin (Olsnes, 1982), and various single chain ribosome-inactivating proteins, such as pokeweed antiviral protein (PAP) (Irvin), RIPs from a variety of other plants (Coleman; Grasso; Gasperi-Campani) and the A subunit of Shiga-like toxins from *E. Coli* (Calderwood).

TCS, or plant extracts containing TCS, have been used in China as an abortifacient agent in humans, particularly during midtrimester (14 to 26 weeks). As such, the drug has been administered by intramuscular, intravenous, or intraamniotic routes, typically at a single dose of between about 5–12 mg. The phenomenon of mid-term abortion has been attributed to the selective destruction of placental villi. Other studies indicate that the syncytiotrophoblast is preferentially affected (Hsu; Kao) and that secretion of hCG may be impaired (Xiong). TCS has also been shown to have a suppressive effect on human choriocarcinoma, and the protein appears to be able to pass the blood/brain barrier (Hwang).

It has recently been shown that TCS has a selective inhibitory effect on viral expression in human T cells and macrophages infected with human immunodeficiency virus (HIV). This is evidenced by nearly complete inhibition of HIV-derived antigen in infected cells treated with the protein, as well as selective inhibition of protein and DNA synthesis in the infected cells. Similar results were also discovered for momorcharin, a basic glycoprotein obtained from the seeds of the bitter melon plant (Falosia; Spreafico; Lin; Barbieri). These findings, and applications of the two proteins for the treatment of HIV infection, are detailed in U.S. Pat. No. 4,795,739 for "Method of Selectively Inhibiting HIV".

Particularly in view of the ability of TCS to inhibit viral expression in HIV-infected human T cells and macrophages, it would be desirable to produce a relatively pure, invariant preparation of TCS, for use as a human therapeutic agent. Methods of preparing TCS from the roots of *T. kirilowii* have been reported (Yueng). Analysis of the purified TCS produced by earlier disclosed known methods indicates that the protein is only partially purified, and in particular, contains hemagglutinating contaminant protein(s). A more recent purification method described in co-owned patent application for "Purified Trichosanthin and Method of Purification", U.S. application No. 07/333,181, filed 4 Apr. 1989, yields a highly purified TCS preparation which is substantially free of protein contaminants, including hemagglutinating proteins.

Additionally, it would be desirable to produce TCS by means of recombinant DNA technology. Synthesis of the protein by recombinant methods would avoid the difficulty of obtaining *T. kirilowii* roots in fresh form, since at present the tuber roots are available only from Certain regions of the Orient. Recombinant production of TCS would also avoid the problem of variations in primary amino acid sequence in TCS obtained from natural root material from different geographic areas.

Recombinant production of TCS would also facilitate the production of peptide derivatives of TCS, including bioactive peptide portions of TCS, and bioactive portions of the protein fused with functional peptides which confer, for example, enhanced targetcell specificity.

SUMMARY OF THE INVENTION

It is therefore one object of the present invention to provide a recombinant TCS protein capable of selectively inhibiting viral expression in HIV-infected human T cells or macrophages.

It is a related object of the invention to provide the coding sequence for TCS from *T. kirilowii.*

Still another object of the invention is to provide sets of degenerate primers corresponding to spaced amino acid regions of TCS which are homologous to spaced amino acid regions of RIPs, for use in selectively amplifying plant derived genomic sequences which code for such RIPs.

In one aspect, the invention includes a cloned nucleic acid molecule which encodes a trichosanthin protein having the functional properties of Trichosanthes-obtained trichosanthin. The nucleic acid molecule is included in the sequence:

The nucleic acid of the invention may include:
(a) basepairs 409 to 1149 which encodes mature TCS from *T. kirilowii,;*
(b) in addition to (a), basepairs 340-408, which encodes an amino terminal extension of the mature form of TCS from *T. kirilowii;*
(c) in addition to (a), basepairs 1150 to 1206 which encodes a carboxy terminal extension of the mature form of TCS from *T. kirilowii;* and
(d) a TCS coding sequence joined with a ligand peptide coding sequence, encoding a fused protein having a ligand peptide which confers cell-surface recognition properties on the fused protein.

The invention also includes the coding sequence for TCS from *T. kirilowii* in combination with an expression vector. One preferred expression vector construction contains a promoter, a ribosome binding site, an ATG start codon positioned adjacent the amino-terminal codon of TCS, and a stop codon positioned adjacent the carboxy terminal codon of mature TCS.

In another aspect, the invention includes a primer mixture for use in selectively amplifying a genomic fragment coding for first and second spaced regions of TCS from *T. kirilowii* DNA, by repeated primer-initiated strand extension. The primer mixture includes a first set of sense-strand degenerate primers, and a second set of anti-sense primers, where each set contains substantially all of the possible coding sequences corresponding to the first and second region of known trichosanthin amino acid sequence, respectively. That is, each degenerate primer set includes at least one primer species which is effective to hybridize with the coding sequence of the corresponding amino acid region.

In a preferred embodiment, the primers in the first and second primer sets are designed to hybridize to first and second coding regions, respectively, which encode TCS amino acid sequences that are homologous in amino acid sequences to first and second amino-acid sequences in a variety of RIPs, such as ricin A chain,

```
        Eco R1
1    GAATTCAAATATTTTCTGAATAAATATAAAATTCATTGTAGAGAAATGATGAGAA                          55
56   AACAAGAACAATTTTCAAAAACAAAAAATAAAAAACAAATGGTTTATCAAAGAAG                          110
111  GCCCGAATTTATTATCAAAAGCGAAAGTTAATAATATCTAAAAAAAAAACTATT                           163
164  ACCTTATAAGAAGCTATTACCTAGATGGCATAAGATCATACTTTTATTTTTGATT                          218
219  TAGACTAGAAATACACTAATATATTGTGGACATAGCCAGACAACGATTAGATGGC                          273
274  ATACCTCTCTATAAAAACCACAGCTTGAGATGCTCCAATGGCATCCAAATTCCTC                          328
329  AAGTCAAAAAG      ATG  ATC  AGA  TTC  TTA  GTC  CTC  TCT  TTG  CTA  ATT          372
373  CTC  ACC  CTC  TTC  CTA  ACA  ACT  CCT  GCT  GTG  GAG  GGC  GAT  GTT           414
415  AGC  TTC  CGT  TTA  TCA  GGT  GCA  ACA  AGC  AGT  TCC  TAT  GGA  GTT           456
457  TTC  ATT  TCA  AAT  CTG  AGA  AAA  GCT  CTT  CCA  AAT  GAA  AGG  AAA           498
499  CTG  TAC  GAT  ATC  CCT  CTG  TTA  CGT  TCC  TCT  CTT  CCA  GGT  TCT           540
541  CAA  CGC  TAC  GCA  TTG  ATC  CAT  CTC  ACA  AAT  TAC  GCC  GAT  GAA           582
583  ACC  ATT  TCA  GTG  GCC  ATA  GAC  GTA  ACG  AAC  GTC  TAT  ATT  ATG           624
625  GGA  TAT  CGC  GCT  GGC  GAT  ACA  TCC  TAT  TTT  TTC  AAC  GAG  GCT           666
667  TCT  GCA  ACA  GAA  GCT  GCA  AAA  TAT  GTA  TTC  AAA  GAC  GCT  ATG           708
709  CGA  AAA  GTT  ACG  CTT  CCA  TAT  TCT  GGC  AAT  TAC  GAA  AGG  CTT           750
752  CAA  ACT  GCT  GCG  GCC  AAA  ATA  AGG  GAA  AAT  ATT  CCG  CTT  GGA           792
793  CTC  CCA  GCT  TTG  GAC  AGT  GCC  ATT  ACC  ACT  TTG  TTT  TAC  TAC           834
835  AAC  GCC  AAT  TCT  GCT  GCG  TCG  GCA  CTT  ATG  GTA  CTC  ATT  CAG           876
877  TCG  ACG  TCT  GAG  GCT  GCG  AGG  TAT  AAA  TTT  ATT  GAG  CAA  CAA           918
919  ATT  GGG  AAG  CGC  GTT  GAC  AAA  ACC  TTC  CTA  CCA  AGT  TTA  GCA           960
962  ATT  ATA  AGT  TTG  GAA  AAT  AGT  TGG  TCT  GCT  CTC  TCC  AAG  CAA           1002
1003 ATT  CAG  ATA  GCG  AGT  ACT  AAT  AAT  GGA  CAG  TTT  GAA  ACT  CCT           1044
1045 GTT  GTG  CTT  ATA  AAT  GCT  CAA  AAC  CAA  CGA  GTC  ATG  ATA  ACC           1086
1087 AAT  GTT  GAT  GCT  GGA  GTT  GTA  ACC  TCC  AAC  ATC  GCG  TTG  CTG           1128
1129 CTG  AAT  CGA  AAC  AAT  ATG  GCA  GCC  ATG  GAT  GAC  GAT  GTT  CCT           1170
1171 ATG  ACA  CAG  AGC  TTT  GGA  TGT  GGA  AGT  TAT  GCT  ATT  TAG  TGT           1212
1213 AAC  TTC  AAG  CTA  CGT                                                        1227
``` where basepairs 409 to 1149 encode the mature form of TCS isolated from *Trichosanthes kirilowii.* abrin A chain, pokeweed antiviral protein, and barley ribosome inhibitor. The two primer sets may be used to obtain genomic coding sequences for the corresponding RIPs, by repeated primer-initiated strand extension.

Also forming a part of the invention is a recombinant trichosanthin protein having the functional properties of mature trichosanthin (a) derived from *T. kirilowii* and (b) having the sequence:

| Asp | Val | Ser | Phe | Arg | Leu | Ser | Gly | Ala | Thr | Ser | Ser | Ser | Tyr | Gly | Val |
|---|---|---|---|---|---|---|---|---|---|---|---|---|---|---|---|
| Phe | Ile | Ser | Asn | Leu | Arg | Lys | Ala | Leu | Pro | Asn | Glu | Arg | Lys | Leu | Tyr |
| Asp | Ile | Pro | Leu | Leu | Arg | Ser | Ser | Leu | Pro | Gly | Ser | Gln | Arg | Tyr | Ala |
| Leu | Ile | His | Leu | Thr | Asn | Tyr | Ala | Asp | Glu | Thr | Ile | Ser | Val | Ala | Ile |
| Asp | Val | Thr | Asn | Val | Tyr | Ile | Met | Gly | Tyr | Arg | Ala | Gly | Asp | Thr | Ser |
| Tyr | Phe | Phe | Asn | Glu | Ala | Ser | Ala | Thr | Glu | Ala | Ala | Lys | Tyr | Val | Phe |
| Lys | Asp | Ala | Met | Arg | Lys | Val | Thr | Leu | Pro | Tyr | Ser | Gly | Asn | Tyr | Glu |
| Arg | Leu | Gln | Thr | Ala | Ala | Gly | Lys | Ile | Arg | Glu | Asn | Ile | Pro | Leu | Gly |
| Leu | Pro | Ala | Leu | Asp | Ser | Ala | Ile | Thr | Thr | Leu | Phe | Tyr | Tyr | Asn | Ala |
| Asn | Ser | Ala | Ala | Ser | Ala | Leu | Met | Val | Leu | Ile | Gln | Ser | Thr | Ser | Glu |
| Ala | Ala | Arg | Tyr | Lys | Phe | Ile | Glu | Gln | Gln | Ile | Gly | Lys | Arg | Val | Asp |
| Lys | Thr | Phe | Leu | Pro | Ser | Leu | Ala | Ile | Ile | Ser | Leu | Glu | Asn | Ser | Trp |
| Ser | Ala | Leu | Ser | Lys | Gln | Ile | Gln | Ile | Ala | Ser | Thr | Asn | Asn | Gly | Gln |
| Phe | Glu | Thr | Pro | Val | Val | Leu | Ile | Asn | Ala | Gln | Asn | Gln | Arg | Val | Met |
| Ile | Thr | Asn | Val | Asp | Ala | Gly | Val | Val | Thr | Ser | Asn | Ile | Ala | Leu | Leu |
| Leu | Asn | Arg | Asn | Asn | Met | Ala | | | | | | | | | |

The recombinant TCS protein may further include an amino-terminal extension having the sequence:

Met Ile Arg Phe Leu Val Leu Ser Leu Leu Ile Leu Thr Leu Phe Leu Thr Thr Pro Ala Val GluGly;

and/or a carboxy-terminal extension having the sequence:

Ala Met Asp Asp Asp Val Pro Met Thr Gln Ser Phe Gly Cys Gly Ser Tyr Ala Ile.

The invention further includes a recombinant process for the production of a trichosanthin protein having the functional properties of Trichosanthes-obtained TCS. This recombinant process involves inserting a DNA sequence encoding the TCS protein into an expression vector, transforming a suitable host with the vector, and isolating the recombinant protein expressed by the vector.

The invention further comprises nucleic acid and protein coding sequences for several unique members of the ribosome-inactivating-protein multi-gene family of *Trichosanthes kirilowii*.

These and other objects and features of the invention will become more fully apparent when the following detailed description of the invention is read in conjunction with the accompanying drawings.

BRIEF DESCRIPTION OF THE DRAWINGS

FIG. 1 shows the amino acid sequence of mature TCS isolated from *T. kirilowii* as determined herein (upper line) and as reported previously (lower line);

FIGS. 3A and 3B show the DNA sequence from an amplified genomic fragment containing a portion of the TCS coding sequence, and the corresponding amino acid sequences in the three possible reading frames in both directions;

FIG. 4 shows the nucleotide sequence of the TCS coding region from *T. kirilowii* and adjacent 5'- and 3'-end sequences;

FIG. 9 compares the amino acid sequence of TCS with those of exemplary RIPs.

FIG. 11 illustrates the synthetic gene designed for expression of TCS. The bold restriction sites are those flanking the individual synthetic fragments as overlapping sticky ends; for example, KpnI-HindIII, HindIII-NsiI, etc.

FIG. 12A shows the correct orientation of the polylinkers in the construction of pPS200; FIG. 12B the incorrect orientation.

FIG. 16 shows the nucleic acid sequence of the cloned insert of pQ30E and corresponding protein coding sequence.

FIG. 17 shows the nucleic acid sequence of cloned insert of pQ24 and the corresponding protein coding sequence.

FIG. 18 shows the nucleic acid sequence of cloned insert of pQ2 and the corresponding protein coding sequence.

FIG. 19 shows the nucleic acid sequence of cloned insert of pQ3 and the corresponding protein coding sequence. FIG. 20 shows the nucleic acid sequence of cloned insert of pQ12 and the corresponding protein coding sequence.

FIG. 21 shows an alignment of protein sequences corresponding to the nucleic acid sequences of cloned inserts of pQ2, pQ3, pQ12, and of pQ21D and pQ30E.

FIG. 22 shows an alignment similar to FIG. 21 where the protein coding sequence corresponding to the nucleic acid sequence of cloned insert 2 is used as a standard sequence and amino acid substitutions representing the other protein coding sequences are listed in vertical columns for each amino acid residue—the hyphens act as space holders to allow easier alignment and an asterick indicates a site where omission of an amino acid is possible.

DETAILED DESCRIPTION OF THE INVENTION

I. Definitions

The terms below have the following meanings as used herein:

A "trichosanthin protein" is a protein having at least about 90% amino acid sequence identity with alphatrichosanthin obtained from *T. kirilowwii*.

A trichosanthin protein has the functional properties of Trichosanthes-obtained trichosanthin if it has (a) the ability to selectively inhibit expression of HIV-antigen in HIV-infected T-cells or monocyte/macrophages, and/or (b) protein-synthesis-inhibitory activity.

II. Producing Recombinant TCS

This section describes methods for obtaining a genomic region containing the coding sequence for TCS from *T. kirilowii*, and for expressing mature TCS protein in a bacterial expression system.

A. TCS Amino Acid Sequence

TCS was purified by a novel method which is detailed in co-owned patent application for "Purified Trichosanthin and Method of Purification", U.S. application Ser. No. 07/333,181, filed 4 Apr. 1989, and outlined in Example 1. The protein was at least about 98% pure as judged by HPLC and gel electrophoresis analysis.

The primary amino acid sequence of the purified trichosanthin was determined under contract with the Protein Chemistry Services at Yale University School of Medicine. The sequence is shown in FIG. 1 (upper line) along with the previously published sequence (lower line) of TCS (Gu; Wang). Variations between the two sequences are noted by double underlining.

As seen from FIG. 1, the present sequence differs substantially from the published sequence. Most significant, as compared to the published sequence, the present TCS sequence lacks a block of 10 amino acids at position number 69 and contains an additional sequence of 21 amino acids at position number 222. The present sequence agrees closely with X-ray diffraction data on crystalized TCS, and resolves inconsistancies between X-ray diffraction data and the previously published TCS sequence. The new sequence, particularly including the 21-amino acid addition, also provides greater sequence homology with a number of RIPS, such as ricin A chain and abrin A chain (see below) than the earlier published sequence.

B. TCS Coding Sequence

Figure 2:
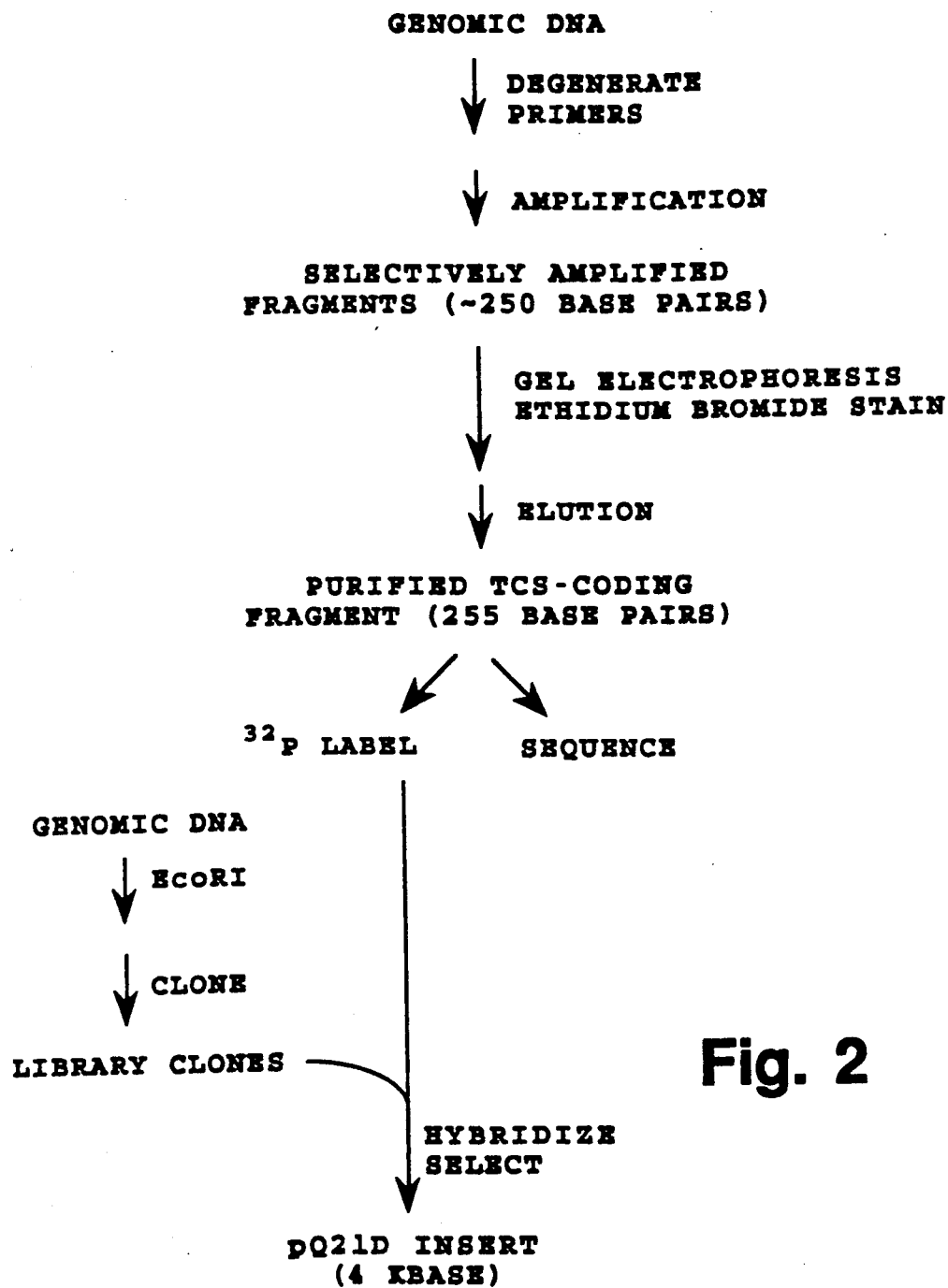
FIG. 2 illustrates the steps in the method used to obtain cloned TCS coding sequences.

FIG. 2 outlines the steps described below for obtaining the complete coding sequence of TCS from *T. kirilowii*. The actual procedure used is given in Example 2.

With reference to the figure, genomic DNA isolated from *T. kirilowii* is mixed with at least two sets of degenerate primers in a reaction mixture designed for carrying out selective amplification of a TCS coding sequence.

In preparing the sets of degenerate primers, two spaced amino acid regions of TCS were selected for coding sequence targeting. The two amino acid sequences which were selected are overlined in FIG. 1 and relate to a 35-mer degenerate primer for the sequence denoted A and to a 32-mer degenerate primer for the sequence denoted B.

Each set of degenerate primers were designed such that at least one primer sequence is effective to hybridize with the DNA sequence coding for the corresponding amino acid sequence. Deoxyinosine nucleotides were incorporated in order to generate probes longer than 20 nucleotides of manageable complexity (Ohtsuka; Takahashi). One of the two primer sets is designed for hybridization with the anti-sense strand of one coding region, and the other primer set, for hybridization with the sense strand of the second coding region.

The primer set corresponding to the 35-mer includes 128 isomers and is of the general sequence:

5'-GA(A,G)GCIGCIAA(A,G)TA(C,T)GTITT(C,T)AA(A,G)GA(C,T)GCIATG(A,C)G -3' where bases placed in parantheses indicate a mixture and I is inosine. This set is designated MPQP-1, and was designed for binding to the anti-sense strand of the TCS coding region. The other two primer sets, designated MPQP-2 and MPQP-3, each consist of 128 isomers and together comprise all potential coding sequences of the 32-mer and are of the general sequences:

5'-CG(C,T)TTICCIAT(C,T)TG(C,T)TG(C,T)TCIAT(A,G)AA(C,T)TT(A,G)TA -3' and
5'-CT(C,T)TTICCIAT(C,T)TG(C,T)TG(C,T)TCIAT(A,G)AA(C,T)TT(A,G)TA -3', respectively. They were designed for binding to the sense strand of the TCS coding region, and were typically used in a primer mixture designed MPQP-2/-3.

A DNA amplification reaction was carried out by repeated primer initiated strand extension, using a commercially supplied kit (Perkin-Elmer/Cetus) and according to methods supplied by the manufacturer as outlined in Example 2. The product of the DNA amplification step was isolated by agarose gel electrophoresis, and by polyacrylamide gel electrophoresis, with detection by ethidium bromide fluorescence and/or autoradiography. A major product of about 255 base pairs was detected.

FIGS. 3A and 3B show the DNA sequence of the amplified material, and the amino acid sequences corresponding to all three reading frames in both directions. The underlined translation shows a sequence that is homolgous to amino acids 128 through 163 in TCS.

This sequence is within the region predicted to be amplified and confirmed that a TCS or TCS-like coding region was amplified.

Southern blot analyses were performed on the DNA prepared from the plant tissue to assess the organization and the complexity of TCS genes in the total DNA background. The Southern blots were probed separately with $^{32}$P-labelled MPQP-1 and MPQP-2/-3. The results (not shown) suggested that there might be several TCS-related genes, and that the overall complexity of the plant genome is on the order of a mammalian genome and could be effectively screened using standard lambda-phage banks.

With continued reference to the method outlined in FIG. 2, the amplified coding sequence from above was used as a probe to identify one or more *T. kirilowii* genomic library clones containing TCS coding sequences. The genomic library clones were prepared and probed conventionally, as outlined in Example 2. Two clearly positive plaques were picked, amplified and converted to plasmids, according to protocols supplied by the manufacturer of the cloning system. One clone, designated pQ21D, contained an approximate 4kb insert; the other, designated pQ30E, contained an approximate 0.6 kb insert. The pQ21D vector has been deposited with The American Type Culture Collection, 12301 Parklawn Drive, Rockville, Md., 20852, and is identified by ATCC No. 67907. Partial sequence analysis showed that the 4 kb insert contained sequences that coded for a protein having substantially the same amino acid sequence shown for plant-derived TCS in FIG. 1. The 0.6 kb insert was found to contain sequences encoding a peptide homologous to, but not identical with, plant-derived TCS.

The complete sequence for the insert of pQ21D was determined and is shown in FIG. 4, along with the corresponding amino acid sequence of TCS. As seen in the figure, the sequence encodes a protein that contains a continuous amino acid sequence identical to that of plant-derived TCS except for two conservative changes—a Thr for a Ser substitution at amino acid position 211 and a Met for a Thr substitution at position 224.

The minor differences between the two sequences are presumably related to variations between different *T. kirilowii* strains. The purified TCS was obtained from *T. kirilowii* roots from the Canton region of China; the genomic DNA was obtained from *T. kirilowii* leaves from Korea.

These conservative sequence variations illustrate strain-related DNA sequence variations which result in functionally equivalent trichosanthin proteins.

A comparison of the amino acid sequence of mature plant-derived TCS (FIG. 1) and that encoded by the DNA in FIG. 4 shows that TCS is likely produced as a secreted protein that undergoes post-translational processing at both the amino and carboxy ends. Specifically, nucleotides 340 through 408 code for a putative secretory signal peptide having the sequence:

Met Ile Arg Phe Leu Val Leu Ser Leu Leu Ile Leu Thr Leu Phe Leu Thr Thr Pro Ala Val Glu Gly.

Figure 10:
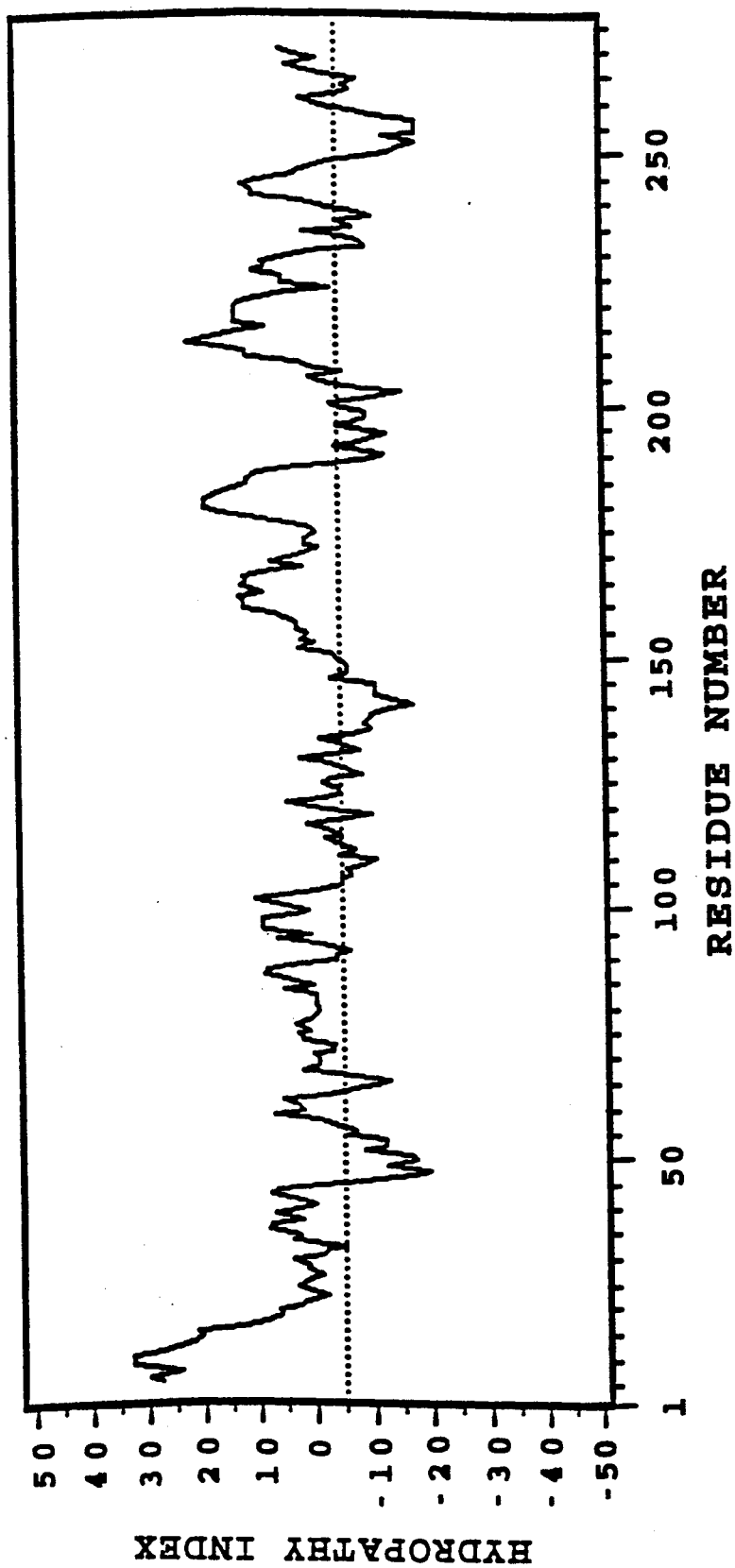
FIG. 10 shows a hydropathy index computation for the entire coding sequence of trichosanthin including: the amino-terminal extension, the sequence encoding the mature protein, and the carboxy-terminal extension.
Figure 13:
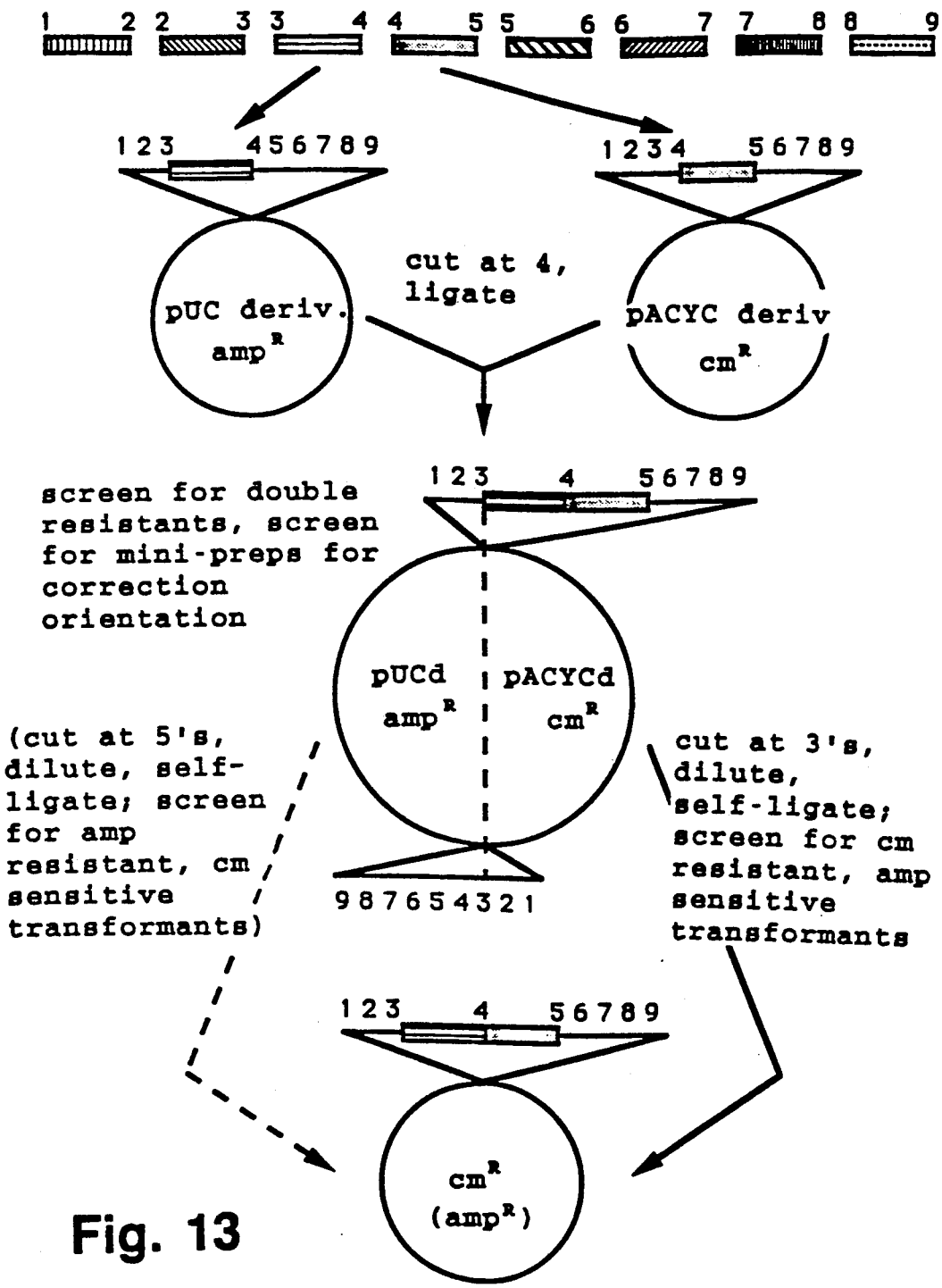
FIG. 13 outlines a generalized schematic diagram of the method used for the condensation of cloned synthetic gene fragments to form a complete synthetic gene.

As can be seen from FIG. 10 (Example 5), these first 23 amino acids of the trichosanthin coding sequence have the characteristic hydrophobicity of a secretory signal. Accordingly, the nucleic acids encoding this sequence will be useful when expressing trichosanthin proteins in plants cell since the sequence will provide a homologous secretory signal. Further, recombinant trichosanthin proteins produced in heterologous expression systems, which retain the 5' leader sequence, can be used as a substrate in assays to identify the leader sequence processing enzyme activity. The 23 amino acid sequence itself can be used as an antigen to generate antibodies to examine, for example, the steps of in vivo protein processing in plant cells.

Nucleotides 1150 through 1206 code for a putative carboxy terminal extension that is not present in the mature protein, and which has the sequence:

Ala Met Asp Asp Asp Val Pro Met Thr Gln Ser Phe Gly Cys Gly Ser Tyr Ala Ile.

As mentioned above for the amino-terminal extension, the carboxy-terminal extension will also be useful for expression of the trichosanthin protein in plant cells. Although the role of the carboxy-terminal extension has not yet been determined, it is possible that this peptide functions to neutralize the ribosome inhibiting activity of the peptide prior to cellular secretion: trichosanthin proteins retaining this sequence, or variations of this sequence, will be useful in specifically defining the function of this protein extension. Also, the carboxy-terminal sequence itself can be used as an antigen to generate antibodies to examine, for example, the steps of in vivo protein maturation in plant cells.

According to one aspect, the invention includes a nucleic acid which encodes for a trichosanthin protein which has the functional properties of Trichosanthes-obtained TCS. The nucleic acid preferably has the sequence shown in FIG. 4, where basepairs 409–1149 of the sequence code for mature TCS from *T. kirilowii*. The nucleic acid of the invention may include:

(a) basepairs 409 to 1149 which encodes mature trichosanthin from *T. kirilowii*;
(b) in addition to (a), basepairs 340–408, which encodes a putative amino terminal extension of the mature form of trichosanthin from *T. kirilowii*;
(c) in addition to (a), basepairs 1150 to 1206 which encodes a putative carboxy terminal extension of the mature form of trichosanthin from *T. kirilowii*; and
(d) a TCS coding sequence joined with a ligand coding sequence, encoding a fused protein having a ligand peptide which confers cell-surface recognition properties on the fused protein.

C. Expressing Recombinant TCS Protein

Figure 5:
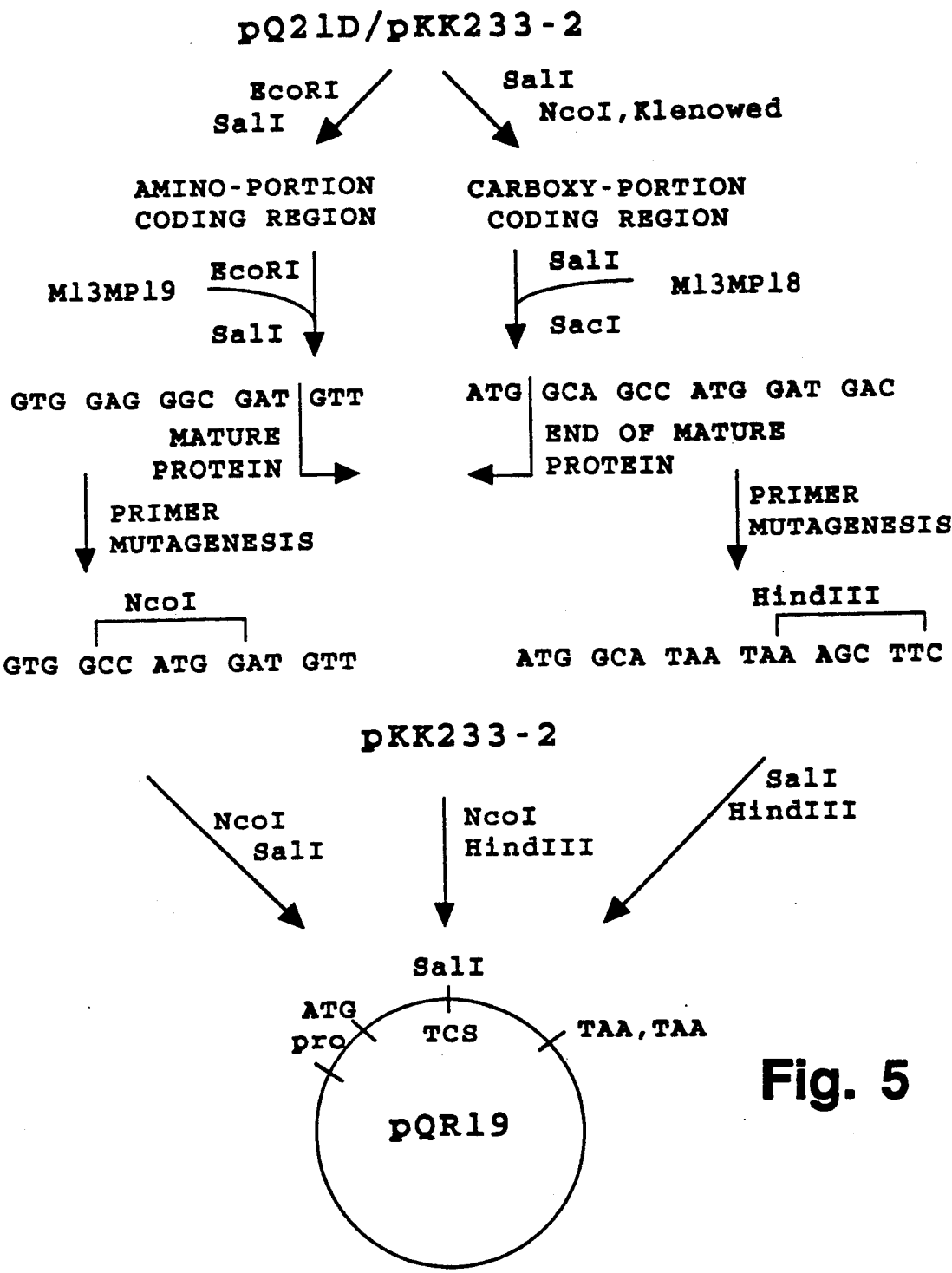
FIG. 5 illustrates the steps in the method used to express mature TCS in a bacterial system.

Recombinant TCS was produced using the above TCS coding sequence, following the steps outlined in FIGS. 4 and 5, and described in Example 5. With reference to FIG. 5, plasmid pQ21D from above was digested with EcoRI and NcoI, releasing a 1.2 kb fragment insert containing the complete coding sequence for TCS. This TCS-coding fragment was cloned into plasmid pKK233-2 which was previously digested with EcoRI and NcoI. After replication the recombinant plasmid, designated pQ21D/pKK233-2, was divided into two samples. One sample was digested with EcoRI and SalI, and and the second sample with SalI and NcoI to generate an EcoRI/SalI amino portion fragment and a SalI/NcoI carboxy portion fragment. The two fragments were cloned into M13 phage vectors for site specific mutagenesis, to place a NcoI site containing an ATG start codon at the amino terminal end of the mature TCS coding sequence, and a double TAA translation stop sequence plus a HindIII cloning site after the carboxy end of the mature sequence, as illustrated in FIG. 5.

The modified sequences were excised from the mutagenized clones, and cloned together into a pKK233-2 expression vector (Pharmacia) which contains a synthetic trp/lac promoter positioned appropriately ahead of a ribosome binding site that is also positioned appropriately ahead of an ATG start codon contained within an NcoI site. Several clones were characterized and verified to contain the modified insert in the correct orientation. The DNA sequences of the modified regions were directly verified for one clone, designated pQR19.

More generally, the pQR19 expression vector is exemplary of a TCS coding sequence operatively placed in an expression vector for TCS expression in a suitable host. In a preferred embodiment, and as exemplified by pQR19, the expression vector construction contains a promoter, a ribosome binding site, and an ATG start codon positioned before and adjacent the amino terminal codon of mature TCS, and a stop codon positioned after and adjacent at the carboxy terminal codon of mature TCS.

For expression of recombinant TCS (rTCS), plasmid pQR19 and similar clones were propagated in an appropriate E. coli host strain that carries a lacIq gene for regulation of the synthetic trp-lac promoter. The host strain XL-1 Blue (Bullock) was employed. Its relevant genotype is recA1, endA1, gyrA96, thi, hsdR17 (rk-, mk+), supE44, relA1, λ-, lac-[F', proAB, lacIqZΔM15, Tn10 (tet$^R$)]. Induction of promoter activity may be achieved by adding 5 mM IPTG (isopropylthiogalactoside). Under culture conditions described in Example 3, cells carrying pQR19 and similar plasmids were induced and, at a selected cell density, the cells were harvested and disrupted by sonication. Aliquots of total cell material, of material pelleted at 15,000×g for 5 min, and of material remaining in solution at 15,000×g for 5 min were analyzed by polyacrylamide gel electrophoresis and subsequently by Western blot analysis. The Western blot was probed with rabbit anti-TCS sera.

The results showed an immunoreactive product that comigrated with authentic TCS in the total cell and soluble cell fractions from pQR19/XL1-blue induced cells, but not in the insoluble fraction from the same cells, nor in any fraction from pKK233-2(vector)/XL1-blue induced cells, i.e., cells containing the pKK233 expression vector without the TCS coding insert.

The pQR19 expression vector which contains the TCS coding sequence, and which expresses rTCS in a suitable bacterial host has been deposited with The American Type Culture Collection and is identified by ATCC No. 67908.

Clarified cell extract material was fractionated using the steps described in Example 1, yielding rTCS with a purity, as judged by gel band staining with Coomassie blue on SDS polyacrylamide gels, of greater than 90%. About 9 mg of purified rTCS were obtained from nine liters of culture.

The rTCS protein produced is exemplary of an rTCS protein derived from the amino acid sequence shown in FIG. 4. More generally, the rTCS protein of the invention includes a recombinant protein containing the entire amino acid sequence for mature TCS, as described above, and a recombinant TCS protein containing an amino-terminal extension having the sequence:

Met Ile Arg Phe Leu Val Leu Ser Leu Leu Ile Leu Thr Leu Phe Leu Thr Thr Pro Ala Val GluGly;

and/or a carboxy-terminal extension having the sequence:

Ala Met Asp Asp Asp Val Pro Met Thr Gln Ser Phe Gly Cys Gly Ser Tyr Ala Ile.

The invention thus further includes a recombinant process for the production of a trichosanthin protein having the functional properties of Trichosanthes-obtained trichosanthin. The method includes the steps of inserting a DNA sequence encoding said protein into an expression vector, transforming a suitable host with the vector, and isolating the recombinant protein expressed by the vector.

In one preferred embodiment, the expression vector is pQR19 and the host is E. coli.

D. Bioactivity of Recombinant TCS

As previously described in above-cited U.S. Pat. No. 4,795,739, TCS obtained from T. kirilowii is a potent and selective inhibitor of HIV antigen expression in HIV-infected T cells and monocyte/macrophages. The inhibitory effect of rTCS on expression of HIV-specific antigens in HIV-infected T cells can be demonstrated as follows. Acutely HIV-infected human T cells were treated with varying concentrations of rTCS. After four days culture, the amount of HIV p24 antigen present in cell free culture supernatants was quantitated using a commercially available antigen capture immunoassay (Coulter). Inhibition was determined by comparison of results for treated cultures and untreated cultures.

Figure 6:
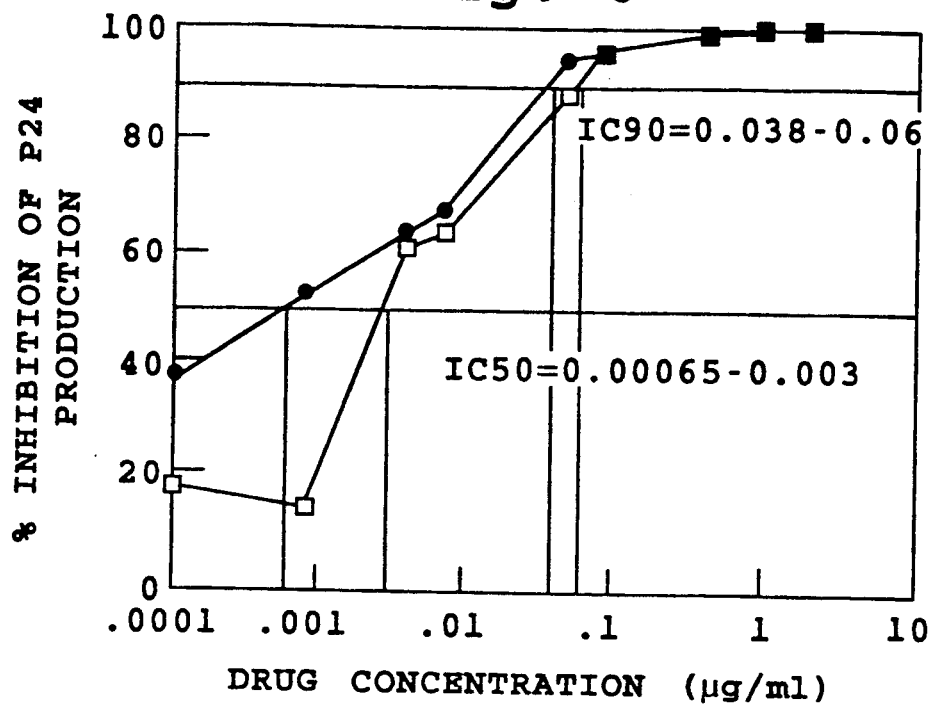
FIG. 6 shows plots of percent inhibition of HIV antigen (p24) production as a function of culture concentration of plant-derived TCS (closed boxes) and rTCS (open boxes)

The viral inhibition studies detailed in Example 4A compared the inhibitory activity of plant-produced TCS with the above rTCS protein. The plots in FIG. 6 show percent inhibition of p24 HIV antigen production as a function of culture concentration of plant derived TCS (closed boxes) and rTCS produced as above (open boxes). As seen, both proteins gave substantially the same level of inhibition at higher protein concentrations, although the plant-derived protein was more effective at the lowest protein concentrations.

Figure 7:
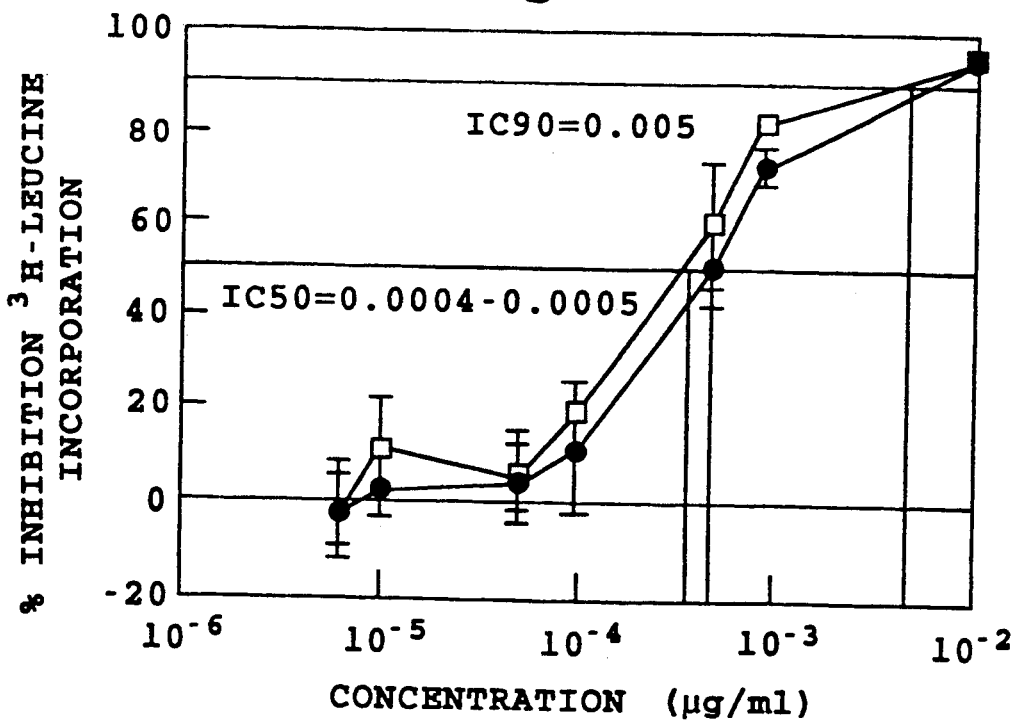
FIG. 7 shows plots of percent inhibition of $^3$H-leucine incorporation into trichloroacetic acid precipitable protein as a function of concentration of plant derived TCS (closed boxes) and rTCS (open boxes) in a cell free rabbit reticulocyte lysate protein synthesizing system.

Also, as mentioned above, it has been shown that plantproduced TCS is a potent inhibitor of protein synthesis in a cell-free lysate system. The protein-synthesis inhibitory properties of both plant-produced TCS and rTCS were compared in a rabbit reticulocyte lysate system, as outlined in Example 4B. The plots in FIG. 7 show percent inhibition of $^3$H-leucine incorporation as a function of concentration of plant-derived TCS (closed boxes) and rTCS (open boxes) in the rabbit reticulocyte system. The plots show that both plant-produced and recombinant TCS have substantially the same specific protein synthesis inhibitory activity.

E. Structure-function studies of α-trichosanthin through manipulation of a synthetic gene.

Figure 14:
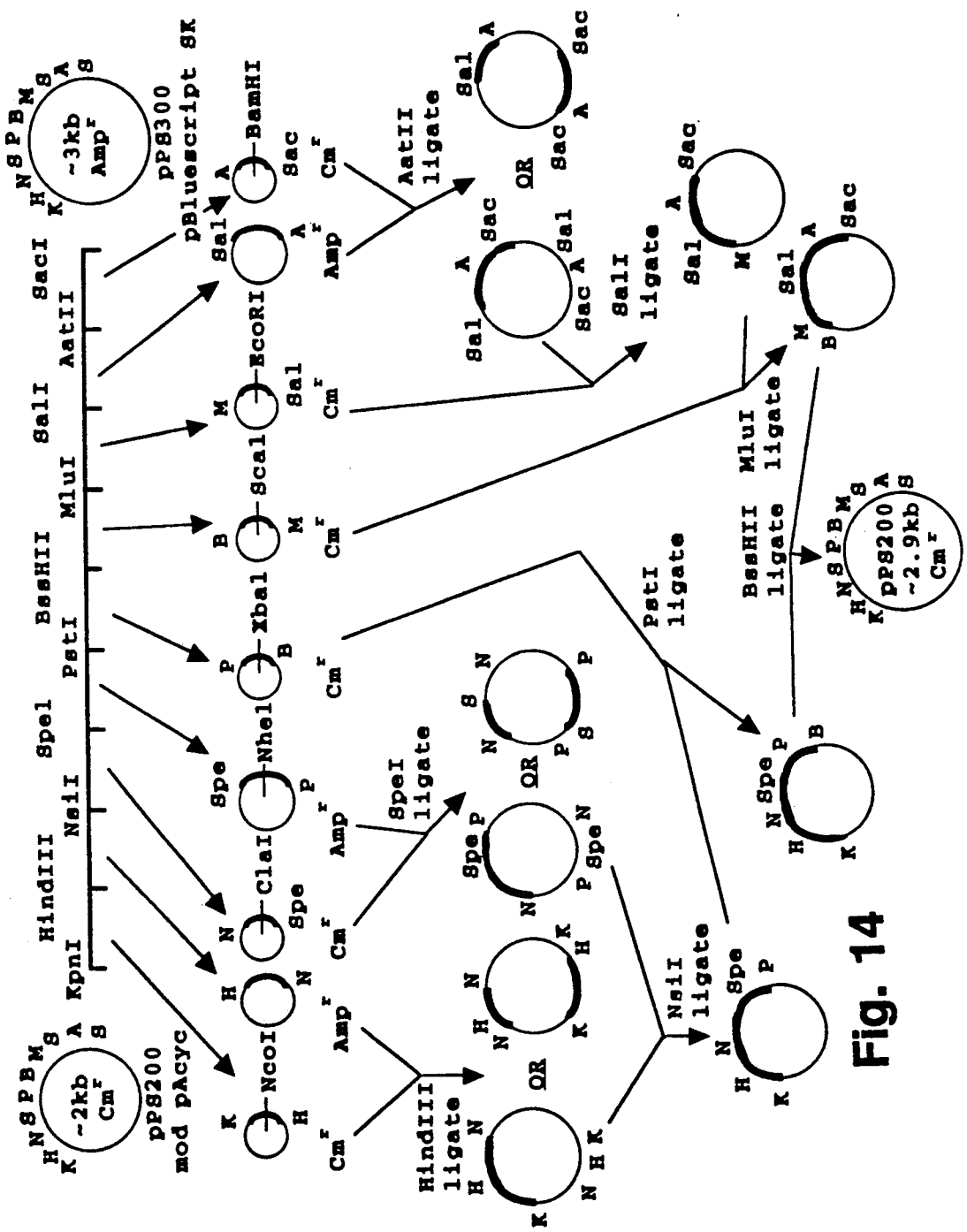
FIG. 14 shows a schematic of the steps taken to clone and condense the synthetic gene for α-trichosanthin.

A synthetic gene for α-TCS has been constructed (Example 6, FIG. 14) to facilitate mutational analyses of α-TCS, aimed at elucidating structure-function relationships, and to better understanding the α-TCS mechanism of action in blocking HIV replication. The synthetic gene contains unique restriction sites spaced 20 to 90 bp apart (FIG. 11), thus allowing convenient introduction of mutations by cassette replacement. The nucleic acid sequence for the synthetic gene was created by assigning nucleic acid codons corresponding to the primary amino acid sequence of the mature α-trichosanthin protein sequence. Accordingly, the translation product of the synthetic gene corresponds to the mature α-trichosanthin (α-TCS) protein sequence.

Figure 9:
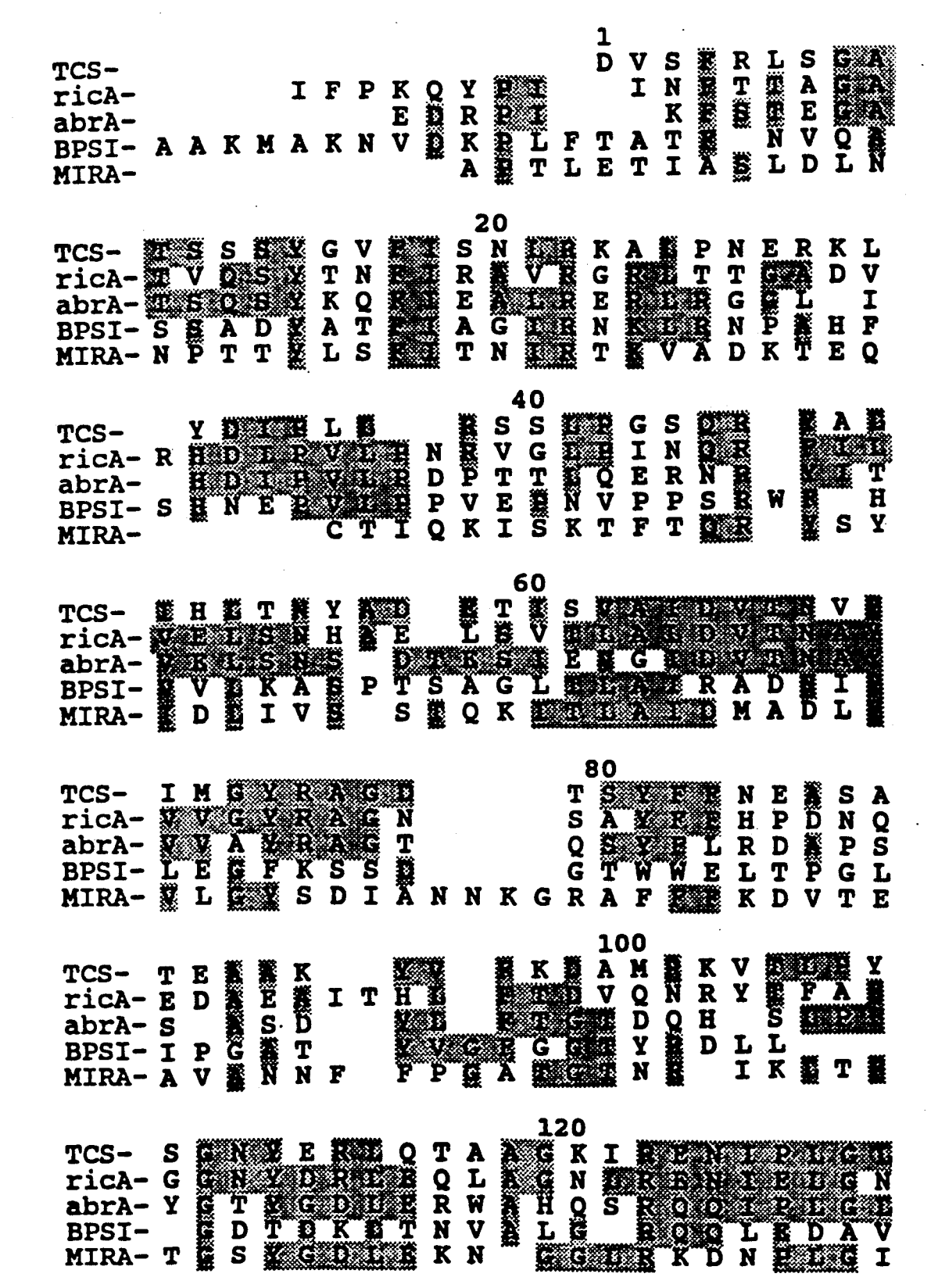

An energy minimized molecular model for α-TCS has been generated by fitting its primary amino acid sequence to the known crystallographic structure for ricin A-chain, a related RIP. Guided by this model and by peptide sequence homology alignments with ricin A-chain and other RIPs (FIG. 9), RIP-invariant residues residing in a putative active site cleft were determined. Two of these sites, Glu160 and Arg163 of the α-TCS peptide sequence (Example 6, FIG. 11), have been modified to assess their relationship to the translation-inhibitory and anti-HIV-1 replication activities of α-TCS. These mutations altered Glu160 and Arg163 to Asp and Lys, respectively. Proteins containing one or both of these alterations were expressed in E. coli, and were purified to approximately 95% homogeneity (Example 6). These mutant proteins were compared to the unmodified protein made from a synthetic gene (KQS; also expressed in E. coli), for their ability to inhibit in vitro translation (IVT) in a rabbit reticulocyte system and to reduce production of p24 antigen in HIV-1 infected T-cells.

Figure 15:
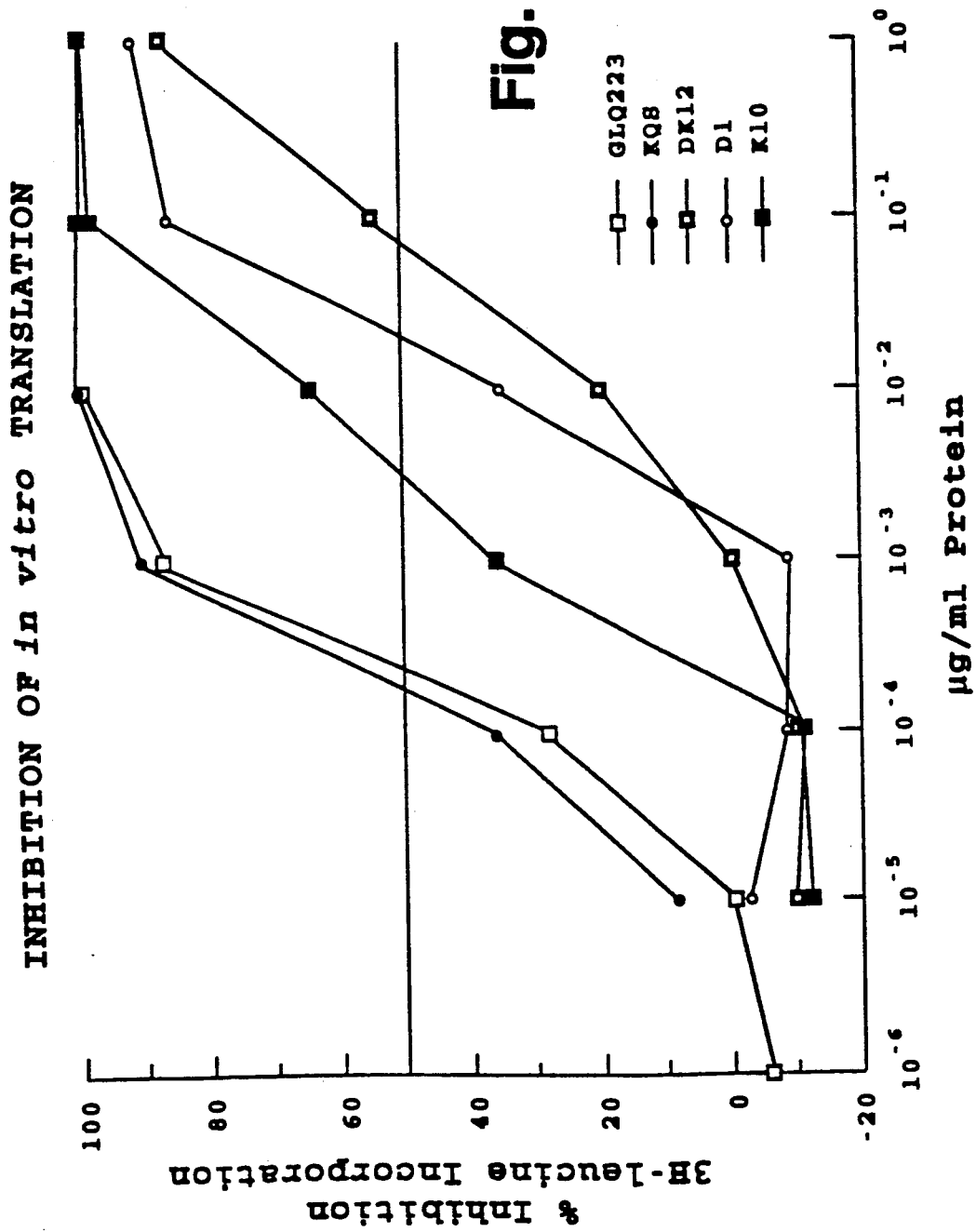
FIG. 15 shows the ability of the α-trichosanthin protein, synthesized from the synthetic gene, to inhibit in vitro translation reactions, relative to mutant forms of the protein.

The doubly-modified variant (DK12) was found to be almost 3 logs less active at inhibiting in vitro translation (FIG. 15) and more than one log less active at inhibiting p24 production, when compared to the unmodified protein. The singly-modified variants showed intermediate activities, for both inhibition of translation and p24 production, relative to DK12 and KQS. Additional mutant proteins are being produced that will allow investigation of the function of other RIP-invariant residues in the α-TCS molecule.

The synthetic gene described above, provides a tool to generate variants of the α-trichosanthin protein. These proteins can be screened, as described above, for less active and more active variants which affect the ribosome inhibitory and/or HIV-I inhibitory activities of the wild-type protein.

F. TCS Fusion Protein

In another aspect, the invention includes TCS fused at its amino or carboxy end with a ligand peptide to form a fused ligand/TCS protein. The TCS making up the fused protein is preferably rTCS or bioactive portion thereof, as described above.

Where TCS is used to inhibit viral expression in HIV-infected human cells, the protein may be advantageously fused with a soluble CD4 peptide, which shows specific binding to the HIV-related gp120 antigen present on the surface of HIV-infected cells (Till), or with a monoclonal antibody specific against an HIV-specific cell surface antigen.

The fused TCS protein may be formed by chemical conjugation or by recombinant techniques. In the former method, the peptide and TCS are modified by conventional coupling agents for covalent attachment. In one exemplary method for coupling soluble CD4 to TCS, recombinant CD4 (rCD4) is derivatized with N-succinimidyl-S-acetyl thioacetate (Duncan), yielding thiolated rCD4. The activated CD4 compound is then reacted with TCS derivatized with N-succinimidyl 3-(2-pyridyldithio) propionate (Cumber), to produce the fused protein joined through a disulfide linkage.

As an alternative method, recombinant TCS (rTCS) may be prepared with a cysteine residue to allow disulfide coupling of the rTCS to an activated ligand, thus simplifying the coupling reaction. The TCS expression vector used for production of rTCS can be modified for insertion of an internal or a terminal cysteine codon according to standard methods of site-directed mutagenesis.

Figure 8:
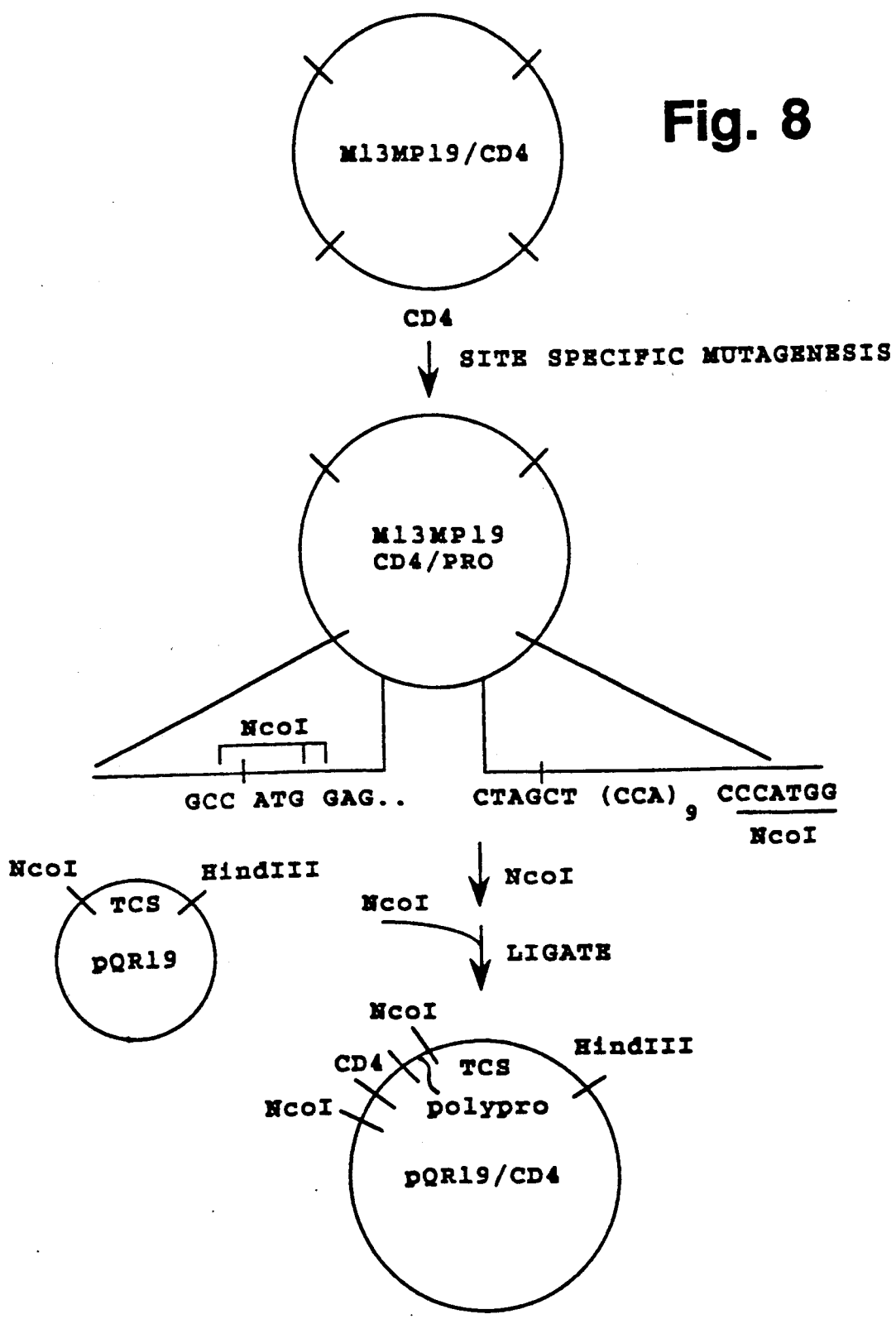
FIG. 8 illustrates the steps in a method for producing a fused TCS protein containing a CD4+peptide moiety.

In a preferred method, the fused protein is prepared recombinantly using an expression vector in which the coding sequence of the fusion peptide is joined to the TCS coding sequence. FIG. 8 illustrates the construction of an exemplary expression vector for a fused TCS/CD4 protein.

Briefly, an EcoRI-StuI DNA fragment containing the coding region for the first 183 amino acids of mature CD4 peptide, which may effectively bind gp120, (Maddon) is inserted into an M13MP19 phage between SmaI and EcoRI sites and the vector, in a single-strand form, is then subjected to primer mutagenesis. Specifically, the aminoterminal portion of the CD4 gene is modified with primer MP101 (5'-CCAGCAGCCATGGAGG-GAAACAAAG -3'); and the carboxy portion of the gene is modified with primer MP102 (5'-CATCGTGGTGCTAGCT-CCACCACCACCAC-CACCACCACCACCACCACCCATGGAGGCATG-CAAGCTTG -3'). These modifications place an NcoI site containing an ATG start codon at the beginning of the mature CD4 peptide coding sequence, and a string of proline codons terminating at an NcoI cloning site after amino acid 180 in the CD4 sequence, as illustrated in FIG. 8.

The NcoI fragment from the phage vector is inserted into the pQR19 expression vector from above previously cut with NcoI. Successful recombinants are confirmed by restriction analysis for proper orientation of the CD4 sequence insert.

An expression vector formed as above, and designated pQR19/CD4 in FIG. 8, contains (a) a synthetic trp/lac promoter positioned appropriately ahead of a ribosome binding site that is also positioned appropriately ahead of an ATG start codon contained within an NcoI site, (b) the CD4 coding sequence, (c) a spacer coding sequence coding for 10 proline residues, which spaces the CD4 and TCS protein moieties, (d) the coding sequence for mature TCS and (e) a stop codon positioned adjacent the carboxyterminal codon of mature TCS. The method generally follows that used in fusing a soluble CD4 to domains 2 and 3 of pseudomonas exotoxin A, as described previously (Chaudhary).

Plasmid pQR19/CD4 is analysed for expression of fused TCS protein as above. Briefly, the expression vector is cultured in a suitable bacterial host under IPTG induction conditions to a desired cell density. The cells are harvested, ruptured by sonication, and the cell material is clarified by centrifugation. The clarified material is tested for (a) binding to gp120 antigen, to confirm CD4 ligand binding activity, and (b) for ribosome inhibition activity, to confirm TCS enzymatic activity.

The protein may be purified by molecular-sieve and ionexchange chromatography methods, with additional purification by polyacrylamide gel electrophoretic separation and/or HPLC chromatography, if necessary.

It will be appreciated from the above how other ligand/TCS-containing fusion proteins may be prepared. One variation on the above fusion is to exchange positions of the CD4 and TCS molecules in the fusion protein.

III. Genomic Cloning of Ribosome-inactivating Proteins deriving from a Multi-gene Family in *Trichosanthes kirilowii* Maxim.

Two Type I ribosome-inactivating proteins (RIP) have been isolated from the plant *Trichosanthes kirilowii* Maxim: (1) α-trichosanthin, isolated from the root tubers (Law, Yeung); and, (2) trichokirin, isolated from seeds (Casellas). As described above, two cloned sequences related to α-trichosanthin, designated pQ21D and pQ30E, have been isolated from the genome of *T. kirilowii.* In an effort to isolate a full length clone for pQ30E, an SpeI lambda ZAPII genomic library was constructed (Example 7). This library was probed with the entire EcoRI insert from clone pQ30E (FIG. 16) under low stringency conditions. Of 21 cloned inserts identified by a positive hybridization reaction (Example 7), 5 clones showing different restriction digest patterns were selected for complete DNA sequence analysis; two of these cloned inserts had identical sequences. Four unique cloned inserts, designated pQ2, pQ3, pQ12 and pQ24, were also identified; each insert encoded a putative full length RIP protein (FIGS. 17-20).

DNA sequence and protein alignment analysis showed that the insert coding sequences fall into 3 subgroups with amino acid sequences similarities ranging from 58%-75% between the subgroups, and >00% within each subgroup (FIG. 21). By comparison and alignment with pQ21D, the insert coding sequences contain the following characteristics: 1) each insert sequence encodes a prepro protein with a putative signal peptide of 23 amino acids, and a carboxy terminal extension consisting of 1, 10 or 19 amino acids; 2) each insert sequence contains amino acid residues which are characteristic for RIPs; 3) the corresponding proteins possess between 0 and 4 potential N-linked glycosylation sites and have calculated pI's of 9.6 to 9.9; 4) the predicted size of the proteins are 247 or 248 amino acid residues; and, 5) the proteins are translated from unspliced messages—there are no introns in any of the clones.

From the data presented above the genome of *Trichosanthes kirilowii* Maxim appears to contain a multi-gene family encoding multiple ribosome-inactivating proteins; this is similar to an RIP family in, for example, *Ricinus communis.*

The coding sequences of the members of this multi-gene family can be used as probes to identify, for example, additional members of the gene family in Trichosanthes or to identify homologous genes in other plants. The proteins corresponding to the multi-gene family coding sequences can be expressed in bacterial expression systems (as described above for α-trichosanthin), and the proteins used to (1) examine the proteins' ribosomeinactivating and anti-HIV-I properties, and, (2) generate antibodies which can be used to examine expression patterns of the proteins in Trichosanthin tissues.

FIG. 22 is a representation of the ribosome-inactivating protein multi-gene family of *Trichosanthes kirilowii.* The vertical columns of amino acid residues at each site show acceptable substitutions at that site based on comparisons of the coding sequences of all the known genes of the family (Example 7, FIG. 21). For example, in FIG. 22 the first amino acid residue is M, followed by I or N, followed by R, followed by F, followed by L, P, or S, etc. Nucleic acid coding sequences can be determined for any protein coding sequence derived from FIG. 22 and probes or synthetic genes synthesized for the chosen protein coding sequence as described above in Section II-E for α-TCS. The probes can be used to identify, for example, additional members of the ribosome-inactivating protein gene family in Trichosanthes or to identify homologous genes in other plants. The synthetic gene can be used to recombinantly express the chosen protein coding sequence: this protein's ribosome-inactivating and anti-HIV-I properties can then be examined.

IV. Obtaining RIP Coding Sequences

As described above, the coding sequence of TCS was obtained by selective amplification of a TCS coding region, using sets of degenerate primers for binding to spaced coding regions of a TCS coding sequence in genomic DNA. This section describes the use of such sets of degenerate primers for selective amplification of coding sequences for a variety of RIPs.

In selecting suitable primer sets, the amino acid sequences of TCS and one or more RIPs are examined for regions of sequence homology, i.e., regions where the amino acids sequences are identical or differ at most by one or two amino acid residues. Typically, the length of the regions being examined should contain at least about 7 amino acids, i.e., at least about 20 nucleotides, although it is appreciated that longer oligonucleotide primers are preferred, even though overall complexity is increased.

FIG. 9 shows the complete amino acid sequences of TCS (top line), and three RIPs whose sequences have been published. The RIPs are ricin A chain (ricA; Lamb), abrin A chain (abrA; Funatsu) and barley protein synthesis inhibitor (BPSI; Asano), and Mirabillis anti-viral protein (MIRA; Habuka). The amino acids are indicated by conventional one-letter codes. Amino acid matches among the four proteins are shaded.

As seen from the figure, there are several regions, each containing at least seven amino acids, which show a high degree of amino acid sequence homology among the proteins, i.e., sequence matching in at least about 4 of the 7 amino acid positions. The relatively greater homology among TCS, ricin A chain and abrin A chain, as compared with barley protein synthesis inhibitor, presumably reflects evolutionary divergence since TCS, ricin A and abrin A chain are all derived from dicotyledons, and barley inhibitor is obtained from a monocotyledon.

Considering the sequences from amino acids 63-70 in the upper line in FIG. 9, it is seen that the amino acid sequence for abrin A chain —GIDVTNAY— differs from the corresponding TCS and ricin A chain sequences by only 2 amino acids each, and therefore is a likely choice for design of the primer set. The disadvantage of this sequence region is that the presence of a leucine residue (L) in ricin A chain introduces a six-fold degeneracy at that point in the sequence. However, this problem is not prohibitive if inosine (I) is used in the third and/or first position in each codon to reduce degeneracy.

The abrin sequence in the same 63-70 amino acid region differs from the corresponding TCS by an alanine-to-glycine substitution in the first position. Since a G(G,C)N sequence, where N is all four nucleotides, will hybridize with both the alanine and glycine codons, the primers can be made an additional two-fold degenerate at this position to encompass both TCS and abrin coding sequences. The abrin sequence also differs from the TCS sequence by a valine-to-alanine substitution in the seventh position. An additional two-fold degeneracy at this position can be made that accounts for all possible valine and alanine codons, i.e., G(C,T)N.

Likewise, the abrin sequence in this region differs from the corresponding ricin A chain sequence by the same alanine-to-glycine substitution in the first amino acid position. Additionally, the abrin sequence differs from the ricin sequence by an isoleucine-to-leucine substitution in the second position. Since an ITI sequence will hybridize with all the isoleucine and leucine codons, the primer degeneracy can be normalized at this position. The other five amino acid positions are preferably made degenerate, to optimize the specificity of primer binding to corresponding genomic coding regions. The total number of primers in the final primer set is preferably between about 16–128 although more complex mixtures can be used. The primers are synthesized conventionally using commercially available instruments.

A second set of degenerate primers from another region of TCS which is homologous in amino acid sequence to RIPs is similarly constructed.

The two primer sets are useful in a method for selectively amplifying RIP coding sequences present in genomic DNA from selected plant sources, employing repeated primer-initated nucleic acid amplification. As an example, to amplify coding sequences for abrin A chain protein, genomic DNA from *Abrus precatorius* is isolated, and mixed with the primer sets, all four deoxynucleosides triphosphates, and polymerase, as outlined in Example 2. After repeated cycles of primer binding and strand extension, the material is fractionated by gel electrophoresis and amplified fragments are identified, for example, by ethidium bromide staining or by autoradiography, according to procedures described in Example 2. Fragments amplified from an RIP gene can be identified by size, as the selection of specific primer sets would predict the size range of the fragment that is amplified. Genes for RIPs are not believed to contain any introns (Halling and the present application).

The amplified material is then used as a (radiolabeled) probe for detecting genomic library clones prepared from genomic DNA from the plant source, e.g., *Abrus precatorius*. The identified library clones are analysed, as above, for fragments containing a complete RIP coding sequence. Alternatively, overlapping genomic library fragments containing amino and carboxy portions of the coding sequence can be combined to produce a complete coding sequence. The properties of the coding sequence are then tested as outlined above to determine ribosome-inhibitory properties and/or anti-viral properties. Further, these nucleic acid coding sequences can be used as probes to identify additional RIP sequences.

More generally, this aspect of the invention includes a primer mixture and method of using the mixture for selectively amplifying RIP coding sequences. The primer mixture includes a first set of sense-strand degenerate primers, and a second set of anti-sense primers, where each set contains at least one primer sequence which is effective to hybridize with the corresponding coding sequence in TCS which encodes the region of amino acid homology with RIPs, particularly RIPs from dicotyledon plants.

Once the amplified genomic sequence of a ribosomeinactivating protein is obtained the sequence can be used as a probe for isolating genomic library fragments containing the desired RIP coding sequence. The protein products expressed from these genomic fragments can then be tested for their ribosome-inhibitory activity and/or anti-viral activities as described above for TCS.

It will be appreciated that the method can be used to obtain the coding sequence from plants which produce known RIPs, and also to screen other plants for the presence of genes encoding as-yet-unknown RIP or RIP-like proteins.

The following examples illustrate various methods used to obtain and verify the nature of the coding sequence and recombinant proteins described above. The examples are intended to illustrate, but in no way to limit, the scope of the invention.

Materials and Methods

*T. kirilowii* root tubers were obtained from the Canton region of the People's Republic of China. Leaves of *T. kirilowii* were obtained from Korea and were collected and immediately frozen on dry ice for shipment. Samples were than stored at −70° C.

QAE Zetaprep TM anion exchange cartridges and SP Zetaprep TM cation exchange cartridges were supplied by AMF Cuno Corp. (Meridan, Conn.); and Pellicon ultrafiltration membranes (10,000 MW cutoff), from Millipore Corp. (Bedford, Mass.).

M13/MP18 and M13/MP19 were obtained from New England Biolabs (Beverly, Mass.). Lambda-Zap II TM cloning vector system was supplied by Stratagene (La Jolla, Calif.). Expression vector PKK233-2 and its IPTG-inductible *E. coli* host strain, XLI-blue, were obtained from Pharmacia (Piscataway, N.J.) and Stratagene (La Jolla, Calif.), respectively. Restriction enzymes were obtained from New England Biolabs (Beverly, Mass.) or Promega (Madison, Wis.). DNA primer-initiated amplification reagents were obtained from Perkin-Elmer/Cetus (Norwalk, Conn.).

Synthetic oligonucleotide primers were prepared by conventional, automated phosphoramidite methods using either a Biosearch Cyclone or an Applied Biosystems Model 380B instrument.

The methods for preparation and manipulation of nucleic acids, and the recombinant DNA techniques employed herein are broadly accepted and applied and are generally referenced by Ausubel, F. M. et al. (eds) "Current Protocols in Molecular Biology" Vols. 1 and 2, John Wiley & Sons, New York (1988) and Maniatis, T., et al., "Molecular Cloning: A Laboratory Manual," Cold Spring Harbor Laboratory, 1982.

EXAMPLE 1

Purification of TCS

The purification of TCS has been described in coowned, co-pending U.S. application Ser. No. 07/333,181. A clarified extract of the roots of *T. kirolowii* was obtained by overnight extraction of homogenized tubers of *T. kirilowii* in normal saline (0.9% NaCl) adjusted to pH=8.0 with NaOH. The extract was clarified by centrifugation, and the clarified material was passed through a QAE Zetaprep TM anion exchange resin, which is supplied commercially in cartridge form. The ion exchange step was carried out at low ionic strength, i.e., low conductivity, which has been found effective to enhance TCS purification, and in particular, to remove hemagglutinin contaminants. The low-conductivity buffer was 20 mM phosphate, pH 8.0.

The flowthrough from the anion exchange resin was adjusted in pH and ionic strength, and preferably concentrated, preparatory to further protein purification by chromatography on a cation exchange resin. The concentration step was carried out by ultrafiltration using a 10,000 molecular weight filtration membrane, yielding a solution which is largely free of low-molecular weight contaminants.

The treated flowthrough material equilibrated with 50 mM phosphate, pH 6.0 buffer was applied to an equilibrated SP Zetaprep TM cation exchange resin, and the column was washed extensively with buffer (15-20 volumes) until the elution profile reached a baseline value. The extensive washing removed loosely bound material, including, particularly, endotoxins and high molecular weight lipopolysaccharides (LPS), and is necessary for achieving high purity TCS.

TCS was now eluted from the column in highly purified form by elution with 50 mM phosphate buffer, pH 6.0 containing 60 mM NaCl, to release bound TCS from the resin. The purified TCS protein was at least about 98% pure, as evidenced by HPLC profile and staining patterns on SDS gel electrophoresis.

EXAMPLE 2

Preparing Cloned Genomic Fragment Containing TCS Coding Sequence

A. Amplified TCS Coding Sequence

Genomic DNA was isolated from frozen *T. kirilowii* leaves by a modification of published methods (Taylor). Briefly, frozen tissue was ground to a fine powder using a mortar and pestle kept on dry ice. β-mercaptoethanol was then added to 2% of the initial volume followed by an equal volume of hot 2× extraction buffer (2% cetyl-trimethyl-ammonium bromide (CTAB), 100 mM Tris-Cl, pH 8.0, 20 mM EDTA, 1.4 M NaCl).

This slurry was gently stirred in a 55° C. water bath until the temperature reached 50° C. The slurry was then transferred to appropriate centrifuge bottles and extracted twice with an equal volume of chloroform-:isoamyl alcohol (24:1). Phase separation was achieved by centrifugation. A 1/10 volume of 10% CTAB was added and the extraction repeated.

The upper aqueous phase was removed to another container and the DNA precipitated by adding an equal volume of precipitation buffer (1% CTAB, 50 mM Tris-Cl, pH 8.0, 10 mM EDTA) to lower the sodium concentration to 0.35 M. The DNA was collected and washed with cold 70% ethanol, 0.1 M sodium acetate to convert the DNA to a sodium salt, followed by a wash by 95% cold ethanol. The DNA could then be dried and redissolved in 10 mM Tris-Cl, pH 7.5, 1 mM EDTA. To further eliminate contaminants, the DNA was re-precipitated from CTAB by adding an equal volume (original) of 2× extraction buffer, followed by two volumes of (original) TE buffer (10 mM Tris-HCl, 1 mM EDTA), pH 8.0. The DNA was once again converted to the sodium salt, washed with ethanol as above, dried, and dissolved in TE buffer, pH 8.0. Greater than 5 mg of high molecular weight DNA was obtained from approximately 35 g of tissue.

Three degenerate sets of probe sequences were synthesized, corresponding to two separate coding regions. The first DNA sequence is a 35-mer and encompasses the protein sequence overlined and denoted A in FIG. 1, and the second sequence is a 32-mer and encompasses the protein sequence overlined and denoted B in the figure.

The probe sets were prepared by conventional automated methods using instruments commercially available and following the manufacturers' instructions. (Biosearch, San Rafael, Calif., and Applied Biosystems, Foster City, Calif.). Deoxyinosine nucleotides were incorporated in order to generate probes longer than 20 nucleotides of manageable complexity (Ohtsuka; Takahashi). The sense-strand probe set corresponding to the 35-mer, designated MPQP-1, included 128 isomers. The anti-sense-strand second and third sets, designated MPQP-2 and MPQP-3, each included 128 isomers and were 32-mers.

A DNA amplification reaction was carried out by repeated primer initiated strand extension, in a reaction mixture containing (a) 1-2 micrograms of the *T. kirilowii* DNA isolated as above, (b) $^{32}$P-labeled MPQP-1 and an equimolar mix of unlabeled MPQP-2 and -3, as primers, (c) all four deoxynucleoside triphosphates, and (d) Taq polymerase. About 20 rounds of thermal cycling were performed, employing conventional DNA amplification reaction conditions, as outlined in instructions from the manufacturer (Perkin Elmer-Cetus, Norwalk, Conn.). A similar DNA-amplification reaction was carried out using unlabeled primer sets.

The product of the DNA amplification step was fractionated on 3% Nusieve, 1% ME agarose (Seakem TM, FMC Bioproducts, Rockville, Md.) and stained with ethidium bromide. A major product of about 255 base pairs was detected. The material was also fractionated on 5% polyacrylamide gel electrophoresis and the bands detected by autoradiograpy, with similar results. In both cases, very little DNA other than the amplified material was detected.

Amplified DNA was recovered from polyacrylamide gels by elution followed by ethanol precipitation. A portion of one such preparation, approximately 100 nanograms, was taken for DNA sequence analysis. The DNA sample plus 30 ng of unlabeled MPQP-1 were taken up in 10 μl of TE (10 mM Tris-HCl, pH 7.5, 1 mM EDTA) and heated to 100° C. for 5 minutes to denature the double-stranded fragment. The mixture was quick-frozen on dry ice to prevent the template from annealing. Two μl of 5× Sequenase sequencing buffer (USB Biochemicals, Cleveland, Ohio) was added and the primer allowed to anneal to the template for 5 minutes at 37° C. The standard sequencing protocol supplied by the manufacturer was then followed.

The DNA sequence obtained and its translation into all three reading frames is shown in FIGS. 3A (for the sense strand) and in FIG. 3B (for the complementary strand).

B. Cloned Library Fragment with the Complete TCS Coding Sequence

Genomic DNA obtained as above was digested to completion with EcoRI and cloned into a standard library cloning vector, in this case, the Lambda-Zap II TM system of Stratagene (La Jolla, Calif.). For use as a probe, the amplified 255-bp fragment from above was radiolabeled by random priming (Boehringer-Mannheim kit, Indianapolis, Ind.).

Approximately $0.5-1.0 \times 10^6$, plaques were probed with the $^{32}$P-radiolabeled 255-bp probe. Two clearly positive plaques were picked, amplified and converted to plasmid, according to protocols supplied by Stratagene. One clone, designated pQ21D, contained an approximate 4kb insert which included the complete TCS coding sequence; the other, designated pQ30E, contained an approximate 0.6 kb insert.

The region of pQ21D containing the TCS coding region was sequenced by standard double-strand sequence methods, using universal sequence primers as well as unique synthetic oligonucleotide primers as needed. A smaller subclone containing only the TCS coding region was generated by subcloning the 1.2 kb EcoRI to NcoI fragment (FIG. 4) from pQD21D into pKK233-2. The resulting recombinant plasmid was designated pQD12D/pKK233-2.

EXAMPLE 3

Expressing ant TCS (rTCS)

The pQ21D/pKK233-2 cloning vector from Example 2 was divided into two samples. One sample was digested with EcoRI and SalI, to release an EcoRI to SalI fragment containing the amino portion of the TCS gene. A second portion of the DNA was digested first with NcoI, and treated with Klenow to generate a blunt end. The DNA was then digested with SalI to release a SalI to NcoI (blunt) fragment containing the carboxy portion of the gene. After isolating the two fragments by gel electrophoresis, the EcoRI to SalI fragment was cloned into M13MP19 (EcoRI to SalI), and the SalI to NcoI (Klenow repaired) fragment was cloned into M13MP18 (SalI to SmaI). Fragment insertion and production of single-strand phage DNA was performed according to known methods.

The phage single-strand DNA's were subjected to primer mutagenesis using standard methods. The amino portion of the gene (in the M13MP19 vector) was modified with primer QNcoN (5'-CCTGCTGTGGCCATGGATGTTAGC -3'); and the carboxy portion of the gene was modified with primer QTerl (5'-CGAAACAATATG-GCATAATAAAGCTTCCGAGCTCG -3'). These modifications placed an NcoI site containing an ATG start codon at the beginning of the mature TCS protein sequence and a double TAA translation stop sequence plus a HindIII cloning site after the carboxy end of the mature sequence, as illustrated in FIG. 5.

The fragments containing the modified sequences were excised from purified phage DNA as an NcoI-SalI and an SalI-HindIII fragment, respectively, and cloned together into NcoI-HindIII digested pKK233-2. pKK233-2 is a plasmid containing a synthetic trp/lac promoter positioned appropriately ahead of a ribosome binding site that is also positioned appropriately ahead of an ATG start codon contained within an NcoI site. It is supplied commercially (Pharmacia).

Several clones were characterized and verified to contain the modified insert. The DNA sequences of the modified regions were directly verified for one, designated pQR19.

The plasmid pQR19 and similar clones were propagated in the E. coli host strain, XL1-blue. The significant feature of the strain is that it carries the lacI[9] repressor gene on a F' episome (discussed above). LacIq protein controls expression from the lac operator and is blocked from repression by the addition of IPTG to 5 mM. Plasmid pQR19 and another isolate were analyzed for expression of TCS. Cultures were first grown in Luria broth medium supplemented with 100 μg/ml ampicillin, to select for maintenance of the plasmid, to an $A_{600}$ of 0.7 measured at 600nm before adding IPTG, then allowed to grow for 4 hours. These conditions did not result in high levels of expression.

Cultures were then inoculated in Luria broth plus 100 μg/ml ampicillin containing 5 mM IPTG, and allowed to grow to saturation density overnight (pQR19/XL1-blue induced cells). The induced cells were collected by centrifugation, resuspended in 100 mM Tris-HCL, pH 8.5, 5 mM EDTA at a concentration of about 10 $A_{600}$ units/ml and disrupted by sonication. Aliquots were taken and centrifuged at 15,000×g for 5 minutes to separate soluble from insoluble components.

The insoluble, pelleted material was resuspended in sonication buffer to the same volume as the original aliquot. Samples of each fraction were run on 10% SDS-PAGE. One set of samples was stained for total protein with Coomassie Blue; another set of samples was blotted for Western analysis, with the results discussed in Section II.

EXAMPLE 4

Biological Activity of rTCS

A. Inhibition of HIV Replication

The ability of rTCS to mediate selective inhibition of HIV replication in infected T-cells was evaluated in parallel with purified plant-derived material. Cells of the CD4+ T-cell line VB (Lifson, 1986) were inoculated with HIV-1 by incubation at 37° C. for one hour with an aliquot of a titered cryopreserved HIV-1 virus stock (virus isolate HIV-1$_{DV}$ (Crowe, 1987)). After washing, the cells were resuspended to $1.11 \times 10^5$ per ml, and 0.9 ml of this suspension plated in replicate wells of 24 well culture plates. 0.1 ml volumes of serial dilutions of purified plant-derived TCS and rTCS were then added at 10× the desired final concentrations to yield 1.0 ml cultures containing $1 \times 10^5$ cells in 1.0 ml of culture medium containing the desired concentration of TCS. After culturing for 4 days at 37° C. in a humidified 5% $CO_2$/air atmosphere, culture supernatants were harvested and viral replication in treated and control cultures was assessed by measuring HIV p24 antigen content using a commercially available capture immunoassay kit according to manufacturer's instructions (Coulter, Hialeah, Fla.).

As shown in FIG. 6 (closed boxes), in accord with observations reported elsewhere (U.S. Pat. No. 4,795,739), plant-derived TCS purified to apparent homogeneity from the root tubers of T. kirilowii inhibited HIV replication in a concentration-dependent fashion in this acute infection assay system. The biological activity of rTCS produced in E. coli and purified to apparent homogeneity (open boxes), was essentially indistinguishable from that of the native product when tested in parallel in an assay system for inhibition of HIV replication at TCS concentrations above 0.005 μg/ml (FIG. 6). At lower concentrations, rTCS appears to show slightly less specific activity than the plant-derived protein.

B. Inhibition of Cell Free Translation In Vitro

The ability of TCS to irreversibly inactivate ribosomes, thereby inhibiting protein synthesis, is conveniently measured in standardized assays of in vitro translation utilizing partially defined cell free systems composed, for instance, of a rabbit reticulocyte lysate preparation as a source of ribosomes and various essential cofactors, mRNA template(s) and amino acids. Use of radiolabelled amino acids in the reaction mixture allows quantitation of incorporation of free amino acid precursors into trichloroacetic acid precipitable proteins.

As shown in FIG. 7, the protein synthesis-inhibitory activity of rTCS produced in *E. coli* and purified to apparent homogeneity, is indistinguishable from that of plant-derived TCS.

EXAMPLE 5

Hydropathy Index Computation for the Trichosanthin Coding Sequences

The SOAP program from IntelliGenetics PC/GENE TM software package was used to generate the hydropathicity plot of FIG. 10. The SOAP program uses the method of Kyte et al. to plot the hydropathicity of the protein along its sequence. The interval used for the computation was 11 amino acids. In FIG. 10, the hydrophobic side of the plot corresponds to the positive values range and the hydrophilic side to the negative values range.

The first 23 amino acids of the trichosanthin sequence are as follows:

Met Ile Arg Phe Leu Val Leu Ser Leu Leu Ile Leu Thr Leu Phe Leu Thr Thr Pro Ala Val GluGly.

As can be seen from FIG. 10, this sequence has a high degree of hydrophobicity. The length of the sequence and the degree of hydrophobicity make the above sequence an ideal candidate for a secretory signal sequence.

EXAMPLE 6

Structure-Function Studies of α-Trichosanthin

The protein obtained from the above described alpha-trichosanthin encoding nucleic acid sequence isolated from the genome of *T. kirilowii* contained two conservative amino acid changes in the alpha-TCS protein coding sequence relative to the primary sequence which was determined for alpha-TCS. This example describes the construction of a nucleic acid coding sequence for a synthetic gene alpha-trichosanthin gene based on codons selected to represent the primary amino acid sequence of the alpha-trichosanthin protein isolated from plant material. The example further describes the creation of mutant alleles of the gene encoding α-trichosanthin.

(i) Sources of Plasmids, Bacterial Strains, Reagents and Enzymes

Bluescript TM was purchased from Stratagene (La Jolla, Calif.); pACYC184 (ATCC no. 37033) was obtained from the American Type Culture Collection, Rockville, Maryland. The expression plasmid, pKK233-2, was obtained from Pharmacia (Piscataway, N.J.). The *Escherichia coli* strains used for transformation include DH5 (F-, recAI, endA1, hsdR17 ($r_k m_k^+$), supE44, λ-, thi-1, gyrA, relA1), from BRL (Gaithersburg, Md.) and XL1-Blue (recA1, endA1, byraA96, thi, hsdR17 ($r_k m_k^+$), supE44, relA1, λ-, lac-, (F', proAB, lacIqZΔM15, Tn10 (tetʳ)) from Stratagene. JM105 (thi, rpsL, endA, sbcB15, hsdR4, Δ(lac-proAB), (F', traD36, proAB, lacI¹ZΔM15)) was used for expression of the synthetic gene. LB medium (Maniatis et al.) was used for the propagation of bacteria. Expression was performed in M9 medium (Maniatis et al.) containing supplements of glucose or glycerol (0.2%) thiamine (2 μg/ml), casamino acids (CAA) (0.3%), IPTG (5 mM), and ampicillin (100 μg/ml).

Restriction endonucleases were purchased from either Bethesda Research Laboratories (Gaithersburg, Md.) or Promega Biotec (Madison, Wisc.); the enzymes were used according to the manufacturers, recommendations. T4 DNA ligase was purchased from International Biotechnologies, Inc. (IBI, New Haven, Conn.).

(ii) Vector Construction

An 80 base pair (bp) polylinker was constructed which contained the restriction sites KpnI, HindIII, NsiI, SpeI, PstI, BssHII, MluI, SalI, AatII, and SacI, in the order found in the synthetic gene (FIG. 11). These sites were used to clone and assemble the individual synthetic nucleic acid fragments into a contiguous sequence. One end of the polylinker contained a BanI overhang and the other end contained an XbaI overhang to facilitate cloning into pACYC184.

A chloramphenicol-resistant ($Cm^R$) vector, pPS200, was constructed from ligation of the synthetic polylinker to a 1900 bp BanI-XbaI fragment of pACYC184 containing the chloramphenicol acetyltransferase gene. An ampicillinresistant (Ap) vector, pPS300, was constructed by replacing the polylinker present in pBluescript TM with the above-described synthetic polylinker. The relevance of using these particular vectors is that they contain compatible replicons; thus, both vectors can be stably maintained in the same cell. The compatible replicons used in construction of the plasmids were taken advantage of in constructing pPS300 and in condensing the separate, synthetic DNA fragments into the complete gene as described below.

Construction of pPS300 involved digesting both pBluescript TM and pPS200 with KpnI, ligating the linear plasmids, transforming competent *E. coli* DH5 cells with the ligation mixture, and selecting doubly resistant clones on LB plates containing both ampicillin and chloramphenicol. The plasmids were isolated from positive clones and digested with SacI to determine the orientation of the ligated plasmids and to generate two new plasmids in which the polylinker sequences were exchanged. Those in which the two vector components were ligated in the correct orientation (FIG. 12A), i.e., with the two polylinker sequences essentially opposite each other, not juxtaposed (FIG. 12B), were selected. The SacI digest of one of the selected plasmids was diluted and the individual components circularized by ligation. Upon transformation into competent DH5 cells, cells carrying individual plasmids were selected as being $Ap^R Cm^S$ or $Cm^R Ap^S$ (ampicillin-resistant/-chloramphenicol-sensitive or chloramphenicol-resistant/ampicillin-sensitive). The resulting plasmids from these manipulations are a pBluescript TM vector carrying the synthetic polylinker (pPS300) and a $Cm^R$ plasmid carrying the pBluescript TM polylinker.

(iii) Fragment Cloning

Synthetic gene fragments corresponding to the sequences shown in FIG. 11 were synthesized on an ABI 380B DNA synthesizer using cyanoethyl phosphoramidite chemistry and were purified tritylated on a PRP-3 column purchased from Hamilton Company.

Complementary synthetic oligonucleotides were mixed at 10 picomoles per μl in 10 mM Tris, pH 8; 10 mM MgCl₂; 10 mM NaCl. These mixtures were heated to 100° C. for 1 minute, and then allowed to cool slowly to room temperature for annealing.

Successful ligation of the synthetic oligonucleotide fragments into the polylinker required a 20–40× molar excess of the annealed oligonucleotides, in a final DNA concentration of 100 ng per μl. Ligation reactions were carried out at room temperature for two hours or at 16 degrees overnight (Maniatis et al.). The ligation mixes were used to directly transform competent DH5 or XL1-Blue cells. Transformants were selected on LB containing either ampicillin or chloramphenicol. Plasmids obtained from the selected transformants were screened for presence of insert by one of two methods: digestion with a restriction enzyme having a cleavage site contained in the insert fragment; or, comparison of the fragment sizes generated from digestion with restriction enzymes having sites which lie outside of the insert. Plasmids containing candidate inserts were checked further for mutations or deletions by nucleic acid sequencing of the insert DNA.

Sequencing of each cloned synthetic fragment was performed on double-stranded plasmid DNA using Pharmacia T7 (Pharmacia) and USB (U S Biochemicals, Cleveland, Ohio) Sequenase ™ Kits. Reactions were performed essentially according to the manufacturers' recommendations, with the following changes: plasmid denaturation was performed at 85° C. instead of at room temperature, and the samples contained in the microtiter plates were chilled on ice prior to the addition of the labeling reactions, instead of pre-heating to 37° C.

Most fragments had few or no deletions. However, the BssHII-MluI segment, when cloned into pPS300, was either in the orientation opposite to what was desired for condensation (see below) or the sequence had modifications and/or deletions. To get around this problem the fragment was cloned into pPS200. Plasmids containing the insert were identified by screening, and the inserts were sequenced. Four plasmids having the correct sequence were isolated.

(iv) Condensation of the cloned gene fragments

To facilitate the combining of the oligonucleotides into a synthetic sequence corresponding to the trichosanthin protein coding sequence, the synthetic oligonucleotide fragments were cloned separately into each type of vector (pPS200 or pPS300). The plasmid/fragment combinations were chosen such that oligonucleotide fragments which should be adjacent each other in the synthetic gene could be combined by ligation into a hybrid plasmid which could be selected by transformation and replica plating from LB-ampicillin plates to LB-chloramphenicol plates or vice versa. This selection follows the method used to transfer the synthetic polylinker from pPS200 to pPS300 described above.

FIG. 13 shows a generalized schematic diagram for condensation of cloned gene fragments. The numbers at the ends of synthetic fragments correspond to restriction enzyme sites. The figure illustrates the joining of fragment 3–4 to fragment 4–5 using the above described plasmids and cutting at site 4 in each plasmid. These single cut plasmids are then ligated and a plasmid having the two sequences joined in the correct orientation is selected. This plasmid is then cleaved at a restriction site which will generate a plasmid, carrying the joined fragments, which has the desired drug resistance marker (either $Cm^r$ or $Ap^r$). The restriction enzyme digest is diluted and the fragments self-ligated to generate the desired plasmid.

The following description of the construction of the TCS synthetic gene can also be read with reference to FIG. 13. To join two synthetic gene fragments, each clone was cut with a restriction enzyme which had a cleavage site common to an end of each synthetic fragment, thus producing linear plasmids. These linear plasmids were ligated together, transformed into competent DH5, and selected by their resistance to both chloramphenicol and ampicillin. Plasmids were isolated from several candidates which were both chloramphenicol ($Cm^R$) and ampicillin ($Ap^R$) resistant. These plasmids were analyzed using restriction enzyme digestion to determine the orientation of the two synthetic fragments relative to each other. Plasmids having the correct fragment orientations (in which the two gene fragments were joined together) were identified.

Next the joined fragments were segregated to one vector by digesting the plasmid with a restriction enzyme which introduced a single cut at one end of the joined fragments and in the fused polylinker sequence present in the combination plasmid (for example cutting at site 3 in the combination plasmid presented in FIG. 13). The resulting two plasmid pieces were self-ligated, thus preserving intact polylinker regions, and transformed into bacteria. The plasmid containing the linked fragments was selected on the basis of its drug resistance. The choice of whether to segregate the linked fragments into a $Cm^R$ or $Ap^R$ plasmid depended on the nature of the selection marker in the plasmid with which it was to be next combined. For example, if two fragments are linked and propagated in a $Cm^R$ plasmid they are joined in the next round of combining with two fragments which were linked and propagated in an $Ap^R$ plasmid. By cloning adjacent fragments and pairs of fragments into vectors with different antibiotic resistance, the trichosanthin gene was readily condensed step-wise from eight clones down to one clone.

FIG. 14 shows a schematic of the steps taken to clone and condense the synthetic gene for α-TCS. A linear depiction of the synthetic gene and the restriction sites flanking the individual fragments is shown at the top center. These flanking restriction sites, shown in FIG. 14, correspond to the restriction sites shown in bold print in FIG. 11. Throughout the remainder of the Figure the relevant restriction sites are also referred to in one letter abbreviation where appropriate and convenient. Also shown are unique restriction sites contained within the synthetic fragments that were used in screening for positive subclones. The two vectors employed, pPS200 ($Cm^R$) and pPS300 ($Ap^R$) are depicted at the top left and the top right of the figure, respectively. FIG. 14 shows a flow chart that depicts the cloning of the individual synthetic fragments into either pPS200 or pPS300 followed by the ligation of two subclones into a single plasmid in which the two gene pieces are properly joined. In the third row from the top, examples of the two alternative orientations in which the subclones could be ligated are shown along with the selection of the correct orientation for further ligation reactions. For brevity, the self ligations to eliminate one vector component from the doubly-resistant plasmids, leaving the fused gene sequences as part of the second component, are not shown. The final gene fusion is shown as being placed in pPS200 ($Cm^R$) although it was also placed in pPS300 ($Ap^R$) using alternative restriction digestion and ligation to eliminate the pPS200 component.

(v) Expression of synthetic trichosanthin in *E. coli*

After construction of the synthetic trichosanthin gene was completed, the coding region of the gene was cloned into the expression vector pKK233-2 to give a construct similar to that described previously for the genomic clone. An NcoI to SacI (Klenow repaired to blunt) gene fragment from the pPS200 subclone was placed into pKK233-2 from NcoI to HindIII (Klenow repaired to blunt) employing the two plasmid cloning approach described above. It should also be appreciated that other, more standard methods might also be used to subclone the fragment into pKK233-2 (Maniatis et al.). The resulting plasmid, designated pKQS, was initially transformed into the *E. coli* strain XL-1 Blue, described above. It was also transformed into another strain, JM105, which also carries lacI$^q$ for the regulation of the promoter in pKK233-2 from which the synthetic TCS coding sequences were expressed. The latter transformants exhibited better growth characteristics than the XL-1 Blue transformants and were selected for expression and production of protein.

To express the synthetic gene, pKQS/JM105 transformants were grown in M9 medium (Maniatis et al.) supplemented with 0.2% glucose, (0.2%) thiamine (2 µg/ml), casamino acids (CAA) (0.3%), IPTG (5 mM), and ampicillin (100 µg/ml) at 37° C. to saturation density.

(vi) Construction of trichosanthin mutants

In order to investigate the function of a region of trichosanthin suspected to have catalytic activity against eukaryotic ribosomes, mutants of the trichosanthin coding sequence were constructed in vitro. First, a double mutant was made which changed the glutamic acid at position 160 and the arginine at position 163 to an aspartic acid and a lysine, respectively. These mutations were made by replacing the BssHII-MluI fragment of the synthetic gene (FIGS. 11 and 14), in pKQS, with a fragment containing the two codon changes and a diagnostic restriction site (SpeI). A SpeI site was included to facilitate screening of insertion of the new fragment. The new sequence was verified by DNA sequencing.

nine to lysine substitution was made; these mutant coding sequences were named D1 and K10, respectively.

(vii) Purification of mutant proteins

Overnight cultures were harvested by centrifugation and cells were resuspended in ice-cold 100 mM Tris, pH 8.5, 5 mM EDTA). The cells were disrupted by sonication: insoluble materials and unbroken cells were then removed by centrifugation at 10,000×g for 10 minutes. The supernatant was diluted with three volumes of water, and the conductivity was measured to ensure that it was less than 2 mmho. The pH of the sample was readjusted to 8.5 with dilute NaOH, and the solution was recentrifuged at 10,000×g to remove any insoluble proteins, cell debris, and additional bacteria.

A column consisting of A50 QAE Sephadex ion exchange resin (Pharmacia) was activated with 0.1 N HCl followed by 1 M NaCl, and was washed extensively with 10 mM Tris HCl, pH 8.5, to equilibrate. The diluted sample was loaded onto the column at a rate of 2-3 ml per minute and the flow-through material was collected. The pH of the flow-through was then adjusted to 6.0 with dilute Hll, and the solution was centrifuged at 10,000×g to pellet any insoluble proteins. This flow-through material was then loaded onto a C25 or C50 SP Sephadex column which had been activated with 0.1 N NaOH and 1 M NaCl, and equilibrated with 20 mM phosphate buffer at pH 6.0. After addition of the sample, the column was washed extensively with 20 mM phosphate buffer at pH 6.0. The mutant trichosanthin protein was eluted with 20 mM phosphate buffer containing 200 mM NaCl, or with standard phosphate buffered saline (Gibco) (140 mM NaCl). Eluted samples were sterilized by filtration through a 0.45µ low-protein-binding filter (Millex HV, Millipore, Bedford, Mass.) in preparation for in vitro translation and HIV inhibition assays. Based on SDS gel electrophoresis the homogeneity of the mutant trichosanthin proteins was typically about 95%. Protein yield was typically 0.5-1.0 mg/L of cell culture.

(viii) In vitro translation and HIV inhibition assays

The isolated mutant proteins were compared to isolated unmodified trichosanthin protein (KQS) (also expressed in *E. coli*), for their ability to inhibit in vitro translation (IVT) in a rabbit reticulocyte system and to

```
                       Glu160        Arg163
                       GAA           CGC
BssH I                 Spe I
CGCGCTCATGGTTTTGATTCAAAGTACTAGTGACGCTGCAAAATACAAATTCATCGAAACA
GC

GAGTACCAAAACTAAGTTTCATGATCACTGCGACGTTTTATGTTTAAGTAGCTTGTCG
                       Asp           Lys

AAATTGGCAAA
TTTAACCGTTTGCGC
           Mlu I
```

Plasmids containing the mutant coding sequences were screened for the presence, orientation, and number of mutant fragment inserts. A clone which contained the correct mutations, DK12, was expressed as described above for pKQS.

In order to determine the contribution of each amino acid mutation to the overall effect of the double mutant, single mutants were constructed in which either the glutamic acid to aspartic acid substitution or the arginine to lysine substitution was made; these mutant coding sequences were named D1 and K10, respectively.

reduce production of p24 antigen in HIV-1 infected T-cells (assays described in Example 4 above and in U.S. Pat. No. 4,869,903). The double-mutant protein (DK12) was found to be almost 3 logs less active at inhibiting in vitro translation (FIG. 15) and more than one log less active at inhibiting p24 production, compared to the unmodified protein. The singly-modified variants showed intermediate activities relative to DK12 and KQS for both inhibition of IVT (FIG. 15) and production of p24 antigen.

EXAMPLE 7

Isolation of Additional Sequences Homologous to alpha-Trichosanthin

This example describes the cloning of additional coding sequences from *Trichosanthes kirilowii* which have homology to the alpha-trichosanthin nucleic acid coding sequence.

A second genomic DNA library was generated in the lambda ZAPII vector system (Stratagene) as a SpeI restricted bank; genomic DNA was prepared as described above in Example 2. SpeI digested genomic DNA from *T. kirilowii* was ligated to commercially available arms of lambda ZAPII (Stratagene, La Jolla, Calif.). This ligated mixture was packaged using Gigapack gold TM ](mcr-; Stratagene) and plated using NM554 (mcr-; available from Stratagene) host. The entire packaging reaction was plated. Following plaque formation, DNA was transferred directly to nitrocellulose filters for probing; the bank was not amplified prior to filter lifts to avoid altering the representation of phage clones resulting from nonuniform plaque growth. The genomic DNA bank size was about $1.5 \times 10^6$. The nitrocellulose filters were probed with the EcoRI-EcoRI insert of pQ30E (ie. sequence shown in FIG. 16) which was radiolabelled by random-priming (Boehringer Mannheim). The filters were washed using $2 \times SSC$ at 50° C. (i.e., under low stringency conditions).

Twenty-two clones demonstrated a positive hybridization reaction through tertiary plaques and reprobing. Of these, 21 phage clones were rescued as pBluescript TM (Stratagene, per manufacturer's instructions) plasmid clones. The rescued plasmids were isolated and their restriction enzyme digestion patterns analyzed using EcoRI, SpeI, SacI, SalI, NcoI, ClaI and several doubledigestion combinations of these enzymes. Out of the 21 plasmids, 11 different restriction enzyme digestion patterns were observed.

Preliminary double-stranded nucleic acid sequencing reactions were performed on the inserts of representative plasmids from each of the 11 groups, using the following primers: #477—CGATACATCCTATTTTTTCAACG, derived from the insert of pQ21D;

624—CATCTCTGAGGAACAATC and #1546—CTTATATCATTATGACTCCAAAG, derived from the insert of pQ30E; and

3AS—TTGTATCTCCATGACTCCAAAGC, #3BAS—CAAGGTGGAAATGGCACTGCTC, and #3CAS—CCTCGAAGCCTCAGCAGTAGT, derived from a new clone, clone #3. The last three primers were obtained from sequences determined for clone #3 using primer #477.

Ten of the 11 plasmid inserts yielded sequence data: 5 inserts appeared to give significantly different sequences and were selected for detailed sequence analysis.

Sequencing was achieved using the above-described primers and, further, primers were generated based on the sequence data as it was obtained. The DNA sequences encoding the TCS-like protein and some flanking sequences were determined for each clone. The final results indicated that insert 24 (FIG. 17) and insert 40 were siblings, and that insert 24 (FIG. 17) and insert 2 (FIG. 18) were likely derived from alleles because the coding sequences were identical but the 3' flanking sequences contained a few nucleotide differences. Insert 3 (FIG. 19) and insert 12 (FIG. 20) were unique and encode unique proteins. FIGS. 17 to 20 show the protein coding strand of the DNA sequence determined for each unique clone. The nucleic acids are numbered above the sequence for reference. Unique restriction sites which occur in the sequences are overlined above the sequence and indicated by the restriction enzyme name. The clones are further distinguishable and recognizable by different restriction enzyme digestion profiles in the coding regions.

FIG. 16 illustrates the translation product encoded by the insert of pQ30E. FIGS. 17 to 20 illustrate the translation products encoded by the sequences that are the putative pre-pro-proteins homologous to alpha-trichosanthin. The amino acids are numbered below the protein sequence for convenience. The putative secretory signal peptides are indicated by negative numbers (see below). The secreted pro-proteins are labeled with positive numbers.

Figure 21:
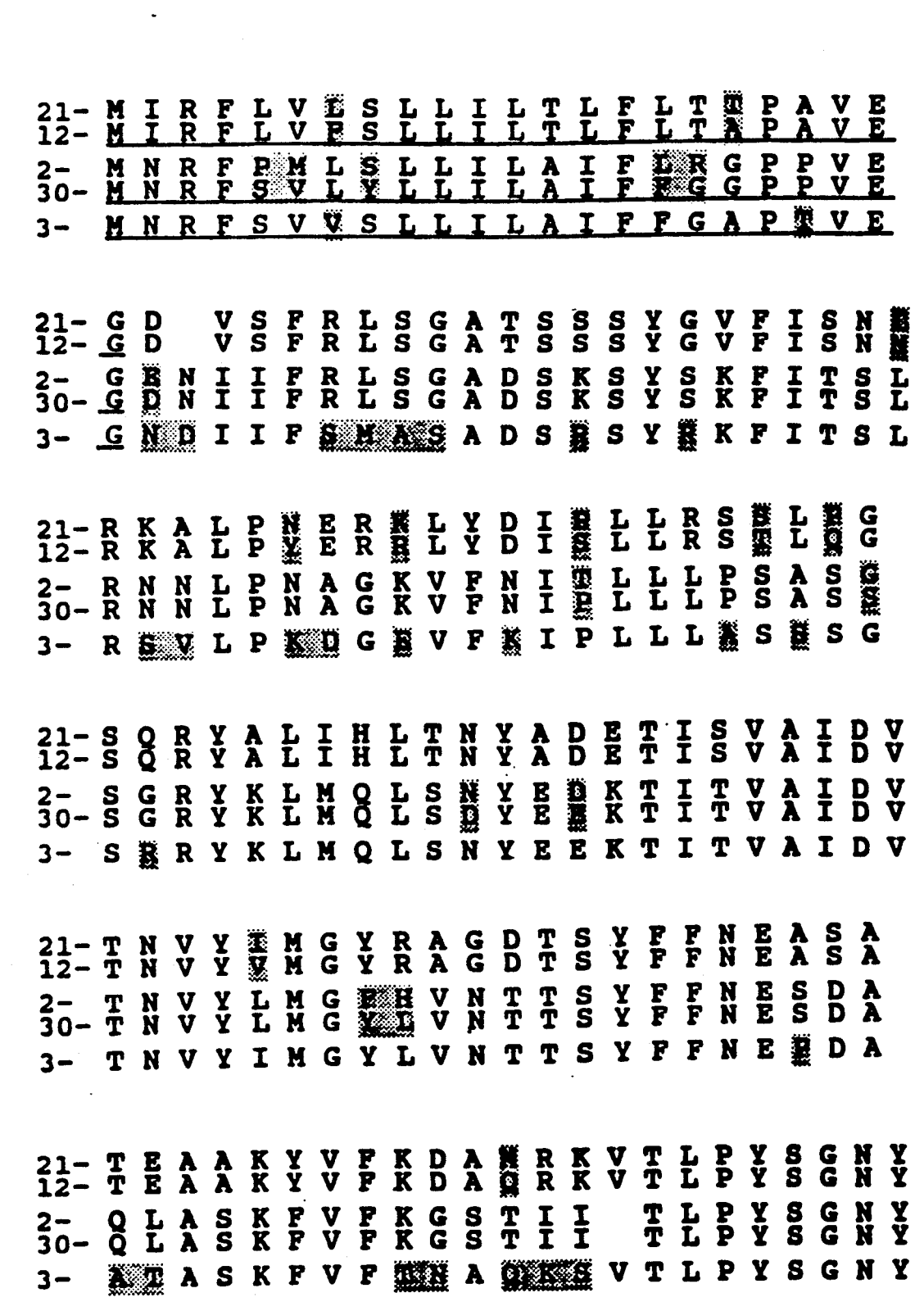
Figure 21:
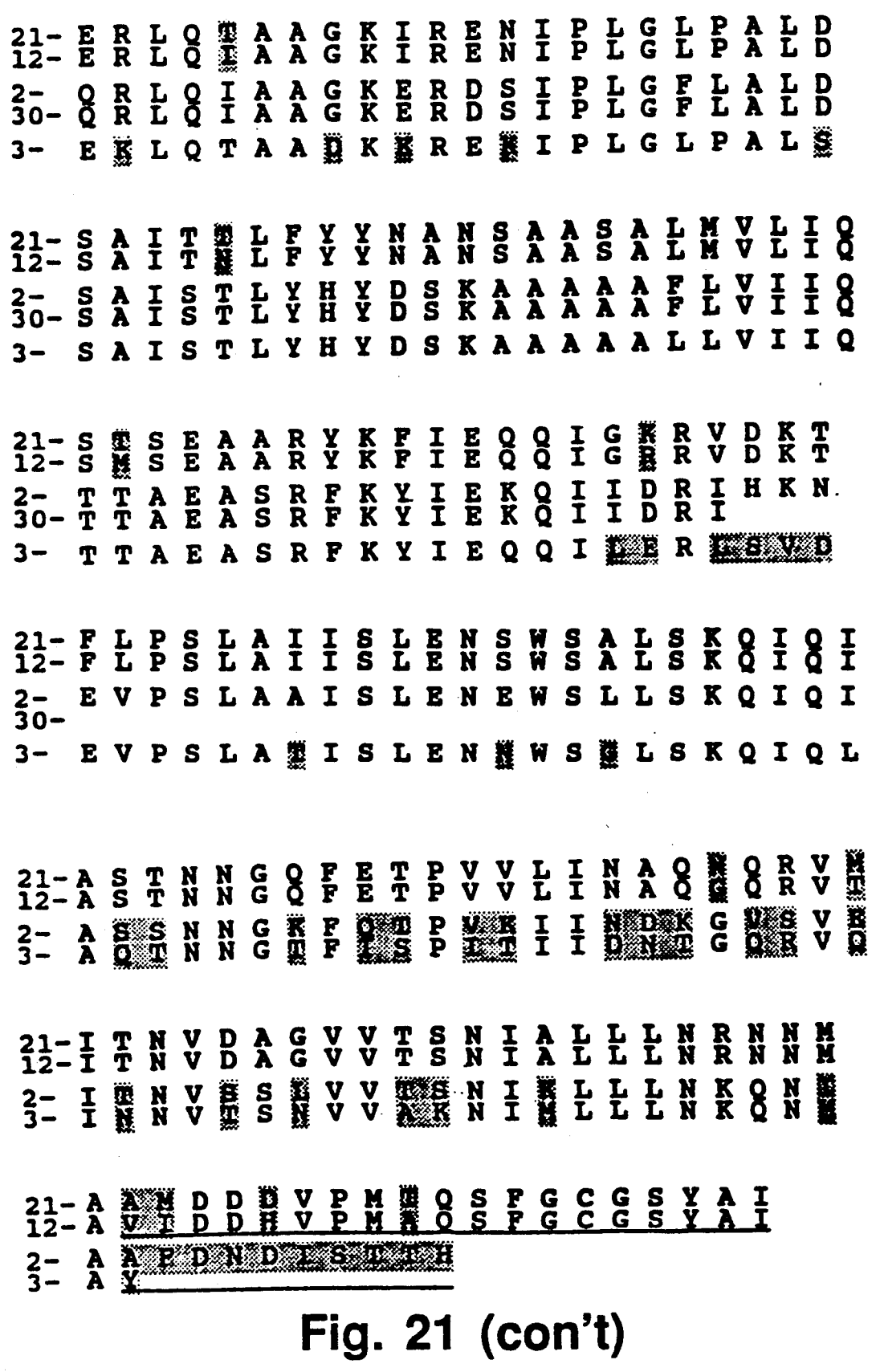

An alignment of the protein sequences corresponding to the nucleic acid sequences of inserts 2, 3, 12, and of 21D (alpha-trichosanthin) and 30 (the sequence of the partial clone referred to in Example 2) is presented in FIG. 21. The proteins have been placed into 3 major groups based on their homologies: 21/12; 2/30; and 3. With reference to FIG. 21: (1) the amino acid residues which differ within a subgroup are shaded; and, (2) the putative secretory signal peptide sequences and putative carboxy terminal extension peptides are underlined. The putative secretory and carboxy extension sequences for inserts 2, 3, 12, and 30 sequences are inferred by alignment of their translated protein sequence with the translated protein sequence of clone 21D (alpha-trichosanthin), and from further comparison to the known mature protein sequence for TCS. While the putative signal peptides are very homologous for the proteins being compared, the carboxy extensions differ significantly in their sequences.

Figure 22:
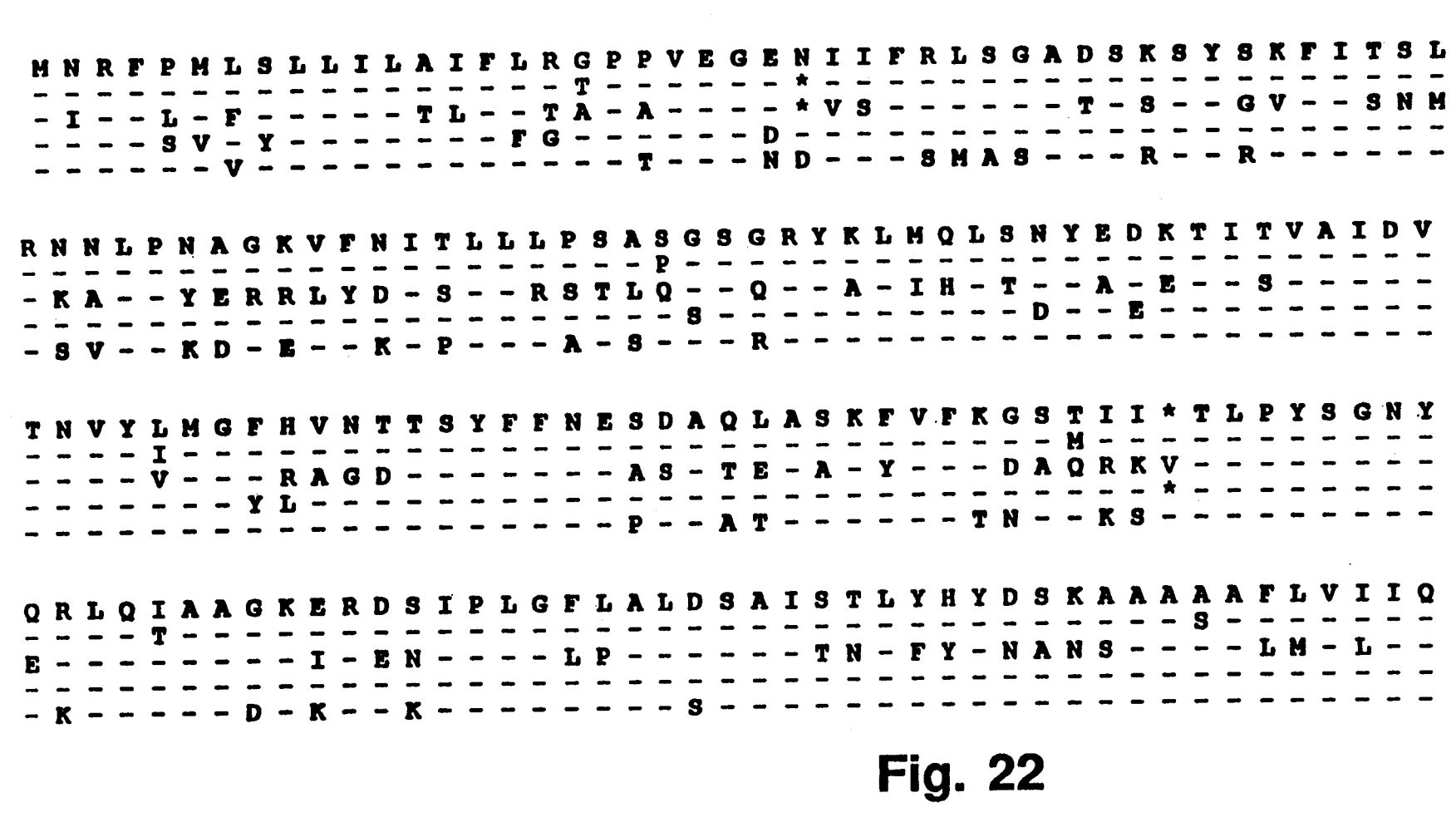
Figure 22:
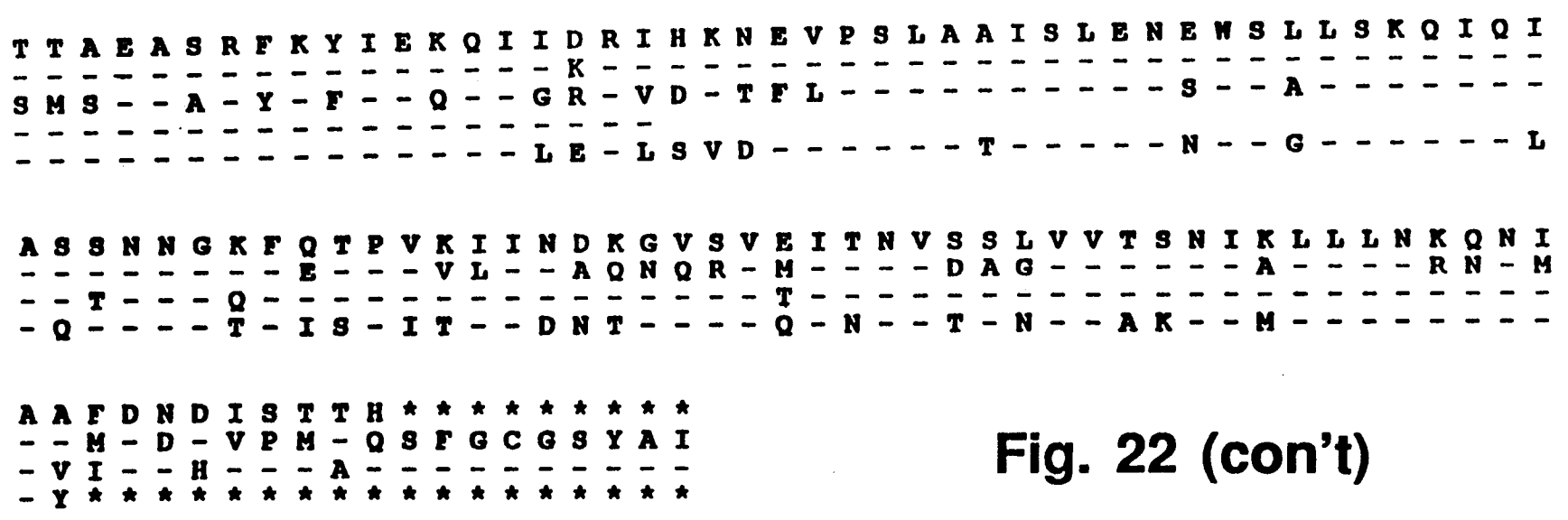

FIG. 22 also illustrates a comparison of the proteins encoded by the above-described RIP gene family of *T. kirilowii*. This figure uses as a reference the protein coding sequence of the insert from clone pQ2. The other 4 known RIP peptide sequences are aligned as described above for FIG. 21: the vertical columns represent possible amino acid substitutions at each site based on this sequence alignment. Sites where amino acid omissions occur are indicated by an asterisk (*). The hyphens are used merely to mark spaces and to allow for easier column alignment.

Although the invention has been described with reference to specific methods and compositions, it will be apparent to one skilled in the art how various modifications and applications of the methods may be made without departing from the invention.

It is claimed:

1. A purified and isolated nucleic acid having a nucleotide sequence encoding a protein sequence selected from the group consisting of the amino acid sequences presented as SEQ ID NO: 1, SEQ ID NO: 3, and SEQ ID NO:5.

2. A purified and isolated nucleic acid having a nucleotide sequence encoding a protein sequence selected from the group consisting of the amino acid sequences presented as SEQ ID NO:2, SEQ ID NO:4, and SEQ ID NO:6.

* * * * *

UNITED STATES PATENT AND TRADEMARK OFFICE
CERTIFICATE OF CORRECTION

PATENT NO. : 5,128,460

DATED : July 7, 1992

INVENTOR(S) : Michael Piatak, Jr., et al.

Page 1 of 13

It is certified that error appears in the above-identified patent and that said Letters Patent is hereby corrected as shown below:

Column 30, after line 55, insert the following pages:

Signed and Sealed this

Sixteenth Day of March, 1993

*Attest:*

STEPHEN G. KUNIN

*Attesting Officer*

*Acting Commissioner of Patents and Trademarks*

PATENT NO. : 5,128,460

SEQUENCE LISTING (1) GENERAL INFORMATION:

(i) APPLICANT: Piatak Jr., Michael
                Chow, Theresa P.
                Fry, Kirk (ii) TITLE OF INVENTION: RECOMBINANT TRICHOSANTHIN AND CODING SEQUENCE (iii) NUMBER OF SEQUENCES: 10

(iv) CORRESPONDENCE ADDRESS:
(A) ADDRESSEE: Law Offices of Peter Dehlinger
(B) STREET: 350 Cambridge Avenue, Suite 300
(C) CITY: Palo Alto
(D) STATE: CA
(E) COUNTRY: USA
(F) ZIP: 94306

(v) COMPUTER READABLE FORM:
(A) MEDIUM TYPE: Floppy disk
(B) COMPUTER: IBM PC compatible
(C) OPERATING SYSTEM: PC-DOS/MS-DOS
(D) SOFTWARE: PatentIn Release #1.0, Version #1.25

(vi) CURRENT APPLICATION DATA:
(A) APPLICATION NUMBER: US 07/504,775
(B) FILING DATE: 04-APR-1990
(C) CLASSIFICATION:

(vii) PRIOR APPLICATION DATA:
(A) APPLICATION NUMBER: US 07/333,184
(B) FILING DATE: 04-APR-1989

(viii) ATTORNEY/AGENT INFORMATION:
(A) NAME: Fabian, Gary R.
(B) REGISTRATION NUMBER: 33,875
(C) REFERENCE/DOCKET NUMBER: 4600-0066.23

(ix) TELECOMMUNICATION INFORMATION:
(A) TELEPHONE: (415) 324-0880
(B) TELEFAX: (415) 324-0960

(2) INFORMATION FOR SEQ ID NO:1:

(i) SEQUENCE CHARACTERISTICS:
(A) LENGTH: 280 amino acids
(B) TYPE: amino acid
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: TRICHOSANTHES KIRILOWII (vii) IMMEDIATE SOURCE:

PATENT NO. : 5,128,460

(B) CLONE: from pQ2

(xi) SEQUENCE DESCRIPTION: SEQ ID NO:1:

```
Met Asn Arg Phe Pro Met Leu Ser Leu Leu Ile Leu Ala Ile Phe Leu
 1               5                  10                  15
Arg Gly Pro Pro Val Glu Gly Glu Asn Ile Ile Phe Arg Leu Ser Gly
             20                  25                  30
Ala Asp Ser Lys Ser Tyr Ser Lys Phe Ile Thr Ser Leu Arg Asn Asn
         35                  40                  45
Leu Pro Asn Ala Gly Lys Val Phe Asn Ile Thr Leu Leu Leu Pro Ser
     50                  55                  60
Ala Ser Gly Ser Gly Arg Tyr Lys Leu Met Gln Leu Ser Asn Tyr Glu
 65                  70                  75                  80
Asp Lys Thr Ile Thr Val Ala Ile Asp Val Thr Asn Val Tyr Leu Met
                 85                  90                  95
Gly Phe His Val Asn Thr Thr Ser Tyr Phe Phe Asn Glu Ser Asp Ala
            100                 105                 110
Gln Leu Ala Ser Lys Phe Val Phe Lys Gly Ser Thr Ile Ile Thr Leu
        115                 120                 125
Pro Tyr Ser Gly Asn Tyr Gln Arg Leu Gln Ile Ala Ala Gly Lys Glu
    130                 135                 140
Arg Asp Ser Ile Pro Leu Gly Phe Leu Ala Leu Asp Ser Ala Ile Ser
145                 150                 155                 160
Thr Leu Tyr His Tyr Asp Ser Lys Ala Ala Ala Ala Phe Lys Tyr Ile Glu Lys
                165                 170                 175
Ile Ile Gln Thr Thr Ala Glu Ala Ser Arg Phe Lys Tyr Ile Glu Lys
            180                 185                 190
Gln Ile Ile Asp Arg Ile His Lys Asn Glu Val Pro Ser Leu Ala Ala
        195                 200                 205
Ile Ser Leu Glu Asn Glu Trp Ser Leu Leu Ser Lys Gln Ile Gln Ile
    210                 215                 220
Ala Ser Ser Asn Asn Gly Lys Phe Gln Thr Pro Val Lys Ile Ile Asn
225                 230                 235                 240
Asp Lys Gly Val Ser Val Glu Ile Thr Asn Val Ser Ser Leu Val Val
                245                 250                 255
Thr Ser Asn Ile Lys Leu Leu Leu Asn Lys Gln Asn Ile Ala Ala Phe
            260                 265                 270
Asp Asn Asp Ile Ser Thr Thr His
        275                 280
```

(2) INFORMATION FOR SEQ ID NO:2:

(i) SEQUENCE CHARACTERISTICS:
(A) LENGTH: 247 amino acids
(B) TYPE: amino acid (D) TOPOLOGY: linear (ii) MOLECULE TYPE: protein (iii) HYPOTHETICAL: NO (iv) ANTI-SENSE: NO (vi) ORIGINAL SOURCE:
    (A) ORGANISM: TRICHOSANTHES KIRILOWII (vii) IMMEDIATE SOURCE:
    (B) CLONE: from pQ2

(xi) SEQUENCE DESCRIPTION: SEQ ID NO:2:

```
Glu Asn Ile Ile Phe Arg Leu Ser Gly Ala Asp Ser Lys Ser Tyr Ser
1               5                   10                  15

Lys Phe Ile Thr Ser Leu Arg Asn Asn Leu Pro Asn Ala Gly Lys Val
            20                  25                  30

Phe Asn Ile Thr Leu Leu Leu Pro Ser Ala Ser Gly Ser Gly Arg Tyr
        35                  40                  45

Lys Leu Met Gln Leu Ser Asn Tyr Glu Asp Lys Thr Ile Thr Val Ala
    50                  55                  60

Ile Asp Val Thr Asn Val Tyr Leu Met Gly Phe His Val Asn Thr Thr
65              70                  75                  80

Ser Tyr Phe Phe Asn Glu Ser Asp Ala Gln Leu Ala Ser Lys Phe Val
                85                  90                  95

Phe Lys Gly Ser Thr Ile Ile Thr Leu Pro Tyr Ser Gly Asn Tyr Gln
            100                 105                 110

Arg Leu Gln Ile Ala Ala Gly Lys Glu Arg Asp Ser Ile Pro Leu Gly
        115                 120                 125

Phe Leu Ala Leu Asp Ser Ala Ile Ser Thr Leu Tyr His Tyr Asp Ser
    130                 135                 140

Lys Ala Ala Ala Ala Ala Phe Leu Val Ile Ile Gln Thr Thr Ala Glu
145                 150                 155                 160

Ala Ser Arg Phe Lys Tyr Ile Glu Lys Gln Ile Ile Asp Arg Ile His
            165                 170                 175

Lys Asn Glu Val Pro Ser Leu Ala Ala Ile Ser Leu Glu Asn Glu Trp
        180                 185                 190

Ser Leu Leu Ser Lys Gln Ile Gln Ile Ala Ser Ser Asn Asn Gly Lys
    195                 200                 205

Phe Gln Thr Pro Val Lys Ile Ile Asn Asp Lys Gly Val Ser Val Glu
210                 215                 220

Ile Thr Asn Val Ser Ser Leu Val Val Thr Ser Asn Ile Lys Leu Leu
225                 230                 235                 240

Leu Asn Lys Gln Asn Ile Ala
            245
```

(2) INFORMATION FOR SEQ ID NO:3:

(i) SEQUENCE CHARACTERISTICS:
        (A) LENGTH: 272 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ3

(xi) SEQUENCE DESCRIPTION: SEQ ID NO:3:

```
Met Asn Arg Phe Ser Val Val Ser Leu Leu Ile Leu Ala Ile Phe Phe
 1               5                  10                  15

Gly Ala Pro Thr Val Glu Gly Asn Asp Ile Ile Phe Ser Met Ala Ser
             20                  25                  30

Ala Asp Ser Arg Ser Tyr Arg Lys Phe Ile Thr Ser Leu Arg Ser Val
         35                  40                  45

Leu Pro Lys Asp Gly Glu Val Phe Lys Ile Pro Leu Leu Leu Ala Ser
     50                  55                  60

Ser Ser Gly Ser Arg Arg Tyr Lys Leu Met Gln Leu Ser Asn Tyr Glu
65                  70                  75                  80

Glu Lys Thr Ile Thr Val Ala Ile Asp Val Thr Asn Val Tyr Ile Met
                 85                  90                  95

Gly Tyr Leu Val Asn Thr Thr Ser Tyr Phe Phe Asn Glu Pro Asp Ala
            100                 105                 110

Ala Thr Ala Ser Lys Phe Val Phe Thr Asn Ala Gln Lys Ser Val Thr
        115                 120                 125

Leu Pro Tyr Ser Gly Asn Tyr Glu Lys Leu Gln Thr Ala Ala Asp Lys
    130                 135                 140

Lys Arg Glu Lys Ile Pro Leu Gly Leu Pro Ala Leu Ser Ser Ala Ile
145                 150                 155                 160

Ser Thr Leu Tyr His Tyr Asp Ser Lys Ala Ala Ala Ala Leu Leu
                165                 170                 175

Val Ile Ile Gln Thr Thr Ala Glu Ala Ser Arg Phe Lys Tyr Ile Glu
            180                 185                 190

Gln Gln Ile Leu Glu Arg Leu Ser Val Asp Glu Val Pro Ser Leu Ala
        195                 200                 205

Thr Ile Ser Leu Glu Asn Asn Trp Ser Gly Leu Ser Lys Gln Ile Gln
    210                 215                 220
```

```
Leu Ala Gln Thr Asn Asn Gly Thr Phe Ile Ser Pro Ile Thr Ile Ile
225                 230                 235                 240

Asp Asn Thr Gly Gln Arg Val Gln Ile Asn Asn Val Thr Ser Asn Val
                245                 250                 255

Val Ala Lys Asn Ile Met Leu Leu Leu Asn Lys Gln Asn Met Ala Tyr
            260                 265                 270
```

(2) INFORMATION FOR SEQ ID NO:4:

(i) SEQUENCE CHARACTERISTICS:
        (A) LENGTH: 248 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ3

(xi) SEQUENCE DESCRIPTION: SEQ ID NO:4:

```
Asn Asp Ile Ile Phe Ser Met Ala Ser Ala Asp Ser Arg Ser Tyr Arg
1               5                   10                  15

Lys Phe Ile Thr Ser Leu Arg Ser Val Leu Pro Lys Asp Gly Glu Val
                20                  25                  30

Phe Lys Ile Pro Leu Leu Leu Ala Ser Ser Ser Gly Ser Arg Arg Tyr
            35                  40                  45

Lys Leu Met Gln Leu Ser Asn Tyr Glu Glu Lys Thr Ile Thr Val Ala
        50                  55                  60

Ile Asp Val Thr Asn Val Tyr Ile Met Gly Tyr Leu Val Asn Thr Thr
65                  70                  75                  80

Ser Tyr Phe Phe Asn Glu Pro Asp Ala Ala Thr Ala Ser Lys Phe Val
                85                  90                  95

Phe Thr Asn Ala Gln Lys Ser Val Thr Leu Pro Tyr Ser Gly Asn Tyr
            100                 105                 110

Glu Lys Leu Gln Thr Ala Ala Asp Lys Lys Arg Glu Lys Ile Pro Leu
        115                 120                 125

Gly Leu Pro Ala Leu Ser Ser Ala Ile Ser Thr Leu Tyr His Tyr Asp
    130                 135                 140

Ser Lys Ala Ala Ala Ala Ala Leu Leu Val Ile Ile Gln Thr Thr Ala
145                 150                 155                 160

Glu Ala Ser Arg Phe Lys Tyr Ile Glu Gln Gln Ile Leu Glu Arg Leu
                165                 170                 175
```

```
Ser Val Asp Glu Val Pro Ser Leu Ala Thr Ile Ser Leu Glu Asn Asn
            180                 185                 190

Trp Ser Gly Leu Ser Lys Gln Ile Gln Leu Ala Gln Thr Asn Asn Gly
        195                 200                 205

Thr Phe Ile Ser Pro Ile Thr Ile Ile Asp Asn Thr Gly Gln Arg Val
        210                 215                 220

Gln Ile Asn Asn Val Thr Ser Asn Val Val Ala Lys Asn Ile Met Leu
225                 230                 235                 240

Leu Leu Asn Lys Gln Asn Met Ala
                245
```

(2) INFORMATION FOR SEQ ID NO:5:

(i) SEQUENCE CHARACTERISTICS:
        (A) LENGTH: 289 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ12

(xi) SEQUENCE DESCRIPTION: SEQ ID NO:5:

```
Met Ile Arg Phe Leu Val Phe Ser Leu Leu Ile Leu Thr Leu Phe Leu
1               5                   10                  15

Thr Ala Pro Ala Val Glu Gly Asp Val Ser Phe Arg Leu Ser Gly Ala
            20                  25                  30

Thr Ser Ser Ser Tyr Gly Val Phe Ile Ser Asn Met Arg Lys Ala Leu
            35                  40                  45

Pro Tyr Glu Arg Arg Leu Tyr Asp Ile Ser Leu Leu Arg Ser Thr Leu
50                  55                  60

Gln Gly Ser Gln Arg Tyr Ala Leu Ile His Leu Thr Asn Tyr Ala Asp
65                  70                  75                  80

Glu Thr Ile Ser Val Ala Ile Asp Val Thr Asn Val Tyr Val Met Gly
            85                  90                  95

Tyr Arg Ala Gly Asp Thr Ser Tyr Phe Phe Asn Glu Ala Ser Ala Thr
            100                 105                 110

Glu Ala Ala Lys Tyr Val Phe Lys Asp Ala Gln Arg Lys Val Thr Leu
            115                 120                 125

Pro Tyr Ser Gly Asn Tyr Glu Arg Leu Gln Ile Ala Ala Gly Lys Ile
            130                 135                 140
```

```
     Arg Glu Asn Ile Pro Leu Gly Leu Pro Ala Leu Asp Ser Ala Ile Thr
     145                 150                 155                 160

Asn Leu Phe Tyr Tyr Asn Ala Asn Ser Ala Ala Ser Ala Leu Met Val
                     165                 170                 175

Leu Ile Gln Ser Met Ser Glu Ala Ala Arg Tyr Lys Phe Ile Glu Gln
                 180                 185                 190

Gln Ile Gly Arg Arg Val Asp Lys Thr Phe Leu Pro Ser Leu Ala Ile
             195                 200                 205

Ile Ser Leu Glu Asn Ser Trp Ser Ala Leu Ser Lys Gln Ile Gln Ile
     210                 215                 220

Ala Ser Thr Asn Asn Gly Gln Phe Glu Thr Pro Val Val Leu Ile Asn
     225                 230                 235                 240

Ala Gln Gly Gln Arg Val Thr Ile Thr Asn Val Asp Ala Gly Val Val
                     245                 250                 255

Thr Ser Asn Ile Ala Leu Leu Leu Asn Arg Asn Asn Met Ala Val Ile
                 260                 265                 270

Asp Asp His Val Pro Met Ala Gln Ser Phe Gly Cys Gly Ser Tyr Ala
             275                 280                 285

Ile
```

(2) INFORMATION FOR SEQ ID NO:6:

(i) SEQUENCE CHARACTERISTICS:
        (A) LENGTH: 247 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ12

(xi) SEQUENCE DESCRIPTION: SEQ ID NO:6:

```
     Asp Val Ser Phe Arg Leu Ser Gly Ala Thr Ser Ser Ser Tyr Gly Val
     1               5                   10                  15

Phe Ile Ser Asn Met Arg Lys Ala Leu Pro Tyr Glu Arg Arg Leu Tyr
                     20                  25                  30

Asp Ile Ser Leu Leu Arg Ser Thr Leu Gln Gly Ser Gln Arg Tyr Ala
                 35                  40                  45

Leu Ile His Leu Thr Asn Tyr Ala Asp Glu Thr Ile Ser Val Ala Ile
             50                  55                  60
```

```
    Asp Val Thr Asn Val Tyr Val Met Gly Tyr Arg Ala Gly Asp Thr Ser
    65              70                  75                  80

Tyr Phe Phe Asn Glu Ala Ser Ala Thr Glu Ala Ala Lys Tyr Val Phe
                    85                  90                  95

Lys Asp Ala Gln Arg Lys Val Thr Leu Pro Tyr Ser Gly Asn Tyr Glu
                100                 105                 110

Arg Leu Gln Ile Ala Ala Gly Lys Ile Arg Glu Asn Ile Pro Leu Gly
            115                 120                 125

Leu Pro Ala Leu Asp Ser Ala Ile Thr Asn Leu Phe Tyr Tyr Asn Ala
        130                 135                 140

Asn Ser Ala Ala Ser Ala Leu Met Val Leu Ile Gln Ser Met Ser Glu
    145                 150                 155                 160

Ala Ala Arg Tyr Lys Phe Ile Glu Gln Gln Ile Gly Arg Arg Val Asp
                    165                 170                 175

Lys Thr Phe Leu Pro Ser Leu Ala Ile Ile Ser Leu Glu Asn Ser Trp
                180                 185                 190

Ser Ala Leu Ser Lys Gln Ile Gln Ile Ala Ser Thr Asn Asn Gly Gln
            195                 200                 205

Phe Glu Thr Pro Val Val Leu Ile Asn Ala Gln Gly Gln Arg Val Thr
        210                 215                 220

Ile Thr Asn Val Asp Ala Gly Val Val Thr Ser Asn Ile Ala Leu Leu
    225                 230                 235                 240

Leu Asn Arg Asn Asn Met Ala
                    245
```

(2) INFORMATION FOR SEQ ID NO:7:

(i) SEQUENCE CHARACTERISTICS:
        (A) LENGTH: 198 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ30E (xi) SEQUENCE DESCRIPTION: SEQ ID NO:7:

```
    Met Asn Arg Phe Ser Val Leu Tyr Leu Leu Ile Leu Ala Ile Phe Phe
    1               5                   10                  15

Gly Gly Pro Pro Val Glu Gly Asp Asn Ile Ile Phe Arg Leu Ser Gly
                20                  25                  30
```

```
              Ala Asp Ser Lys Ser Tyr Ser Lys Phe Ile Thr Ser Leu Arg Asn Asn
                      35              40                  45

Leu Pro Asn Ala Gly Lys Val Phe Asn Ile Pro Leu Leu Pro Ser
                  50              55                  60

Ala Ser Ser Ser Gly Arg Tyr Lys Leu Met Gln Leu Ser Asp Tyr Glu
              65              70                  75                      80

Glu Lys Thr Ile Thr Val Ala Ile Asp Val Thr Asn Val Tyr Leu Met
                              85              90                      95

Gly Tyr Leu Val Asn Thr Thr Ser Tyr Phe Phe Asn Glu Ser Asp Ala
                          100                 105                 110

Gln Leu Ala Ser Lys Phe Val Phe Lys Gly Ser Thr Ile Ile Thr Leu
                      115                 120                 125

Pro Tyr Ser Gly Asn Tyr Gln Arg Leu Gln Ile Ala Ala Gly Lys Glu
                  130                 135                 140

Arg Asp Ser Ile Pro Leu Gly Phe Leu Ala Leu Asp Ser Ala Ile Ser
              145             150                 155                     160

Thr Leu Tyr His Tyr Asp Ser Lys Ala Ala Ala Ala Phe Leu Val
                          165                 170                 175

Ile Ile Gln Thr Thr Ala Glu Ala Ser Arg Phe Lys Tyr Ile Glu Lys
                          180                 185                 190

Gln Ile Ile Asp Arg Ile
                          195

(2) INFORMATION FOR SEQ ID NO:8:

(i) SEQUENCE CHARACTERISTICS:
            (A) LENGTH: 175 amino acids
            (B) TYPE: amino acid
            (D) TOPOLOGY: linear (ii) MOLECULE TYPE: protein (iii) HYPOTHETICAL: NO (iv) ANTI-SENSE: NO (vi) ORIGINAL SOURCE:
            (A) ORGANISM: TRICHOSANTHES KIRILOWII (vii) IMMEDIATE SOURCE:
            (B) CLONE: from pQ30E (xi) SEQUENCE DESCRIPTION: SEQ ID NO:8:

Asp Asn Ile Ile Phe Arg Leu Ser Gly Ala Asp Ser Lys Ser Tyr Ser
       1               5                   10                  15

Lys Phe Ile Thr Ser Leu Arg Asn Asn Leu Pro Asn Ala Gly Lys Val
                       20                  25                  30

Phe Asn Ile Pro Leu Leu Leu Pro Ser Ala Ser Ser Ser Gly Arg Tyr
                   35                  40                  45
```

```
Lys Leu Met Gln Leu Ser Asp Tyr Glu Glu Lys Thr Ile Thr Val Ala
    50              55              60
Ile Asp Val Thr Asn Val Tyr Leu Met Gly Tyr Leu Val Asn Thr Thr
65              70              75              80
Ser Tyr Phe Phe Asn Glu Ser Asp Ala Gln Leu Ala Ser Lys Phe Val
                85              90              95
Phe Lys Gly Ser Thr Ile Ile Thr Leu Pro Tyr Ser Gly Asn Tyr Gln
            100             105             110
Arg Leu Gln Ile Ala Ala Gly Lys Glu Arg Asp Ser Ile Pro Leu Gly
        115             120             125
Phe Leu Ala Leu Asp Ser Ala Ile Ser Thr Leu Tyr His Tyr Asp Ser
    130             135             140
Lys Ala Ala Ala Ala Ala Phe Leu Val Ile Ile Gln Thr Thr Ala Glu
145             150             155             160
Ala Ser Arg Phe Lys Tyr Ile Glu Lys Gln Ile Ile Asp Arg Ile
            165             170             175
```

(2) INFORMATION FOR SEQ ID NO:9:

(i) SEQUENCE CHARACTERISTICS:
        (A) LENGTH: 289 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (B) CLONE: from pQ21D (xi) SEQUENCE DESCRIPTION: SEQ ID NO:9:

```
Met Ile Arg Phe Leu Val Leu Ser Leu Leu Ile Leu Thr Leu Phe Leu
1           5               10              15
Thr Thr Pro Ala Val Glu Gly Asp Val Ser Phe Arg Leu Ser Gly Ala
            20              25              30
Thr Ser Ser Ser Tyr Gly Val Phe Ile Ser Asn Leu Arg Lys Ala Leu
        35              40              45
Pro Asn Glu Arg Lys Leu Tyr Asp Ile Pro Leu Leu Arg Ser Ser Leu
    50              55              60
Pro Gly Ser Gln Arg Tyr Ala Leu Ile His Leu Thr Asn Tyr Ala Asp
65              70              75              80
Glu Thr Ile Ser Val Ala Ile Asp Val Thr Asn Val Tyr Ile Met Gly
                85              90              95
```

```
Tyr Arg Ala Gly Asp Thr Ser Tyr Phe Asn Glu Ala Ser Ala Thr
            100                 105                 110

Glu Ala Ala Lys Tyr Val Phe Lys Asp Ala Met Arg Lys Val Thr Leu
            115                 120                 125

Pro Tyr Ser Gly Asn Tyr Glu Arg Leu Gln Thr Ala Ala Gly Lys Ile
            130                 135                 140

Arg Glu Asn Ile Pro Leu Gly Leu Pro Ala Leu Asp Ser Ala Ile Thr
145                 150                 155                 160

Thr Leu Phe Tyr Tyr Asn Ala Asn Ser Ala Ala Ser Ala Leu Met Val
                165                 170                 175

Leu Ile Gln Ser Thr Ser Glu Ala Ala Arg Tyr Lys Phe Ile Glu Gln
            180                 185                 190

Gln Ile Gly Lys Arg Val Asp Lys Thr Phe Leu Pro Ser Leu Ala Ile
            195                 200                 205

Ile Ser Leu Glu Asn Ser Trp Ser Ala Leu Ser Lys Gln Ile Gln Ile
    210                 215                 220

Ala Ser Thr Asn Asn Gly Gln Phe Glu Thr Pro Val Val Leu Ile Asn
225                 230                 235                 240

Ala Gln Asn Gln Arg Val Met Ile Thr Asn Val Asp Ala Gly Val Val
                245                 250                 255

Thr Ser Asn Ile Ala Leu Leu Leu Asn Arg Asn Asn Met Ala Ala Met
            260                 265                 270

Asp Asp Asp Val Pro Met Thr Gln Ser Phe Gly Cys Gly Ser Tyr Ala
    275                 280                 285

Ile
```

(2) INFORMATION FOR SEQ ID NO:10:

(i) SEQUENCE CHARACTERISTICS:
        (A) LENGTH: 247 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: TRICHOSANTHES KIRILOWII (vii) IMMEDIATE SOURCE:
        (A) LIBRARY: from pQ21D (xi) SEQUENCE DESCRIPTION: SEQ ID NO:10:

```
Asp Val Ser Phe Arg Leu Ser Gly Ala Thr Ser Ser Ser Tyr Gly Val
1               5                   10                  15
```

PATENT NO. 5,128,460

```
Phe Ile Ser Asn Leu Arg Lys Ala Leu Pro Asn Glu Arg Lys Leu Tyr
            20                  25                  30
Asp Ile Pro Leu Leu Arg Ser Ser Leu Pro Gly Ser Gln Arg Tyr Ala
            35                  40                  45
Leu Ile His Leu Thr Asn Tyr Ala Asp Glu Thr Ile Ser Val Ala Ile
            50                  55                  60
Asp Val Thr Asn Val Tyr Ile Met Gly Tyr Arg Ala Gly Asp Thr Ser
65                  70                  75                  80
Tyr Phe Phe Asn Glu Ala Ser Ala Thr Glu Ala Ala Lys Tyr Val Phe
                85                  90                  95
Lys Asp Ala Met Arg Lys Val Thr Leu Pro Tyr Ser Gly Asn Tyr Glu
                100                 105                 110
Arg Leu Gln Thr Ala Ala Gly Lys Ile Arg Glu Asn Ile Pro Leu Gly
            115                 120                 125
Leu Pro Ala Leu Asp Ser Ala Ile Thr Thr Leu Phe Tyr Tyr Asn Ala
            130                 135                 140
Asn Ser Ala Ala Ser Ala Leu Met Val Leu Ile Gln Ser Thr Ser Glu
145                 150                 155                 160
Ala Ala Arg Tyr Lys Phe Ile Glu Gln Gln Ile Gly Lys Arg Val Asp
                165                 170                 175
Lys Thr Phe Leu Pro Ser Leu Ala Ile Ile Ser Leu Glu Asn Ser Trp
            180                 185                 190
Ser Ala Leu Ser Lys Gln Ile Gln Ile Ala Ser Thr Asn Asn Gly Gln
            195                 200                 205
Phe Glu Thr Pro Val Val Leu Ile Asn Ala Gln Asn Gln Arg Val Met
            210                 215                 220
Ile Thr Asn Val Asp Ala Gly Val Val Thr Ser Asn Ile Ala Leu Leu
225                 230                 235                 240
Leu Asn Arg Asn Asn Met Ala
                245
```